United States Patent [19]
Houghton et al.

[11] Patent Number: 5,885,799
[45] Date of Patent: Mar. 23, 1999

[54] HEPATITIS C VIRUS PROTEASE

[75] Inventors: Michael Houghton, Danville; Qui-Lim Choo, El Cerrito; George Kuo, San Francisco, all of Calif.

[73] Assignee: Chiron Corporation

[21] Appl. No.: 709,177

[22] Filed: Sep. 6, 1996

Related U.S. Application Data

[60] Continuation of Ser. No. 440,548, May 12, 1995, Pat. No. 5,597,691, which is a division of Ser. No. 350,884, Dec. 6, 1994, Pat. No. 5,585,258, which is a division of Ser. No. 680,296, Apr. 4, 1991, Pat. No. 5,371,017, which is a continuation-in-part of Ser. No. 505,433, Apr. 4, 1990, abandoned.

[51] Int. Cl.⁶ .............................. C12N 1/50; C12N 15/57; C12N 15/62; C12N 15/81
[52] U.S. Cl. ........................ 435/69.1; 435/69.7; 435/219; 435/252.3; 435/254.2; 435/320.1; 435/471; 435/483; 536/23.2; 536/23.4; 930/10; 930/14; 930/69; 930/72
[58] Field of Search ........................... 435/23, 69.1, 69.7, 435/219, 172.3, 252.3, 252.33, 254.2, 320.1, 471, 483; 536/23.2, 23.4

[56] References Cited

U.S. PATENT DOCUMENTS

| | | | |
|---|---|---|---|
| 4,673,634 | 6/1987 | Seto et al. | 424/228.1 |
| 4,702,909 | 10/1987 | Vallarejos et al. | 424/228.1 |
| 4,870,026 | 9/1989 | Wands et al. | 435/5 |
| 4,952,493 | 8/1990 | Kettner et al. | 435/5 |
| 5,010,175 | 4/1991 | Rutter et al. | 530/334 |
| 5,176,994 | 1/1993 | Mishiro et al. | 435/5 |
| 5,218,099 | 6/1993 | Reyes et al. | 536/23.72 |
| 5,350,671 | 9/1994 | Houghton et al. | 435/5 |
| 5,371,017 | 12/1994 | Houghton et al. | 435/320.1 |
| 5,585,258 | 12/1996 | Houghton et al. | 435/219 |
| 5,597,691 | 1/1997 | Houghton et al. | 435/23 |

FOREIGN PATENT DOCUMENTS

| | | |
|---|---|---|
| 0419182 | 3/1991 | European Pat. Off. . |
| WO 89/04669 | 6/1989 | WIPO . |

OTHER PUBLICATIONS

Korant, B.D., "Viral proteases: An emerging therapeutic target" *CRC Critical Reviews in Biotechnology* (1988) 8:149–157.

Pichuantes, S., et al., "Expression of authentic and enzymatically active HIV–1 proteinase in bacteria and yeast" *Current Communications in Molecular Biology*, Kräusslich, H., et al., eds., Cold Spring Harbor Laboratory Press, (1989) pp. 215–222.

McQuade, T.J., et al., "A synthetic HIV–1 protease inhibitor with antiviral activity arrests HIV–like particle maturation" *Science* (1990) 247:454–456.

Kubo, Y., et al., "A cDNA fragment of hepatitis C virus isolated from an implicated donor of post–transfusion non–A, non–B hepatitis in Japan" *EMBL Data Library Accession #S06067* Submitted: (Sep. 1989) Dated: (Feb. 28, 1990).

Kubo, Y., et al., "A cDNA fragment of hepatitis C virus isolated from an implicated donor of post–transfusion non–A, non–B hepatitis in Japan" *Nucleic Acids Research* (1989) 17:10367–10372.

(List continued on next page.)

*Primary Examiner*—Robert A. Wax
*Assistant Examiner*—William W. Moore
*Attorney, Agent, or Firm*—Kenneth M. Goldman; Alisa A. Harbin; Robert P. Blackburn

[57] ABSTRACT

The protease necessary for polyprotein processing in Hepatitis C virus is identified, cloned, and expressed. Proteases, truncated protease, and altered proteases are disclosed which are useful for cleavage of specific polypeptides, and for assay and design of antiviral agents specific for HCV.

12 Claims, 23 Drawing Sheets

OTHER PUBLICATIONS

Miller, R.H., et al., "Hepatitis C virus shares amino acid sequence similarity with pestiviruses and flaviviruses as well as members of two plant virus supergroups" *Proceedings of the National Academy of Science USA* (1990) 87:2057–2061.

Inchauspe, G., et al., Proceedings of the National Academy of Sciences, U.S.A., vol. 88, "Genomic structure of the human prototype strain H of hepatitis C virus: comparison with American and Japanese isolates", pp. 10292–10296, 1991.

Choo, Q.-L., et al., Proceedings of the National Academy of Sciences, U.S.A., vol. 88, "Genetic organization and diversity of the hepatitis C virus", pp. 2451–2455, 1991.

Kato, N., et al., Proceedings of the National Academy of Sciences, U.S.A., vol. 87, "Molecular cloning of the human hepatitis C virus genome from Japanese patients with non–A, non–B hepatitis", pp. 9524–9528, 1990.

Takamizawa, A., et al., Journal of Virology, vol. 65, "Structure and organization of the hepatitis C virus genome isolated from human carriers", pp. 1105–1113, 1991.

Okamoto, H., et al., Journal of General Virology, vol. 72, "Nucleotide sequence of the genomic RNA of hepatitis C virus isolated from a human carrier: comparison with reported isolates for conserved and diverent regions", pp. 2697–2704, 1991.

Grakoui, A., et al., Proceedings of the National Academy of Sciences, U.S.A., vol. 90, "A second hepatitis C virus–encoded proteinase ", pp. 10583–10587, 1993.

Chambers, T. J., et al., Proceedings of the National Acacdemy of Sciences, U.S.A., vol. 87, "Evidence that the N–terminal domain of yellow fever virus NS3 protein is a serine protease . . . ", pp. 8898–8902, 1990.

Hijikata, M., et al., Journal of Virology, vol. 67, "Two distinct proteinase activities required for the processing of putative nonstructural precursor protein of hepatitis C virus", pp. 4665–4675, 1993.

```
            1                    5                              10
       Gly Thr Tyr Val Tyr Asn His Leu Thr Pro Leu Arg Asp Trp
ATT CGG GGC ACC TAT GTT TAT AAC CAT CTC ACT CCT CTT CGG GAC TGG
TAA GCC CCG TGG ATA CAA ATA TTG GTA GAG TGA GGA GAA GCC CTG ACC 15                    20                    25                    30
  Ala His Asn Gly Leu Arg Asp Leu Ala Val Ala Val Glu Pro Val Val
  GCG CAC AAC GGC TTG CGA GAT CTG GCC GTG GCT GTA GAG CCA GTC GTC
  CGC GTG TTG CCG AAC GCT CTA GAC CGG CAC CGA CAT CTC GGT CAG CAG 35                    40                    45
Phe Ser Gln Met Glu Thr Lys Leu Ile Thr Trp Gly Ala Asp Thr Ala
TTC TCC CAA ATG GAG ACC AAG CTC ATC ACG TGG GGG GCA GAT ACC GCC
AAG AGG GTT TAC CTC TGG TTC GAG TAG TGC ACC CCC CGT CTA TGG CGG 50                    55                    60
Ala Cys Gly Asp Ile Ile Asn Gly Leu Pro Val Ser Ala Arg Arg Gly
GCG TGC GGT GAC ATC ATC AAC GGC TTG CCT GTT TCC GCC CGC AGG GGC
CGC ACG CCA CTG TAG TAG TTG CCG AAC GGA CAA AGG CGG GCG TCC CCG 65                    70                    75
Arg Glu Ile Leu Leu Gly Pro Ala Asp Gly Met Val Ser Lys Gly Trp
CGG GAG ATA CTG CTC GGG CCA GCC GAT GGA ATG GTC TCC AAG GGT TGG
GCC CTC TAT GAC GAG CCC GGT CGG CTA CCT TAC CAG AGG TTC CCA ACC 80                    85                    90
Arg Leu Leu Ala Pro Ile Thr Ala Tyr Ala Gln Gln Thr Arg Gly Leu
AGG TTG CTG GCG CCC ATC ACG GCG TAC GCC CAG CAG ACA AGG GGC CTC
TCC AAC GAC CGC GGG TAG TGC CGC ATG CGG GTC GTC TGT TCC CCG GAG 95                    100                   105                   110
  Leu Gly Cys Ile Ile Thr Ser Leu Thr Gly Arg Asp Lys Asn Gln Val
  CTA GGG TGC ATA ATC ACC AGC CTA ACT GGC CGG GAC AAA AAC CAA GTG
  GAT CCC ACG TAT TAG TGG TCG GAT TGA CCG GCC CTG TTT TTG GTT CAC 115                   120                   125
Glu Gly Glu Val Gln Ile Val Ser Thr Ala Ala Gln Thr Phe Leu Ala
GAG GGT GAG GTC CAG ATT GTG TCA ACT GCT GCC CAA ACC TTC CTG GCA
CTC CCA CTC CAG GTC TAA CAC AGT TGA CGA CGG GTT TGG AAG GAC CGT
```

FIG. 1A

```
                    130                         135                         140
     Thr Cys Ile Ile Asn Gly Val Cys Trp Thr Val Tyr His Gly Ala Gly
     ACG TGC ATC ATC AAT GGG GTG TGC TGG ACT GTC TAC CAC GGG GCC GGA
     TGC ACG TAG TAG TTA CCC CAC ACG ACC TGA CAG ATG GTG CCC CGG CCT 145                         150                         155
     Thr Arg Thr Ile Ala Ser Pro Lys Gly Pro Val Ile Gln Met Tyr Thr
     ACG AGG ACC ATC GCG TCA CCC AAG GGT CCT GTC ATC CAG ATG TAT ACC
     TGC TCC TGG TAG CGC AGT GGG TTC CCA GGA CAG TAG GTC TAC ATA TGG 160                         165                         170
     Asn Val Asp Gln Asp Leu Val Gly Trp Pro Ala Ser Gln Gly Thr Arg
     AAT GTA GAC CAA GAC CTT GTG GGC TGG CCC GCT TCG CAA GGT ACC CGC
     TTA CAT CTG GTT CTG GAA CAC CCG ACC GGG CGA AGC GTT CCA TGG GCG 175                         180                         185                         190
     Ser Leu Thr Pro Cys Thr Cys Gly Ser Ser Asp Leu Tyr Leu Val Thr
     TCA TTG ACA CCC TGC ACT TGC GGC TCC TCG GAC CTT TAC CTG GTC ACG
     AGT AAC TGT GGG ACG TGA ACG CCG AGG AGC CTG GAA ATG GAC CAG TGC 195                         200                         205
     Arg His Ala Asp Val Ile Pro Val Arg Arg Arg Gly Asp Ser Arg Gly
     AGG CAC GCC GAT GTC ATT CCC GTG CGC CGG CGG GGT GAT AGC AGG GGC
     TCC GTG CGG CTA CAG TAA GGG CAC GCG GCC GCC CCA CTA TCG TCC CCG
                                      ↑
                                    NaeI 210                         215                         220
     Ser Leu Leu Ser Pro Arg Pro Ile Ser Tyr Leu Lys Gly Ser Ser Gly
     AGC CTG CTG TCG CCC CGG CCC ATT TCC TAC TTG AAA GGC TCC TCG GGG
     TCG GAC GAC AGC GGG GCC GGG TAA AGG ATG AAC TTT CCG AGG AGC CCC 225                         230                         235
     Gly Pro Leu Leu Cys Pro Ala Gly His Ala Val Gly Ile Phe Arg Ala
     GGT CCG CTG TTG TGC CCC GCG GGG CAC GCC GTG GGC ATA TTT AGG GCC
     CCA GGC GAC AAC ACG GGG CGC CCC GTG CGG CAC CCG TAT AAA TCC CGG 240                         245                         250
     Ala Val Cys Thr Arg Gly Val Ala Lys Ala Val Asp Phe Ile Pro Val
     GCG GTG TGC ACC CGT GGA GTG GCT AAG GCG GTG GAC TTT ATC CCT GTG
     CGC CAC ACG TGG GCA CCT CAC CGA TTC CGC CAC CTG AAA TAG GGA CAC
```

FIG. IB

```
         255                      260                      265                      270
Glu Asn Leu Glu Thr Thr Met Arg Ser Pro Val Phe Thr Asp Asn Ser
GAG AAC CTA GAG ACA ACC ATG AGG TCC CCG GTG TTC ACG GAT AAC TCC
CTC TTG GAT CTC TGT TGG TAC TCC AGG GGC CAC AAG TGC CTA TTG AGG 275                      280                      285
Ser Pro Pro Val Val Pro Gln Ser Phe Gln Val Ala His Leu His Ala
TCT CCA CCA GTA GTG CCC CAG AGC TTC CAG GTG GCT CAC CTC CAT GCT
AGA GGT GGT CAT CAC GGG GTC TCG AAG GTC CAC CGA GTG GAG GTA CGA 290                      295                      300
Pro Thr Gly Ser Gly Lys Ser Thr Lys Val Pro Ala Ala Tyr Ala Ala
CCC ACA GGC AGC GGC AAA AGC ACC AAG GTC CCG GCT GCA TAT GCA GCT
GGG TGT CCG TCG CCG TTT TCG TGG TTC CAG GGC CGA CGT ATA CGT CGA
                                                      ↑
                                                     NdeI 305                      310                      315
Gln Gly Tyr Lys Val Leu Val Leu Asn Pro Ser Val Ala Ala Thr Leu
CAG GGC TAT AAG GTG CTA GTA CTC AAC CCC TCT GTT GCT GCA ACA CTG
GTC CCG ATA TTC CAC GAT CAT GAG TTG GGG AGA CAA CGA CGT TGT GAC 320                      325                      330
Gly Phe Gly Ala Tyr Met Ser Lys Ala His Gly Ile Asp Pro Asn Ile
GGC TTT GGT GCT TAC ATG TCC AAG GCT CAT GGG ATC GAT CCT AAC ATC
CCG AAA CCA CGA ATG TAC AGG TTC CGA GTA CCC TAG CTA GGA TTG TAG 335                      340                      345                      350
Arg Thr Gly Val Arg Thr Ile Thr Thr Gly Ser Pro Ile Thr Tyr Ser
AGG ACC GGG GTG AGA ACA ATT ACC ACT GGC AGC CCC ATC ACG TAC TCC
TCC TGG CCC CAC TCT TGT TAA TGG TGA CCG TCG GGG TAG TGC ATG AGG 355                      360                      365
Thr Tyr Gly Lys Phe Leu Ala Asp Gly Gly Cys Ser Gly Gly Ala Tyr
ACC TAC GGC AAG TTC CTT GCC GAC GGC GGG TGC TCG GGG GGC GCT TAT
TGG ATG CCG TTC AAG GAA CGG CTG CCG CCC ACG AGC CCC CGA ATA 370                      375                      380
Asp Ile Ile Ile Cys Asp Glu Cys His Ser Thr Asp Ala Thr Ser Ile
GAC ATA ATA ATT TGT GAC GAG TGC CAC TCC ACG GAT GCC ACA TCC ATC
CTG TAT TAT TAA ACA CTG CTC ACG GTG AGG TGC CTA CGG TGT AGG TAG
```

FIG. 1C

```
            385                          390                          395
Leu Gly Ile Gly Thr Val Leu Asp Gln Ala Glu Thr Ala Gly Ala Arg
TTG GGC ATT GGC ACT GTC CTT GAC CAA GCA GAG ACT GCG GGG GCG AGA
AAC CCG TAA CCG TGA CAG GAA CTG GTT CGT CTC TGA CGC CCC CGC TCT 400                          405                          410
Leu Val Val Leu Ala Thr Ala Thr Pro Pro Gly Ser Val Thr Val Pro
CTG GTT GTG CTC GCC ACC GCC ACC CCT CCG GGC TCC GTC ACT GTG CCC
GAC CAA CAC GAG CGG TGG CGG TGG GGA GGC CCG AGG CAG TGA CAC GGG 415                          420                          425                          430
His Pro Asn Ile Glu Glu Val Ala Leu Ser Thr Thr Gly Glu Ile Pro
CAT CCC AAC ATC GAG GAG GTT GCT CTG TCC ACC ACC GGA GAG ATC CCT
GTA GGG TTG TAG CTC CTC CAA CGA GAC AGG TGG TGG CCT CTC TAG GGA 435                          440                          445
Phe Tyr Gly Lys Ala Ile Pro Leu Glu Val Ile Lys Gly Gly Arg His
TTT TAC GGC AAG GCT ATC CCC CTC GAA GTA ATC AAG GGG GGG AGA CAT
AAA ATG CCG TTC CGA TAG GGG GAG CTT CAT TAG TTC CCC CCC TCT GTA 450                          455                          460
Leu Ile Phe Cys His Ser Lys Lys Lys Cys Asp Glu Leu Ala Ala Lys
CTC ATC TTC TGT CAT TCA AAG AAG AAG TGC GAC GAA CTC GCC GCA AAG
GAG TAG AAG ACA GTA AGT TTC TTC TTC ACG CTG CTT GAG CGG CGT TTC 465                          470                          475
Leu Val Ala Leu Gly Ile Asn Ala Val Ala Tyr Tyr Arg Gly Leu Asp
CTG GTC GCA TTG GGC ATC AAT GCC GTG GCC TAC TAC CGC GGT CTT GAC
GAC CAG CGT AAC CCG TAG TTA CGG CAC CGG ATG ATG GCG CCA GAA CTG 480                          485                          490
Val Ser Val Ile Pro Thr Ser Gly Asp Val Val Val Ala Thr Asp
GTG TCC GTC ATC CCG ACC AGC GGC GAT GTT GTC GTC GTG GCA ACC GAT
CAC AGG CAG TAG GGC TGG TCG CCG CTA CAA CAG CAG CAC CGT TGG CTA
```

FIG. 1D

```
     495                      500                       505                      510
Ala Leu Met Thr Gly Tyr Thr Gly Asp Phe Asp Ser Val Ile Asp Cys
GCC CTC ATG ACC GGC TAT ACC GGC GAC TTC GAC TCG GTG ATA GAC TGC
CGG GAG TAC TGG CCG ATA TGG CCG CTG AAG CTG AGC CAC TAT CTG ACG 515                      520                       525
Asn Thr Cys Val Thr Gln Thr Val Asp Phe Ser Leu Asp Pro Thr Phe
AAT ACG TGT GTC ACC CAG ACA GTC GAT TTC AGC CTT GAC CCT ACC TTC
TTA TGC ACA CAG TGG GTC TGT CAG CTA AAG TCG GAA CTG GGA TGG AAG 530                       535                      540
Thr Ile Glu Thr Ile Thr Leu Pro Gln Asp Ala Val Ser Arg Thr Gln
ACC ATT GAG ACA ATC ACG CTC CCC CAA GAT GCT GTC TCC CGC ACT CAA
TGG TAA CTC TGT TAG TGC GAG GGG GTT CTA CGA CAG AGG GCG TGA GTT 545                      550                       555
Arg Arg Gly Arg Thr Gly Arg Gly Lys Pro Gly Ile Tyr Arg Phe Val
CGT CGG GGC AGG ACT GGC AGG GGG AAG CCA GGC ATC TAC AGA TTT GTG
GCA GCC CCG TCC TGA CCG TCC CCC TTC GGT CCG TAG ATG TCT AAA CAC 560                      565                       570
Ala Pro Gly Glu Arg Pro Pro Gly Met Phe Asp Ser Ser Val Leu Cys
GCA CCG GGG GAG CGC CCT CCC GGC ATG TTC GAC TCG TCC GTC CTC TGT
CGT GGC CCC CTC GCG GGA GGG CCG TAC AAG CTG AGC AGG CAG GAG ACA 575                      580                       585                      590
Glu Cys Tyr Asp Ala Gly Cys Ala Trp Tyr Glu Leu Thr Pro Ala Glu
GAG TGC TAT GAC GCA GGC TGT GCT TGG TAT GAG CTC ACG CCC GCC GAG
CTC ACG ATA CTG CGT CCG ACA CGA ACC ATA CTC GAG TGC GGG CGG CTC 595                      600                       605
Thr Thr Val Arg Leu Arg Ala Tyr Met Asn Thr Pro Gly Leu Pro Val
ACT ACA GTT AGG CTA CGA GCG TAC ATG AAC ACC CCG GGG CTT CCC GTG
TGA TGT CAA TCC GAT GCT CGC ATG TAC TTG TGG GGC CCC GAA GGG CAC

FIG. IE
```

```
             610                              615                           620
Cys Gln Asp His Leu Glu Phe Trp Glu Gly Val Phe Thr Gly Leu Thr
TGC CAG GAC CAT CTT GAA TTT TGG GAG GGC GTC TTT ACA GGC CTC ACT
ACG GTC CTG GTA GAA CTT AAA ACC CTC CCG CAG AAA TGT CCG GAG TGA 625                              630                           635
His Ile Asp Ala His Phe Leu Ser Gln Thr Lys Gln Ser Gly Glu Asn
CAT ATA GAT GCC CAC TTT CTA TCC CAG ACA AAG CAG AGT GGG GAG AAC
GTA TAT CTA CGG GTG AAA GAT AGG GTC TGT TTC GTC TCA CCC CTC TTG 640                              645                           650
Leu Pro Tyr Leu Val Ala Tyr Gln Ala Thr Val Cys Ala Arg Ala Gln
CTT CCT TAC CTG GTA GCG TAC CAA GCC ACC GTG TGC GCT AGG GCT CAA
GAA GGA ATG GAC CAT CGC ATG GTT CGG TGG CAC ACG CGA TCC CGA GTT 655                           660                           665                      670
Ala Pro Pro Pro Ser Trp Asp Gln Met Trp Lys Cys Leu Ile Arg Leu
GCC CCT CCC CCA TCG TGG GAC CAG ATG TGG AAG TGT TTG ATT CGC CTC
CGG GGA GGG GGT AGC ACC CTG GTC TAC ACC TTC ACA AAC TAA GCG GAG 675                           680                           685
Lys Pro Thr Leu His Gly Pro Thr Pro Leu Leu Tyr Arg Leu Gly Ala
AAG CCC ACC CTC CAT GGG CCA ACA CCC CTG CTA TAC AGA CTG GGC GCT
TTC GGG TGG GAG GTA CCC GGT TGT GGG GAC GAT ATG TCT GAC CCG CGA
```

```
Asn Ser Glu Asn Gln Val Glu Gly Glu Val Gln Ile Val Ser Thr Ala
AAT TCG GAA AAC CAA GTG GAG GGT GAG GTC CAG ATT GTG TCA ACT GCT
TTA AGC CTT TTG GTT CAC CTC CCA CTC CAG GTC TAA CAC AGT TGA CGA
↑
EcoRI

Ala Gln Thr Phe Leu Ala Thr Cys Ile Asn Gly Val Cys Trp Thr Val
GCC CAA ACC TTC CTG GCA ACG TGC ATC AAT GGG GTG TGC TGG ACT GTC
CGG GTT TGG AAG GAC CGT TGC ACG TAG TTA CCC CAC ACG ACC TGA CAG
                            ↑
                          SfaNI

Tyr His Gly Ala Gly Thr Arg Thr Ile Ala Ser Pro Lys Gly Pro Val
TAC CAC GGG GCC GGA ACG AGG ACC ATC GCG TCA CCC AAG GGT CCT GTC
ATG GTG CCC CGG CCT TGC TCC TGG TAG CGC AGT GGG TTC CCA GGA CAG

Ile Gln Met Tyr Thr Asn Val Asp Gln Asp Leu Val Gly Trp Pro Ala
ATC CAG ATG TAT ACC AAT GTA GAC CAA GAC CTT GTG GGC TGG CCC GCT
TAG GTC TAC ATA TGG TTA CAT CTG GTT CTG GAA CAC CCG ACC GGG CGA

Ser Gln Gly Thr Arg Ser Leu Thr Pro Cys Thr Cys Gly Ser Ser Asp
TCG CAA GGT ACC CGC TCA TTG ACA CCC TGC ACT TGC GGC TCC TCG GAC
AGC GTT CCA TGG GCG AGT AAC TGT GGG ACG TGA ACG CCG AGG AGC CTG

Leu Tyr Leu Val Thr Arg His Ala Asp Val Ile Pro Val Arg Arg Arg
CTT TAC CTG GTC ACG AGG CAC GCC GAT GTC ATT CCC GTG CGC CGG CGG
GAA ATG GAC CAG TGC TCC GTG CGG CTA CAG TAA GGG CAC GCG GCC GCC
                                                            ↑
                                                          NaeI

Gly Asp Ser Arg Gly Ser Leu Val Ser Pro Arg Pro Ile Ser Tyr Leu
GGT GAT AGC AGG GGC AGC CTC GTG TCG CCC CGG CCC ATT TCC TAC TTG
CCA CTA TCG TCC CCG TCG GAG CAC AGC GGG GCC GGG TAA AGG ATG AAC

Lys Gly Ser Ser Gly Gly Pro Leu Pro Asn
AAA GGC TCC TCG GGG GGT CCG CTG CCG AAT TC
TTT CCG AGG AGC CCC CCA GGC GAC GGC TTA AG
                                       ↑
                                     EcoRI
```

```
Glu Phe Gly Gly Leu Leu Leu Cys Pro Ala Ala Ala Val Gly Ile Phe
GAA TTC GGG GGC CTG CTG TTG TGC CCC GCG GCA GCC GTG GGC ATA TTT
CTT AAG CCC CCG GAC GAC AAC ACG GGG CGC CGT CGG CAC CCG TAT AAA
 ↑
EcoRI

Arg Ala Ala Val Cys Thr Arg Gly Val Ala Lys Ala Val Asp Phe Ile
AGG GCC GCG GTG TGC ACC CGT GGA GTG GCT AAG GCG GTG GAC TTT ATC
TCC CGG CGC CAC ACG TGG GCA CCT CAC CGA TTC CGC CAC CTG AAA TAG
                                      ↑
                                    DdeI

Pro Val Glu Asn Leu Glu Thr Thr Met Arg Ser Pro Val Phe Thr Asp
CCT GTG GAG AAC CTA GAG ACA ACC ATG AGG TCC CCG GTG TTC ACG GAT
GGA CAC CTC TTG GAT CTC TGT TGG TAC TCC AGG GGC CAC AAG TGC CTA

Asn Ser Ser Pro Pro Val Val Pro Gln Ser Phe Gln Val Ala His Leu
AAC TCC TCT CCA CCA GTA GTG CCC CAG AGC TTC CAG GTG GCT CAC CTC
TTG AGG AGA GGT GGT CAT CAC GGG GTC TCG AAG GTC CAC CGA GTG GAG
                                               ↑
                                             EcoRII

His Ala Pro Arg Ile
CAT GCT CCC CGA ATT C
GTA CGA GGG GCT TAA G
         ↑
       EcoRI
```

FIG. 3 c8h:

```
Pro Cys Thr Cys Gly Ser Ser Asp Leu Tyr Leu Val Thr Arg His Ala
CCC TGC ACT TGC GGC TCC TCG GAC CTT TAC CTG GTC ACG AGG CAC GCC
GGG ACG TGA ACG CCG AGG AGC CTG GAA ATG GAC CAG TGC TCC GTG CGG

Asp Val Ile Pro Val Arg Arg Arg Gly Asp Ser Arg Gly Ser Leu Leu
GAT GTC ATT CCC GTG CGC CGG CGG GGT GAT AGC AGG GGC AGC CTG CTG
CTA CAG TAA GGG CAC GCG GCC GCC CCA CTA TCG TCC CCG TCG GAC GAC

Ser Pro Arg Pro Ile Ser Tyr Leu Lys Gly Ser Ser Gly Gly Pro Leu
TCG CCC CGG CCC ATT TCC TAC TTG AAA GGC TCC TCG GGG GGT CCG CTG
AGC GGG GCC GGG TAA AGG ATG AAC TTT CCG AGG AGC CCC CCA GGC GAC

Leu Cys Pro Ala Gly His Ala Val Gly Ile Phe Arg Ala Ala Val Cys
TTG TGC CCC GCG GGG CAC GCC GTG GGC ATA TTT AGG GCC GCG GTG TGC
AAC ACG GGG CGC CCC GTG CGG CAC CCG TAT AAA TCC CGG CGC CAC ACG

Thr Arg Gly Val Ala Lys Ala Val Asp Phe Ile Pro Val Glu Asn Leu
ACC CGT GGA GTG GCT AAG GCG GTG GAC TTT ATC CCT GTG GAG AAC CTA
TGG GCA CCT CAC CGA TTC CGC CAC CTG AAA TAG GGA CAC CTC TTG GAT
                         ↑
                        DdeI

Glu Thr Thr Met Arg Ser Pro Val Phe Thr Asp Asn Ser
GAG ACA ACC ATG AGG TCC CCG GTG TTC ACG GAT AAC TCC TC
CTC TGT TGG TAC TCC AGG GGC CAC AAG TGC CTA TTG AGG AG
```

```
     Ile Arg Gly Thr Tyr Val Tyr Asn His Leu Thr Pro Leu Arg Asp Trp
     ATT CGG GGC ACC TAT GTT TAT AAC CAT CTC ACT CCT CTT CGG GAC TGG
     TAA GCC CCG TGG ATA CAA ATA TTG GTA GAG TGA GGA GAA GCC CTG ACC
     ↑
     EcoRI

Ala His Asn Gly Leu Arg Asp Leu Ala Val Ala Val Glu Pro Val Val
     GCG CAC AAC GGC TTG CGA GAT CTG GCC GTG GCT GTA GAG CCA GTC GTC
     CGC GTG TTG CCG AAC GCT CTA GAC CGG CAC CGA CAT CTC GGT CAG CAG

Phe Ser Gln Met Glu Thr Lys Leu Ile Thr Trp Gly Ala Asp Thr Ala
     TTC TCC CAA ATG GAG ACC AAG CTC ATC ACG TGG GGG GCA GAT ACC GCC
     AAG AGG GTT TAC CTC TGG TTC GAG TAG TGC ACC CCC CGT CTA TGG CGG

Ala Cys Gly Asp Ile Ile Asn Gly Leu Pro Val Ser Ala Arg Arg Gly
     GCG TGC GGT GAC ATC ATC AAC GGC TTG CCT GTT TCC GCC CGC AGG GGC
     CGC ACG CCA CTG TAG TAG TTG CCG AAC GGA CAA AGG CGG GCG TCC CCG

Arg Glu Ile Leu Leu Gly Pro Ala Asp Gly Met Val Ser Lys Gly Trp
     CGG GAG ATA CTG CTC GGG CCA GCC GAT GGA ATG GTC TCC AAG GGT TGG
     GCC CTC TAT GAC GAG CCC GGT CGG CTA CCT TAC CAG AGG TTC CCA ACC

Arg Leu Leu Ala Pro Ile Thr Ala Tyr Ala Gln Gln Thr Arg Gly Leu
     AGG TTG CTG GCG CCC ATC ACG GCG TAC GCC CAG CAG ACA AGG GGC CTC
     TCC AAC GAC CGC GGG TAG TGC CGC ATG CGG GTC GTC TGT TCC CCG GAG

Leu Gly Cys Ile Ile Thr Ser Leu Thr Gly Arg Asp Lys Asn Gln Val
     CTA GGG TGC ATA ATC ACC AGC CTA ACT GGC CGG GAC AAA AAC CAA GTG
     GAT CCC ACG TAT TAG TGG TCG GAT TGA CCG GCC CTG TTT TTG GTT CAC

Glu Gly Glu Val Gln Ile Val Ser Thr Ala Ala Gln Thr Phe Leu Ala
     GAG GGT GAG GTC CAG ATT GTG TCA ACT GCT GCC CAA ACC TTC CTG GCA
     CTC CCA CTC CAG GTC TAA CAC AGT TGA CGA CGG GTT TGG AAG GAC CGT

Thr Cys Ile Asn Gly Val Cys Trp Pro Asn
     ACG TGC ATC AAT GGG GTG TGC TGG CCG AAT TC
     TGC ACG TAG TTA CCC CAC ACG ACC GGC TTA AG
         ↑                              ↑
         SfaNI                          EcoRI
```

```
Glu Phe Gly Ser Val Ile Pro Thr Ser Gly Asp Val Val Val Ala
GAA TTC GGG TCC GTC ATC CCG ACC AGC GGC GAT GTT GTC GTC GTC GCA
CTT AAG CCC AGG CAG TAG GGC TGG TCG CCG CTA CAA CAG CAG CAG CGT
    ↑
    EcoRI

Thr Asp Ala Leu Met Thr Gly Tyr Thr Gly Asp Phe Asp Ser Val Ile
ACC GAT GCC CTC ATG ACC GGC TAT ACC GGC GAC TTC GAC TCG GTG ATA
TGG CTA CGG GAG TAC TGG CCG ATA TGG CCG CTG AAG CTG AGC CAC TAT
                                                ↑
                                                HinfI Asp Cys Asn Thr Cys Val Thr Gln Thr Val Asp Phe Ser Leu Asp Pro
GAC TGC AAT ACG TGT GTC ACC CAG ACA GTC GAT TTC AGC CTT GAC CCT
CTG ACG TTA TGC ACA CAG TGG GTC TGT CAG CTA AAG TCG GAA CTG GGA Thr Phe Thr Ile Glu Thr Ile Thr Leu Pro Gln Asp Ala Val Ser Arg
ACC TTC ACC ATT GAG ACA ATC ACG CTC CCC CAA GAT GCT GTC TCC CGC
TGG AAG TGG TAA CTC TGT TAG TGC GAG GGG GTT CTA CGA CAG AGG GCG Thr Gln Arg Arg Gly Arg Thr Gly Arg Gly Lys Pro Gly Ile Tyr Arg
ACT CAA CGT CGG GGC AGG ACT GGC AGG GGG AAG CCA GGC ATC TAC AGA
TGA GTT GCA GCC CCG TCC TGA CCG TCC CCC TTC GGT CCG TAG ATG TCT Phe Val Ala Pro Gly Glu Arg Pro Ser Gly Met Phe Asp Ser Ser Val
TTT GTG GCA CCG GGG GAG CGC CCC TCC GGC ATG TTC GAC TCG TCC GTC
AAA CAC CGT GGC CCC CTC GCG GGG AGG CCG TAC AAG CTG AGC AGG CAG
                        ↑                               ↑
                        BglI                            HinfI Leu Cys Glu Cys Pro Asn
CTC TGT GAG TGC CCG AAT TC
GAG ACA CTC ACG GGC TTA AG
                ↑
                EcoRI
```

```
Ile Arg Ser Ile Glu Thr Ile Thr Leu Pro Gln Asp Ala Val Ser Arg
ATT CGG TCC ATT GAG ACA ATC ACG CTC CCC CAG GAT GCT GTC TCC CGC
TAA GCC AGG TAA CTC TGT TAG TGC GAG GGG GTC CTA CGA CAG AGG GCG
↑
EcoRI

Thr Gln Arg Arg Gly Arg Thr Gly Arg Gly Lys Pro Gly Ile Tyr Arg
ACT CAA CGT CGG GGC AGG ACT GGC AGG GGG AAG CCA GGC ATC TAC AGA
TGA GTT GCA GCC CCG TCC TGA CCG TCC CCC TTC GGT CCG TAG ATG TCT

Phe Val Ala Pro Gly Glu Arg Pro Ser Gly Met Phe Asp Ser Ser Val
TTT GTG GCA CCG GGG GAG CGC CCC TCC GGC ATG TTC GAC TCG TCC GTC
AAA CAC CGT GGC CCC CTC GCG GGG AGG CCG TAC AAG CTG AGC AGG CAG
                            ↑
                           BglI

Leu Cys Glu Cys Tyr Asp Ala Gly Cys Ala Trp Tyr Glu Leu Thr Pro
CTC TGT GAG TGC TAT GAC GCA GGC TGT GCT TGG TAT GAG CTC ACG CCC
GAG ACA CTC ACG ATA CTG CGT CCG ACA CGA ACC ATA CTC GAG TGC GGG

Ala Glu Thr Thr Val Arg Leu Arg Ala Tyr Met Asn Thr Pro Gly Leu
GCC GAG ACT ACA GTT AGG CTA CGA GCG TAC ATG AAC ACC CCG GGG CTT
CGG CTC TGA TGT CAA TCC GAT GCT CGC ATG TAC TTG TGG GGC CCC GAA

Pro Val Cys Gln Asp His Leu Glu Phe Trp Glu Gly Val Phe Thr Gly
CCC GTG TGC CAG GAC CAT CTT GAA TTT TGG GAG GGC GTC TTT ACA GGC
GGG CAC ACG GTC CTG GTA GAA CTT AAA ACC CTC CCG CAG AAA TGT CCG

Leu Thr His Ile Asp Ala His Phe Leu Ser Gln Thr Lys Gln Ser Gly
CTC ACT CAT ATA GAT GCC CAC TTT CTA TCC CAG ACA AAG CAG AGT GGG
GAG TGA GTA TAT CTA CGG GTG AAA GAT AGG GTC TGT TTC GTC TCA CCC

Glu Asn Leu Pro Tyr Leu Val Ala Tyr Gln Ala Thr Val Cys Ala Arg
GAG AAC CTT CCT TAC CTG GTA GCG TAC CAA GCC ACC GTG TGC GCT AGG
CTC TTG GAA GGA ATG GAC CAT CGC ATG GTT CGG TGG CAC ACG CGA TCC

Ala Gln Ala Pro Pro Pro Ser Trp Asp Gln Met Trp Lys Cys Leu Ile
GCT CAA GCC CCT CCC CCA TCG TGG GAC CAG ATG TGG AAG TGT TTG ATT
CGA GTT CGG GGA GGG GGT AGC ACC CTG GTC TAC ACC TTC ACA AAC TAA

Arg Leu Lys Pro Thr Leu His Gly Pro Thr Pro Leu Leu Tyr Arg Leu
CGC CTC AAG CCC ACC CTC CAT GGG CCA ACA CCC CTG CTA TAC AGA CTG
GCG GAG TTC GGG TGG GAG GTA CCC GGT TGT GGG GAC GAT ATG TCT GAC

Gly Ala Ala Glu Phe
GGC GCT GCC GAA TTC
CCG CGA CGG CTT AAG
            ↑
           EcoRI
```

```
Glu Phe Gly Ala Val Asp Phe Ile Pro Val Glu Asn Leu Glu Thr Thr
GAA TTC GGG GCG GTG GAC TTT ATC CCT GTG GAG AAC CTA GAG ACA ACC
CTT AAG CCC CGC CAC CTG AAA TAG GGA CAC CTC TTG GAT CTC TGT TGG
 ↑
EcoRI

Met Arg Ser Pro Val Phe Thr Asp Asn Ser Ser Pro Pro Val Val Pro
ATG AGG TCC CCG GTG TTC ACG GAT AAC TCC TCT CCA CCA GTA GTG CCC
TAC TCC AGG GGC CAC AAG TGC CTA TTG AGG AGA GGT GGT CAT CAC GGG

Gln Ser Phe Gln Val Ala His Leu His Ala Pro Thr Gly Ser Gly Lys
CAG AGC TTC CAG GTG GCT CAC CTC CAT GCT CCC ACA GGC AGC GGC AAA
GTC TCG AAG GTC CAC CGA GTG GAG GTA CGA GGG TGT CCG TCG CCG TTT

Ser Thr Lys Val Pro Ala Ala Tyr Ala Ala Gln Gly Tyr Lys Val Leu
AGC ACC AAG GTC CCG GCT GCA TAT GCA GCT CAG GGC TAT AAG GTG CTA
TCG TGG TTC CAG GGC CGA CGT ATA CGT CGA GTC CCG ATA TTC CAC GAT

Val Leu Asn Pro Ser Val Ala Ala Thr Leu Gly Phe Gly Ala Tyr Met
GTA CTC AAC CCC TCT GTT GCT GCA ACA CTG GGC TTT GGT GCT TAC ATG
CAT GAG TTG GGG AGA CAA CGA CGT TGT GAC CCG AAA CCA CGA ATG TAC

Ser Lys Ala His Gly Ile Asp Pro Asn Ile Arg Thr Gly Val Arg Thr
TCC AAG GCT CAT GGG ATC GAT CCT AAC ATC AGG ACC GGG GTG AGA ACA
AGG TTC CGA GTA CCC TAG CTA GGA TTG TAG TCC TGG CCC CAC TCT TGT

Ile Thr Thr Gly Ser Pro Ile Thr Tyr Ser Thr Tyr Gly Lys Phe Leu
ATT ACC ACT GGC AGC CCC ATC ACG TAC TCC ACC TAC GGC AAG TTC CTT
TAA TGG TGA CCG TCG GGG TAG TGC ATG AGG TGG ATG CCG TTC AAG GAA

Ala Asp Gly Gly Cys Ser Gly Gly Ala Tyr Asp Ile Ile Ile Cys Asp
GCC GAC GGC GGG TGC TCG GGG GGC GCT TAT GAC ATA ATA ATT TGT GAC
CGG CTG CCG CCC ACG AGC CCC CCG CGA ATA CTG TAT TAT TAA ACA CTG

Glu Cys His Ser Thr Asp Ala Thr Ser Ile Leu Gly Ile Gly Thr Val
GAG TGC CAC TCC ACG GAT GCC ACA TCC ATC TTG GGC ATT GGC ACT GTC
CTC ACG GTG AGG TGC CTA CGG TGT AGG TAG AAC CCG TAA CCG TGA CAG
```

FIG. 8A

```
Leu Asp Gln Ala Glu Thr Ala Gly Ala Arg Leu Val Val Leu Ala Thr
CTT GAC CAA GCA GAG ACT GCG GGG GCG AGA CTG GTT GTG CTC GCC ACC
GAA CTG GTT CGT CTC TGA CGC CCC CGC TCT GAC CAA CAC GAG CGG TGG

Ala Thr Pro Pro Gly Ser Val Thr Val Pro His Pro Asn Ile Glu Glu
GCC ACC CCT CCG GGC TCC GTC ACT GTG CCC CAT CCC AAC ATC GAG GAG
CGG TGG GGA GGC CCG AGG CAG TGA CAC GGG GTA GGG TTG TAG CTC CTC

Val Ala Leu Ser Thr Thr Gly Glu Ile Pro Phe Tyr Gly Lys Ala Ile
GTT GCT CTG TCC ACC ACC GGA GAG ATC CCT TTT TAC GGC AAG GCT ATC
CAA CGA GAC AGG TGG TGG CCT CTC TAG GGA AAA ATG CCG TTC CGA TAG

Pro Leu Glu Val Ile Lys Gly Gly Arg His Leu Ile Phe Cys His Ser
CCC CTC GAA GTA ATC AAG GGG GGG AGA CAT CTC ATC TTC TGT CAT TCA
GGG GAG CTT CAT TAG TTC CCC CCC TCT GTA GAG TAG AAG ACA GTA AGT

Lys Lys Lys Cys Asp Glu Leu Ala Ala Lys Leu Val Ala Leu Gly Ile
AAG AAG AAG TGC GAC GAA CTC GCC GCA AAG CTG GTC GCA TTG GGC ATC
TTC TTC TTC ACG CTG CTT GAG CGG CGT TTC GAC CAG CGT AAC CCG TAG

Asn Ala Val Ala Tyr Tyr Arg Gly Leu Asp Val Ser Val Ile Pro Thr
AAT GCC GTG GCC TAC TAC CGC GGT CTT GAC GTG TCC GTC ATC CCG ACC
TTA CGG CAC CGG ATG ATG GCG CCA GAA CTG CAC AGG CAG TAG GGC TGG

Ser Gly Asp Val Val Val Val Ala Thr Asp Ala Leu Met Thr Gly Tyr
AGC GGC GAT GTT GTC GTC GTG GCA ACC GAT GCC CTC ATG ACC GGC TAT
TCG CCG CTA CAA CAG CAG CAC CGT TGG CTA CGG GAG TAC TGG CCG ATA

Thr Gly Asp Phe Asp Ser Val Ile Asp Cys Asn Thr Cys Ala Glu Phe
ACC GGC GAC TTC GAC TCG GTG ATA GAC TGC AAT ACG TGT GCC GAA TTC
TGG CCG CTG AAG CTG AGC CAC TAT CTG ACG TTA TGC ACA CGG CTT AAG
            ↑                                           ↑
         HinfI                                        EcoRI
```

FIG. 8B

```
                                    -155                 -150
                               Met Ala Thr Asn Pro Val Cys Val Leu
                               ATG GCT ACA AAC CCT GTT TGC GTT TTG
                               TAC CGA TGT TTG GGA CAA ACG CAA AAC

-145                 -140                 -135
   Lys Gly Asp Gly Pro Val Gln Gly Ile Ile Asn Phe Glu Gln Lys Glu
   AAG GGT GAC GGC CCA GTT CAA GGT ATT ATT AAC TTC GAG CAG AAG GAA
   TTC CCA CTG CCG GGT CAA GTT CCA TAA TAA TTG AAG CTC GTC TTC CTT

-130                 -125                 -120                 -115
   Ser Asn Gly Pro Val Lys Val Trp Gly Ser Ile Lys Gly Leu Thr Glu
   AGT AAT GGA CCA GTG AAG GTG TGG GGA AGC ATT AAA GGA CTG ACT GAA
   TCA TTA CCT GGT CAC TTC CAC ACC CCT TCG TAA TTT CCT GAC TGA CTT

-110                 -105                 -100
   Gly Leu His Gly Phe His Val His Glu Phe Gly Asp Asn Thr Ala Gly
   GGC CTG CAT GGA TTC CAT GTT CAT GAG TTT GGA GAT AAT ACA GCA GGC
   CCG GAC GTA CCT AAG GTA CAA GTA CTC AAA CCT CTA TTA TGT CGT CCG

-95                  -90                  -85
   Cys Thr Ser Pro Gly Pro His Phe Asn Pro Leu Ser Arg Lys His Gly
   TGT ACC AGT CCA GGT CCT CAC TTT AAT CCT CTA TCC AGA AAA CAC GGT
   ACA TGG TCA GGT CCA GGA GTG AAA TTA GGA GAT AGG TCT TTT GTG CCA

-80                  -75                  -70
   Gly Pro Lys Asp Glu Glu Arg His Val Gly Asp Leu Gly Asn Val Thr
   GGG CCA AAG GAT GAA GAG AGG CAT GTT GGA GAC TTG GGC AAT GTG ACT
   CCC GGT TTC CTA CTT CTC TCC GTA CAA CCT CTG AAC CCG TTA CAC TGA

-65                  -60                  -55
   Ala Asp Lys Asp Gly Val Ala Asp Val Ser Ile Glu Asp Ser Val Ile
   GCT GAC AAA GAT GGT GTG GCC GAT GTG TCT ATT GAA GAT TCT GTG ATC
   CGA CTG TTT CTA CCA CAC CGG CTA CAC AGA TAA CTT CTA AGA CAC TAG

-50                  -45                  -40                  -35
   Ser Leu Ser Gly Asp His Cys Ile Ile Gly Arg Thr Leu Val Val His
   TCA CTC TCA GGA GAC CAT TGC ATC ATT GGC CGC ACA CTG GTG GTC CAT
   AGT GAG AGT CCT CTG GTA ACG TAG TAA CCG GCG TGT GAC CAC CAG GTA

-30                  -25                  -20
   Glu Lys Ala Asp Asp Leu Gly Lys Gly Gly Asn Glu Glu Ser Thr Lys
   GAA AAA GCA GAT GAC TTG GGC AAA GGT GGA AAT GAA GAA AGT ACA AAG
   CTT TTT CGT CTA CTG AAC CCG TTT CCA CCT TTA CTT CTT TCA TGT TTC

-15                  -10                  -5
   Thr Gly Asn Ala Gly Ser Arg Leu Ala Cys Gly Val Ile Gly Ile Arg
   ACA GGA AAC GCT GGA AGT CGT TTG GCT TGT GGT GTA ATT GGG ATC CGA
   TGT CCT TTG CGA CCT TCA GCA AAC CGA ACA CCA CAT TAA CCC TAG GCT
```

FIG. 10A

```
           1                     5                          10
Arg Ile Gly Thr Tyr Val Tyr Asn His Leu Thr Pro Leu Arg Asp Trp
ATT CGG GGC ACC TAT GTT TAT AAC CAT CTC ACT CCT CTT CGG GAC TGG
TAA GCC CCG TGG ATA CAA ATA TTG GTA GAG TGA GGA GAA GCC CTG ACC 15                      20                       25               30
Ala His Asn Gly Leu Arg Asp Leu Ala Val Ala Val Glu Pro Val Val
GCG CAC AAC GGC TTG CGA GAT CTG GCC GTG GCT GTA GAG CCA GTC GTC
CGC GTG TTG CCG AAC GCT CTA GAC CGG CAC CGA CAT CTC GGT CAG CAG 35                      40                      45
Phe Ser Gln Met Glu Thr Lys Leu Ile Thr Trp Gly Ala Asp Thr Ala
TTC TCC CAA ATG GAG ACC AAG CTC ATC ACG TGG GGG GCA GAT ACC GCC
AAG AGG GTT TAC CTC TGG TTC GAG TAG TGC ACC CCC CGT CTA TGG CGG 50                      55                      60
Ala Cys Gly Asp Ile Ile Asn Gly Leu Pro Val Ser Ala Arg Arg Gly
GCG TGC GGT GAC ATC ATC AAC GGC TTG CCT GTT TCC GCC CGC AGG GGC
CGC ACG CCA CTG TAG TAG TTG CCG AAC GGA CAA AGG CGG GCG TCC CCG 65                      70                      75
Arg Glu Ile Leu Leu Gly Pro Ala Asp Gly Met Val Ser Lys Gly Trp
CGG GAG ATA CTG CTC GGG CCA GCC GAT GGA ATG GTC TCC AAG GGT TGG
GCC CTC TAT GAC GAG CCC GGT CGG CTA CCT TAC CAG AGG TTC CCA ACC 80                      85                      90
Arg Leu Leu Ala Pro Ile Thr Ala Tyr Ala Gln Gln Thr Arg Gly Leu
AGG TTG CTG GCG CCC ATC ACG GCG TAC GCC CAG CAG ACA AGG GGC CTC
TCC AAC GAC CGC GGG TAG TGC CGC ATG CGG GTC GTC TGT TCC CCG GAG 95                      100                     105                110
Leu Gly Cys Ile Ile Thr Ser Leu Thr Gly Arg Asp Lys Asn Gln Val
CTA GGG TGC ATA ATC ACC AGC CTA ACT GGC CGG GAC AAA AAC CAA GTG
GAT CCC ACG TAT TAG TGG TCG GAT TGA CCG GCC CTG TTT TTG GTT CAC 115                     120                     125
Glu Gly Glu Val Gln Ile Val Ser Thr Ala Ala Gln Thr Phe Leu Ala
GAG GGT GAG GTC CAG ATT GTG TCA ACT GCT GCC CAA ACC TTC CTG GCA
CTC CCA CTC CAG GTC TAA CAC AGT TGA CGA CGG GTT TGG AAG GAC CGT
```

FIG. 10B

```
                130                           135                           140
Thr Cys Ile Ile Asn Gly Val Cys Trp Thr Val Tyr His Gly Ala Gly
ACG TGC ATC ATC AAT GGG GTG TGC TGG ACT GTC TAC CAC GGG GCC GGA
TGC ACG TAG TAG TTA CCC CAC ACG ACC TGA CAG ATG GTG CCC CGG CCT 145                           150                           155
Thr Arg Thr Ile Ala Ser Pro Lys Gly Pro Val Ile Gln Met Tyr Thr
ACG AGG ACC ATC GCG TCA CCC AAG GGT CCT GTC ATC CAG ATG TAT ACC
TGC TCC TGG TAG CGC AGT GGG TTC CCA GGA CAG TAG GTC TAC ATA TGG 160                           165                           170
Asn Val Asp Gln Asp Leu Val Gly Trp Pro Ala Ser Gln Gly Thr Arg
AAT GTA GAC CAA GAC CTT GTG GGC TGG CCC GCT TCG CAA GGT ACC CGC
TTA CAT CTG GTT CTG GAA CAC CCG ACC GGG CGA AGT GTT CCA TGG GCG 175                           180                           185                   190
Ser Leu Thr Pro Cys Thr Cys Gly Ser Ser Asp Leu Tyr Leu Val Thr
TCA TTG ACA CCC TGC ACT TGC GGC TCC TCG GAC CTT TAC CTG GTC ACG
AGT AAC TGT GGG ACG TGA ACG CCG AGG AGC CTG GAA ATG GAC CAG TGC 195                           200                           205
Arg His Ala Asp Val Ile Pro Val Arg Arg Arg Gly Asp Ser Arg Gly
AGG CAC GCC GAT GTC ATT CCC GTG CGC CGG CGG GGT GAT AGC AGG GGC
TCC GTG CGG CTA CAG TAA GGG CAC GCG GCC GCC CCA CTA TCG TCC CCG
                                ↑
                              NaeI 210                           215                           220
Ser Leu Leu Ser Pro Arg Pro Ile Ser Tyr Leu Lys Gly Ser Ser Gly
AGC CTG CTG TCG CCC CGG CCC ATT TCC TAC TTG AAA GGC TCC TCG GGG
TCG GAC GAC AGC GGG GCC GGG TAA AGG ATG AAC TTT CCG AGG AGC CCC 225                           230                           235
Gly Pro Leu Leu Cys Pro Ala Gly His Ala Val Gly Ile Phe Arg Ala
GGT CCG CTG TTG TGC CCC GCG GGG CAC GCC GTG GGC ATA TTT AGG GCC
CCA GGC GAC AAC ACG GGG CGC CCC GTG CGG CAC CCG TAT AAA TCC CGG 240                           245                           250
Ala Val Cys Thr Arg Gly Val Ala Lys Ala Val Asp Phe Ile Pro Val
GCG GTG TGC ACC CGT GGA GTG GCT AAG GCG GTG GAC TTT ATC CCT GTG
CGC CAC ACG TGG GCA CCT CAC CGA TTC CGC CAC CTG AAA TAG GGA CAC
```

FIG. 10C

```
      255                          260                          265                          270
Glu  Asn  Leu  Glu  Thr  Thr  Met  Arg  Ser  Pro  Val  Phe  Thr  Asp  Asn  Ser
GAG  AAC  CTA  GAG  ACA  ACC  ATG  AGG  TCC  CCG  GTG  TTC  ACG  GAT  AAC  TCC
CTC  TTG  GAT  CTC  TGT  TGG  TAC  TCC  AGG  GGC  CAC  AAG  TGC  CTA  TTG  AGG 275                          280                          285
Ser  Pro  Pro  Val  Val  Pro  Gln  Ser  Phe  Gln  Val  Ala  His  Leu  His  Ala
TCT  CCA  CCA  GTA  GTG  CCC  CAG  AGC  TTC  CAG  GTG  GCT  CAC  CTC  CAT  GCT
AGA  GGT  GGT  CAT  CAC  GGG  GTC  TCG  AAG  GTC  CAC  CGA  GTG  GAG  GTA  CGA 290                          295                          300
Pro  Thr  Gly  Ser  Gly  Lys  Ser  Thr  Lys  Val  Pro  Ala  Ala  Tyr  Ala  Ala
CCC  ACA  GGC  AGC  GGC  AAA  AGC  ACC  AAG  GTC  CCG  GCT  GCA  TAT  GCA  GCT
GGG  TGT  CCG  TCG  CCG  TTT  TCG  TGG  TTC  CAG  GGC  CGA  CGT  ATA  CGT  CGA
                                                                ↑
                                                              NdeI 305                          310                          315
Gln  Gly  Tyr  Lys  Val  Leu  Val  Leu  Asn  Pro  Ser  Val  Ala  Ala  Thr  Leu
CAG  GGC  TAT  AAG  GTG  CTA  GTA  CTC  AAC  CCC  TCT  GTT  GCT  GCA  ACA  CTG
GTC  CCG  ATA  TTC  CAC  GAT  CAT  GAG  TTG  GGG  AGA  CAA  CGA  CGT  TGT  GAC 320                          325                          330
Gly  Phe  Gly  Ala  Tyr  Met  Ser  Lys  Ala  His  Gly  Ile  Asp  Pro  Asn  Ile
GGC  TTT  GGT  GCT  TAC  ATG  TCC  AAG  GCT  CAT  GGG  ATC  GAT  CCT  AAC  ATC
CCG  AAA  CCA  CGA  ATG  TAC  AGG  TTC  CGA  GTA  CCC  TAG  CTA  GGA  TTG  TAG 335                          340                          345                          350
Arg  Thr  Gly  Val  Arg  Thr  Ile  Thr  Thr  Gly  Ser  Pro  Ile  Thr  Tyr  Ser
AGG  ACC  GGG  GTG  AGA  ACA  ATT  ACC  ACT  GGC  AGC  CCC  ATC  ACG  TAC  TCC
TCC  TGG  CCC  CAC  TCT  TGT  TAA  TGG  TGA  CCG  TCG  GGG  TAG  TGC  ATG  AGG 355                          360                          365
Thr  Tyr  Gly  Lys  Phe  Leu  Ala  Asp  Gly  Gly  Cys  Ser  Gly  Gly  Ala  Tyr
ACC  TAC  GGC  AAG  TTC  CTT  GCC  GAC  GGC  GGG  TGC  TCG  GGG  GGC  GCT  TAT
TGG  ATG  CCG  TTC  AAG  GAA  CGG  CTG  CCG  CCC  ACG  AGC  CCC  CCG  CGA  ATA 370                          375                          380
Asp  Ile  Ile  Ile  Cys  Asp  Glu  Cys  His  Ser  Thr  Asp  Ala  Thr  Ser  Ile
GAC  ATA  ATA  ATT  TGT  GAC  GAG  TGC  CAC  TCC  ACG  GAT  GCC  ACA  TCC  ATC
CTG  TAT  TAT  TAA  ACA  CTG  CTC  ACG  GTG  AGG  TGC  CTA  CGG  TGT  AGG  TAG
```

FIG. 10D

```
             385                    390                    395
Leu Gly Ile Gly Thr Val Leu Asp Gln Ala Glu Thr Ala Gly Ala Arg
TTG GGC ATT GGC ACT GTC CTT GAC CAA GCA GAG ACT GCG GGG GCG AGA
AAC CCG TAA CCG TGA CAG GAA CTG GTT CGT CTC TGA CGC CCC CGC TCT 400                    405                    410
Leu Val Val Leu Ala Thr Ala Thr Pro Pro Gly Ser Val Thr Val Pro
CTG GTT GTG CTC GCC ACC GCC ACC CCT CCG GGC TCC GTC ACT GTG CCC
GAC CAA CAC GAG CGG TGG CGG TGG GGA GGC CCG AGG CAG TGA CAC GGG 415                    420                    425                430
His Pro Asn Ile Glu Glu Val Ala Leu Ser Thr Thr Gly Glu Ile Pro
CAT CCC AAC ATC GAG GAG GTT GCT CTG TCC ACC ACC GGA GAG ATC CCT
GTA GGG TTG TAG CTC CTC CAA CGA GAC AGG TGG TGG CCT CTC TAG GGA 435                    440                    445
Phe Tyr Gly Lys Ala Ile Pro Leu Glu Val Ile Lys Gly Gly Arg His
TTT TAC GGC AAG GCT ATC CCC CTC GAA GTA ATC AAG GGG GGG AGA CAT
AAA ATG CCG TTC CGA TAG GGG GAG CTT CAT TAG TTC CCC CCC TCT GTA 450                    455                    460
Leu Ile Phe Cys His Ser Lys Lys Lys Cys Asp Glu Leu Ala Ala Lys
CTC ATC TTC TGT CAT TCA AAG AAG AAG TGC GAC GAA CTC GCC GCA AAG
GAG TAG AAG ACA GTA AGT TTC TTC TTC ACG CTG CTT GAG CGG CGT TTC 465                    470                    475
Leu Val Ala Leu Gly Ile Asn Ala Val Ala Tyr Tyr Arg Gly Leu Asp
CTG GTC GCA TTG GGC ATC AAT GCC GTG GCC TAC TAC CGC GGT CTT GAC
GAC CAG CGT AAC CCG TAG TTA CGG CAC CGG ATG ATG GCG CCA GAA CTG 480                    485                    490
Val Ser Val Ile Pro Thr Ser Gly Asp Val Val Val Ala Thr Asp
GTG TCC GTC ATC CCG ACC AGC GGC GAT GTT GTC GTC GTG GCA ACC GAT
CAC AGG CAG TAG GGC TGG TCG CCG CTA CAA CAG CAG CAC CGT TGG CTA
```

FIG. 1OE

```
      495                      500                     505                    510
Ala Leu Met Thr Gly Tyr Thr Gly Asp Phe Asp Ser Val Ile Asp Cys
GCC CTC ATG ACC GGC TAT ACC GGC GAC TTC GAC TCG GTG ATA GAC TGC
CGG GAG TAC TGG CCG ATA TGG CCG CTG AAG CTG AGC CAC TAT CTG ACG 515                     520                    525
Asn Thr Cys Val Thr Gln Thr Val Asp Phe Ser Leu Asp Pro Thr Phe
AAT ACG TGT GTC ACC CAG ACA GTC GAT TTC AGC CTT GAC CCT ACC TTC
TTA TGC ACA CAG TGG GTC TGT CAG CTA AAG TCG GAA CTG GGA TGG AAG 530                    535                  540
Thr Ile Glu Thr Ile Thr Leu Pro Gln Asp Ala Val Ser Arg Thr Gln
ACC ATT GAG ACA ATC ACG CTC CCC CAA GAT GCT GTC TCC CGC ACT CAA
TGG TAA CTC TGT TAG TGC GAG GGG GTT CTA CGA CAG AGG GCG TGA GTT 545                    550                    555
Arg Arg Gly Arg Thr Gly Arg Gly Lys Pro Gly Ile Tyr Arg Phe Val
CGT CGG GGC AGG ACT GGC AGG GGG AAG CCA GGC ATC TAC AGA TTT GTG
GCA GCC CCG TCC TGA CCG TCC CCC TTC GGT CCG TAG ATG TCT AAA CAC 560                    565                  570
Ala Pro Gly Glu Arg Pro Pro Gly Met Phe Asp Ser Ser Val Leu Cys
GCA CCG GGG GAG CGC CCT CCC GGC ATG TTC GAC TCG TCC GTC CTC TGT
CGT GGC CCC CTC GCG GGA GGG CCG TAC AAG CTG AGC AGG CAG GAG ACA 575                   580                   585                 590
Glu Cys Tyr Asp Ala Gly Cys Ala Trp Tyr Glu Leu Thr Pro Ala Glu
GAG TGC TAT GAC GCA GGC TGT GCT TGG TAT GAG CTC ACG CCC GCC GAG
CTC ACG ATA CTG CGT CCG ACA CGA ACC ATA CTC GAG TGC GGG CGG CTC 595                   600                 605
Thr Thr Val Arg Leu Arg Ala Tyr Met Asn Thr Pro Gly Leu Pro Val
ACT ACA GTT AGG CTA CGA GCG TAC ATG AAC ACC CCG GGG CTT CCC GTG
TGA TGT CAA TCC GAT GCT CGC ATG TAC TTG TGG GGC CCC GAA GGG CAC
```

FIG. 1 OF

```
              610                    615                    620
Cys Gln Asp His Leu Glu Phe Trp Glu Gly Val Phe Thr Gly Leu Thr
TGC CAG GAC CAT CTT GAA TTT TGG GAG GGC GTC TTT ACA GGC CTC ACT
ACG GTC CTG GTA GAA CTT AAA ACC CTC CCG CAG AAA TGT CCG GAG TGA 625                    630                    635
His Ile Asp Ala His Phe Leu Ser Gln Thr Lys Gln Ser Gly Glu Asn
CAT ATA GAT GCC CAC TTT CTA TCC CAG ACA AAG CAG AGT GGG GAG AAC
GTA TAT CTA CGG GTG AAA GAT AGG GTC TGT TTC GTC TCA CCC CTC TTG 640                    645                    650
Leu Pro Tyr Leu Val Ala Tyr Gln Ala Thr Val Cys Ala Arg Ala Gln
CTT CCT TAC CTG GTA GCG TAC CAA GCC ACC GTG TGC GCT AGG GCT CAA
GAA GGA ATG GAC CAT CGC ATG GTT CGG TGG CAC ACG CGA TCC CGA GTT 655                 660                    665                    670
Ala Pro Pro Pro Ser Trp Asp Gln Met Trp Lys Cys Leu Ile Arg Leu
GCC CCT CCC CCA TCG TGG GAC CAG ATG TGG AAG TGT TTG ATT CGC CTC
CGG GGA GGG GGT AGC ACC CTG GTC TAC ACC TTC ACA AAC TAA GCG GAG 675                    680                    685
Lys Pro Thr Leu His Gly Pro Thr Pro Leu Leu Tyr Arg Leu Gly Ala
AAG CCC ACC CTC CAT GGG CCA ACA CCC CTG CTA TAC AGA CTG GGC GCT
TTC GGG TGG GAG GTA CCC GGT TGT GGG GAC GAT ATG TCT GAC CCG CGA
```

FIG. 1OG

HEPATITIS C VIRUS PROTEASE

CROSS-REFERENCE TO RELATED APPLICATIONS

This application is a continuation, of application Ser. No. 08/440,548, filed May 12, 1995, now issued as U.S. Pat. No. 5,597,691, which is a divisional of U.S. Ser. No. 08/350,884, filed Dec. 6, 1994, now U.S. Pat. No. 5,585,258, which is a divisional of U.S. Ser. No. 07/680,296, filed Apr. 4, 1991, now U.S. Pat. No. 5,371,017, which is a continuation-in-part of U.S. Ser. No. 07/505,433, filed 4 Apr. 1990, abandoned.

TECHNICAL FIELD

This invention relates to the molecular biology and virology of the hepatitis C virus (HCV). More specifically, this invention relates to a novel protease produced by HCV, methods of expression, recombinant protease, protease mutants, and inhibitors of HCV protease.

BACKGROUND OF THE INVENTION

Non-A, Non-B hepatitis (NANBH) is a transmissible disease (or family of diseases) that is believed to be virally induced, and is distinguishable from other forms of virus-associated liver disease, such as those caused by hepatitis A virus (HAV), hepatitis B virus (HBV), delta hepatitis virus (HDV), cytomegalovirus (CMV) or Epstein-Barr virus (EBV). Epidemiologic evidence suggests that there may be three types of NANBH: the water-bome epidemic type; he blood or needle associated type; and the sporadically occurring (community acquired) type. However, the number of causative agents is unknown. Recently, however, a new viral species, hepatitis C virus (HCV) has been identified as the primary (if not only) cause of blood-associated NANBH (BB-NANBH). See for example, PCT WO89/046699; U.S. patent application Ser. No. 7/456,637, filed 21 Dec. 1989; and U.S. patent application Ser. No. 7/456,637, filed 21 Dec. 1989, incorporated herein by reference. Hepatitis C appears to be the major form of transfusion-associated hepatitis in a number of countries, including the United States and Japan. There is also evidence implicating HCV in induction of hepatocellular carcinoma. Thus, a need exists for an effective method for treating HCV infection: currently, there is none.

Many viruses, including adenoviruses, baculoviruses, comoviruses, picomaviruses, retroviruses, and togaviruses, rely on specific, virally-encoded proteases for processing polypeptides from their initial translated form into mature, active proteins. In the case of picomaviruses, all of the viral proteins are believed to arise from cleavage of a single polyprotein (B. D. Korant, *CRC Crit Rev Biotech* (1988) 8:149–57).

S. Pichuantes et al, in "Viral Proteinases As Targets For Chemotherapy" (Cold Spring Harbor Laboratory Press, 1989) pp. 215–22, disclosed expression of a viral protease found in HIV-1. The HIV protease was obtained in the form of a fusion protein, by fusing DNA encoding an HIV protease precursor to DNA encoding human superoxide dismutase (hSOD), and expressing the product in *E. coli*. Transformed cells expressed products of 36 and 10 kDa (corresponding to the hSOD-protease fusion protein and the protease alone), suggesting that the protease was expressed in a form capable of autocatalytic proteolysis.

T. J. McQuade et al, *Science* (1990) 247:454–56 disclosed preparation of a peptide mimic capable of specifically inhibiting the HIV-1 protease. In HIV, the protease is believed responsible for cleavage of the initial p55 gag precursor transcript into the core structural proteins (p17, p24, p8, and p7). Adding 1 µM inhibitor to HIV-infected peripheral blood lymphocytes in culture reduced the concentration of processed HIV p24 by about 70%. Viral maturation and levels of infectious virus were reduced by the protease inhibitor.

DISCLOSURE OF THE INVENTION

We have now invented recombinant HCV protease, HCV protease fusion proteins, truncated and altered HCV proteases, cloning and expression vectors therefore, and methods for identifying antiviral agents effective for treating HCV.

BRIEF DESCRIPTION OF THE DRAWINGS

FIG. 1 shows the sequence of HCV protease (SEQ ID NO: 69 and SEQ ID NO: 70).

FIG. 2 shows the polynucleotide sequence and deduced amino acid sequence of the clone C20c (SEQ ID NO: 71 and SEQ ID NO: 72).

FIG. 3 shows the polynucleotide sequence and deduced amino acid sequence of the clone C26d (SEQ ID NO: 73 and SEQ ID NO: 74).

FIG. 4 shows the polynucleotide sequence and deduced amino acid sequence of the clone C8h (SEQ ID NO: 75 and SEQ ID NO: 76).

FIG. 5 shows the polynucleotide sequence and deduced amino acid sequence of the clone C7f (SEQ ID NO: 77 and SEQ ID NO: 78).

FIG. 6 shows the polynucleotide sequence and deduced amino acid sequence of the clone C31 (SEQ ID NO: 79 and SEQ ID NO: 80).

FIG. 7 shows the polynucleotide sequence and deduced amino acid sequence of the clone C35 (SEQ ID NO: 81 and SEQ ID NO: 82).

FIG. 8 shows the polynucleotide sequence and deduced amino acid sequence of the clone C33c (SEQ ID NO: 83 and SEQ ID NO: 84).

FIG. 10 shows the sequence of vector cflSODp600.

MODES OF CARRYING OUT THE INVENTION

A. Definitions

Figure 9A:
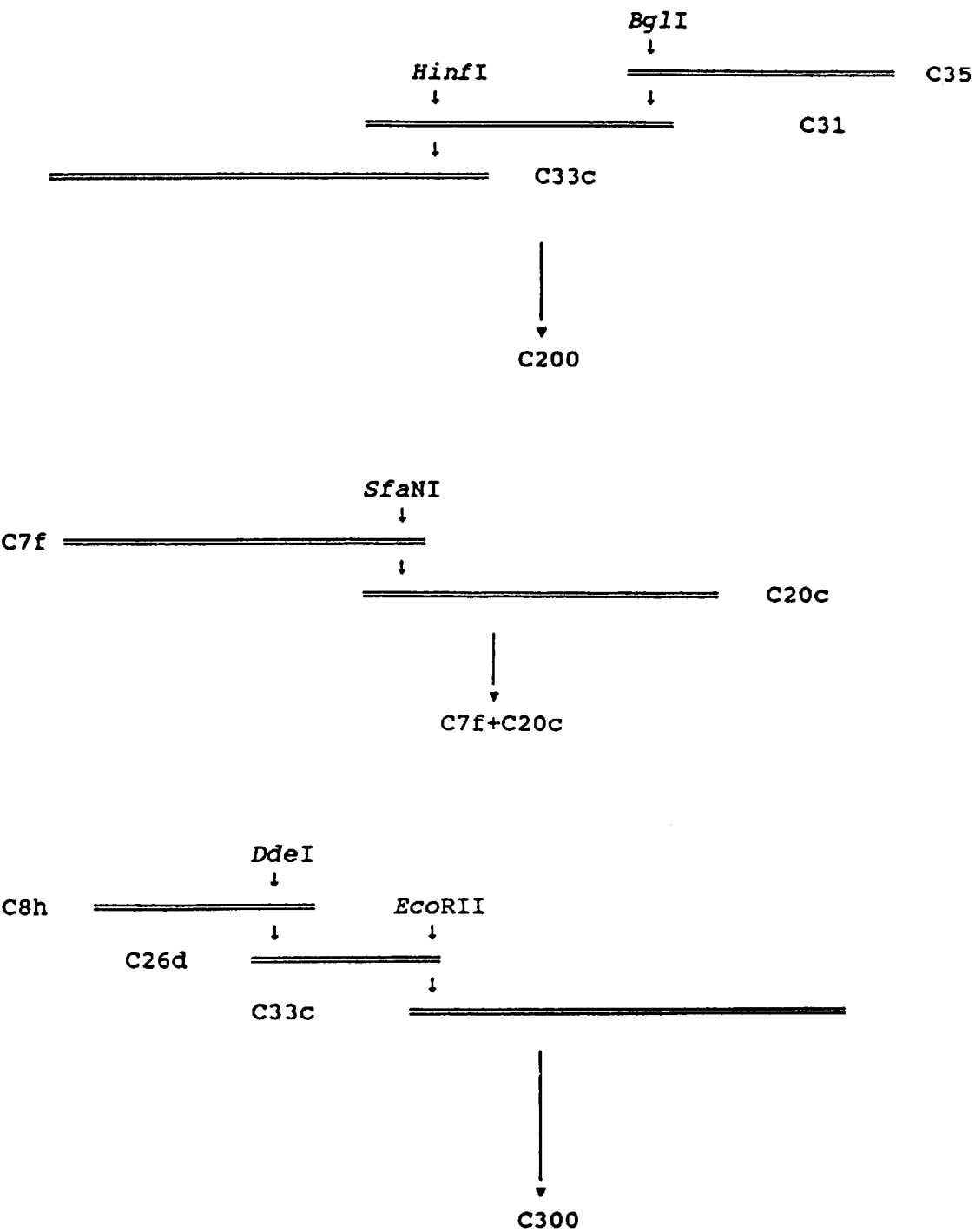
FIG. 9 schematically illustrates assembly of the vector C7fC20cC300C200 (SEQ ID NO: 85 and SEQ ID NO: 86).

The terms "Hepatitis C Virus" and "HCV" refer to the viral species that is the major etiological agent of BB-NANBH, the prototype isolate of which is identified in PCT WO89/046699; EPO publication 318,216; U.S. Ser. No. 7/355,008, filed 18 May 1989; and U.S. Ser. No. 7/456,637, the disclosures of which are incorporated herein by reference. "HCV" as used herein includes the pathogenic strains capable of causing hepatitis C, and attenuated strains or defective interfering particles derived therefrom. The HCV genome is comprised of RNA. It is known that RNA-containing viruses have relatively high rates of spontaneous mutation, reportedly on the order of $10^{-3}$ to $10^{-4}$ per incorporated nucleotide (Fields & Knipe, "Fundamental Virology" (1986, Raven Press, N.Y.)). As heterogeneity and fluidity of genotype are inherent characteristics of RNA viruses, there will be multiple strains/isolates, which may be virulent or avirulent, within the HCV species.

Information on several different strains/isolates of HCV is disclosed herein, particularly strain or isolate CDC/HCVI (also called HCV1). Information from one strain or isolate, such as a partial genomic sequence, is sufficient to allow those skilled in the art using standard techniques to isolate new strains/isolates and to identify whether such new strains/isolates are HCV. For example, several different strains/isolates are described below. These strains, which were obtained from a number of human sera (and from different geographical areas), were isolated utilizing the information from the genomic sequence of HCV1.

The information provided herein suggests that HCV may be distantly related to the flaviviridae. The Flavivirus family contains a large number of viruses which are small, enveloped pathogens of man. The morphology and composition of Flavivirus particles are known, and are discussed in M. A. Brinton, in "The Viruses: The Togaviridae And Flaviviridae" (Series eds. Fraenkel-Conrat and Wagner, vol. eds. Schlesinger and Schlesinger, Plenum Press, 1986), pp. 327–374. Generally, with respect to morphology, Flaviviruses contain a central nucleocapsid surrounded by a lipid bilayer. Virions are spherical and have a diameter of about 40–50 nm. Their cores are about 25–30 nm in diameter. Along the outer surface of the virion envelope are projections measuring about 5–10 nm in length with terminal knobs about 2 nm in diameter. Typical examples of the family include Yellow Fever virus, West Nile virus, and Dengue Fever virus. They possess positive-stranded RNA genomes (about 11,000 nucleotides) that are slightly larger than that of HCV and encode a polyprotein precursor of about 3500 amino acids. Individual viral proteins are cleaved from this precursor polypeptide.

The genome of HCV appears to be single-stranded RNA containing about 10,000 nucleotides. The genome is positive-stranded, and possesses a continuous translational open reading frame (ORF) that encodes a polyprotein of about 3,000 amino acids. In the ORF, the structural proteins appear to be encoded in approximately the first quarter of the N-terminal region, with the majority of the polyprotein attributed to non-structural proteins. When compared with all known viral sequences, small but significant co-linear homologies are observed with the non-structural proteins of the Flavivirus family, and with the pestiviruses (which are now also considered to be part of the Flavivirus family).

A schematic alignment of possible regions of a flaviviral polyprotein (using Yellow Fever Virus as an example), and of a putative polyprotein encoded in the major ORF of the HCV genome, is shown in FIG. 1. Possible domains of the HCV polyprotein are indicated in the figure. The Yellow Fever Virus polyprotein contains, from the amino terminus to the carboxy terminus, the nucleocapsid protein (C), the matrix protein (M), the envelope protein (E), and the non-structural proteins 1, 2 (a+b), 3, 4 (a+b), and 5 (NS1, NS2, NS3, NS4, and NS5). Based upon the putative amino acids encoded in the nucleotide sequence of HCV1, a small domain at the extreme N-terminus of the HCV polyprotein appears similar both in size and high content of basic residues to the nucleocapsid protein (C) found at the N-terminus of flaviviral polyproteins. The non-structural proteins 2,3,4, and 5 (NS2–5) of HCV and of yellow fever virus (YFV) appear to have counterparts of similar size and hydropathicity, although the amino acid sequences diverge. However, the region of HCV which would correspond to the regions of YFV polyprotein which contains the M, E, and NS1 protein not only differs in sequence, but also appears to be quite different in size and hydropathicity. Thus, while certain domains of the HCV genome may be referred to herein as, for example, NS1, or NS2, it should be understood that these designations are for convenience of reference only; there may be considerable differences between the HCV family and flaviviruses that have yet to be appreciated.

Due to the evolutionary relationship of the strains or isolates of HCV, putative HCV strains and isolates are identifiable by their homology at the polypeptide level. With respect to the isolates disclosed herein, new HCV strains or isolates are expected to be at least about 40% homologous, some more than about 70% homologous, and some even more than about 80% homologous: some may be more than about 90% homologous at the polypeptide level. The techniques for determining amino acid sequence homology are known in the art. For example, the amino acid sequence may be determined directly and compared to the sequences provided herein. Alternatively the nucleotide sequence of the genomic material of the putative HCV may be determined (usually via a cDNA intermediate), the amino acid sequence encoded therein can be determined, and the corresponding regions compared.

The term "HCV protease" refers to an enzyme derived from HCV which exhibits proteolytic activity, specifically the polypeptide encoded in the NS3 domain of the HCV genome. At least one strain of HCV contains a protease believed to be substantially encoded by or within the following sequence:

| | | | | | | | | | | |
|---|---|---|---|---|---|---|---|---|---|---|
| Arg | Arg | Gly | Arg | Glu | Ile | Leu | Leu | Gly | Pro | 10 |
| Ala | Asp | Gly | Met | Val | Ser | Lys | Gly | Trp | Arg | 20 |
| Leu | Leu | Ala | Pro | Ile | Thr | Ala | Tyr | Ala | Gln | 30 |
| Gln | Thr | Arg | Gly | Leu | Leu | Gly | Cys | Ile | Ile | 40 |
| Thr | Ser | Leu | Thr | Gly | Arg | Asp | Lys | Asn | Gln | 50 |
| Val | Glu | Gly | Glu | Val | Gln | Ile | Val | Ser | Thr | 60 |
| Ala | Ala | Gln | Thr | Phe | Leu | Ala | Thr | Cys | Ile | 70 |
| Asn | Gly | Val | Cys | Trp | Thr | Val | Tyr | His | Gly | 80 |
| Ala | Gly | Thr | Arg | Thr | Ile | Ala | Ser | Pro | Lys | 90 |
| Gly | Pro | Val | Ile | Gln | Met | Tyr | Thr | Asn | Val | 100 |
| Asp | Gln | Asp | Leu | Val | Gly | Trp | Pro | Ala | Ser | 110 |
| Gln | Gly | Thr | Arg | Ser | Leu | Thr | Pro | Cys | Thr | 120 |
| Cys | Gly | Ser | Ser | Asp | Leu | Tyr | Leu | Val | Thr | 130 |
| Arg | His | Ala | Asp | Val | Ile | Pro | Val | Arg | Arg | 140 |
| Arg | Gly | Asp | Ser | Arg | Gly | Ser | Leu | Leu | Ser | 150 |
| Pro | Arg | Pro | Ile | Ser | Tyr | Leu | Lys | Gly | Ser | 160 |
| Ser | Gly | Gly | Pro | Leu | Leu | Cys | Pro | Ala | Gly | 170 |
| His | Ala | Val | Gly | Ile | Phe | Arg | Ala | Ala | Val | 180 |
| Cys | Thr | Arg | Gly | Val | Ala | Lys | Ala | Val | Asp | 190 |
| Phe | Ile | Pro | Val | Glu | Asn | Leu | Glu | Thr | Thr | 200 |
| Met | Arg | (SEQ ID NO: 1) *** | | | | | | | | 202 |

The above N and C termini are putative, the actual termini being defined by expression and processing in an appropriate host of a DNA construct encoding the entire NS3 domain. It is understood that this sequence may vary from strain to strain, as RNA viruses like HCV are known to exhibit a great deal of variation. Further, the actual N and C termini may vary, as the protease is cleaved from a precursor polyprotein: variations in the protease amino acid sequence can result in cleavage from the polyprotein at different points. Thus, the amino- and carboxy-termini may differ from strain to strain of HCV. The first amino acid shown above corresponds to residue 60 in FIG. 1. However, the minimum sequence necessary for activity can be determined by routine methods. The sequence may be truncated at either end by treating an appropriate expression vector with an exonuclease (after cleavage at the 5' or 3' end of the coding sequence) to remove any desired number of base pairs. The resulting coding polynucleotide is then expressed and the sequence determined. In his manner the activity of the resulting product may be correlated with the amino acid sequence: a limited series of such experiments (removing progressively greater numbers of base pairs) determines the minimum internal sequence necessary for protease activity. We have found that the sequence may be substantially truncated, particularly at the carboxy terminus, apparently with full retention of protease activity. It is presently believed that a portion of the protein at the carboxy terminus may exhibit helicase activity. However, helicase activity is not required of the HCV proteases of the invention. The amino terminus may also be truncated to a degree without loss of protease activity.

The amino acids underlined above are believed to be the residues necessary for catalytic activity, based on sequence homology to putative flavivirus serine proteases. Table 1 shows the alignment of the three serine protease catalytic residues for HCV protease and the protease obtained from Yellow Fever Virus, West Nile Fever virus, Murray Valley Fever virus, and Kunjin virus. Although the other four flavivirus protease sequences exhibit higher homology with each other than with HCV, a degree of homology is still observed with HCV. This homology, however, was not sufficient for indication by currently available alignment software. The indicated amino acids are numbered $His_{79}$, $Asp_{103}$, and $Ser_{161}$ in the sequence listed above ($His_{139}$, $Asp_{163}$, and $Ser_{221}$ in FIG. 1).

a residue of equivalent size results in loss of activity, the essential nature of the replaced residue is confirmed.

"HCV protease analogs" refer to polypeptides which vary from the full length protease sequence by deletion, alteration and/or addition to the amino acid sequence of the native protease. HCV protease analogs include the truncated proteases described above, as well as HCV protease muteins and fusion proteins comprising HCV protease, truncated protease, or protease. muteins. Alterations to form HCV protease muteins are preferably conservative amino acid substitutions, in which an amino acid is replaced with another naturally-occurring amino acid of similar character. For example, the following substitutions are considered "conservative":

Gly←→Ala; Asp←→Glu;
Val←→Ile←→Leu;
Lys←→Arg;
Asn←→Gln; and
Phe←→Trp←→Tyr.

Nonconservative changes are generally substitutions of one of the above amino acids with an amino acid from a different group (e.g., substituting Asn for Glu), or substituting Cys, Met, His, or Pro for any of the above amino acids. Substitutions involving common amino acids are conveniently

TABLE 1

Alignment of Active Residues by Sequence

| Protease | His | Asp | Ser |
|---|---|---|---|
| HCV | CWTVYHGAG (SEQ ID NO:2) | DODLGWPAP (SEQ ID NO:3) | LKGSSGGPL (SEQ ID NO:4) |
| Yellow Fever | FHTMWHVTR (SEQ ID NO:5) | KEDLVAYGG (SEQ ID NO:6) | PSGTSGSPI (SEQ ID NO:7) |
| West Nile Fever | FHTLWHTTK (SEQ ID NO:8) | KEDRLCYGG (SEQ ID NO:9) | PTGTSGSPI (SEQ ID NO:10) |
| Murray Vally | FHTLWHTTR (SEQ ID NO:11) | KEDRVTYGG (SEQ ID NO:12) | PIGTSGSPI (SEQ ID NO:13) |
| Kunjin Virus | FHTLWHTTK (SEQ ID NO:14) | KEDRLCYGG (SEQ ID NO:15) | PTGTSGSPI (SEQ ID NO:16) |

Alternatively, one can make catalytic residue assignments based on structural homology. Table 2 shows alignment of HCV with against the catalytic sites of several well-characterized serine proteases based on structural considerations: protease A from *Streptomyces griseus*, α-lytic protease, bovine trypsin, chymotrypsin, and elastase (M. James et al, *Can J Biochem* (1978) 56:396). Again, a degree of homology is observed. The HCV residues identified are numbered $His_{79}$, $Asp_{125}$, and $Ser_{161}$ in the sequence listed above.

performed by site specific mutagenesis of an expression vector encoding the desired protein, and subsequent expression of the altered form. One may also alter amino acids by synthetic or semi-synthetic methods. For example, one may convert cysteine or serine residues to selenocysteine by appropriate chemical treatment of the isolated protein. Alternatively, one may incorporate uncommon amino acids in standard in vitro protein synthetic methods. Typically, the total number of residues changed, deleted or added to the native sequence in the muteins will be no more than about

TABLE 2

Alignment of Active Residues by Structure

| Protease | His | Asp | Ser |
|---|---|---|---|
| S. griseus A | TAGHC (SEQ ID NO: 17) | NNDYGII (SEQ ID NO: 18) | GDSGGSL (SEQ ID NO: 19) |
| α-Lytic protease | TAGHC (SEQ ID NO: 20) | GNDRAWV (SEQ ID NO: 21) | GDSGGSW (SEQ ID NO: 22) |
| Bovine Trypsin | SAAHC (SEQ ID NO: 23) | NNDIMLI (SEQ ID NO: 24) | GDSGGPV (SEQ ID NO: 25) |
| Chymotrypsin | TAAHC (SEQ ID NO: 26) | NNDITLL (SEQ ID NO: 27) | GDSGGPL (SEQ ID NO: 28) |
| Elastase | TAAHC (SEQ ID NO: 29) | GYDIALL (SEQ ID NO: 30) | GDSGGPL (SEQ ID NO: 31) |
| HCV | TVYHG (SEQ ID NO: 32) | SSDLYLV (SEQ ID NO: 33) | GSSGGPL (SEQ ID NO: 34) |

The most direct manner to verify the residues essential to the active site is to replace each residue individually with a residue of equivalent stearic size. This is easily accomplished by site-specific mutagenesis and similar methods known in the art. If replacement of a particular residue with 20, preferably no more than about 10, and most preferably no more than about 5.

The term fusion protein generally refers to a polypeptide comprising an amino acid sequence drawn from two or more individual proteins. In the present invention, "fusion protein" is used to denote a polypeptide comprising the HCV protease, truncate, mutein or a functional portion thereof, fused to a non-HCV protein or polypeptide ("fusion partner"). Fusion proteins are most conveniently produced by expression of a fused gene, which encodes a portion of one polypeptide at the 5' end and a portion of a different polypeptide at the 3' end, where the different portions are joined in one reading frame which may be expressed in a suitable host. It is presently preferred (although not required) to position the HCV protease or analog at the carboxy terminus of the fusion protein, and to employ a functional enzyme fragment at the amino terminus. As the HCV protease is normally expressed within a large polyprotein, it is not expected to include cell transport signals (e.g., export or secretion signals). Suitable functional enzyme fragments are those polypeptides which exhibit a quantifiable activity when expressed fused to the HCV protease. Exemplary enzymes include, without limitation, β-galactosidase (β-gal), β-lactamase, horseradish peroxidase (HRP), glucose oxidase (GO), human superoxide dismutase (hSOD), urease, and the like. These enzymes are convenient because the amount of fusion protein produced can be quantified by means of simple colorimetric assays. Alternatively, one may employ antigenic proteins or fragments, to permit simple detection and quantification of fusion proteins using antibodies specific for the fusion partner. The presently preferred fusion partner is hSOD.

B. General Method

The practice of the present invention generally employs conventional techniques of molecular biology, microbiology, recombinant DNA, and immunology, which are within the skill of the art. Such techniques are explained fully in the literature. See for example J. Sambrook et al, "Molecular Cloning; A Laboratory Manual (1989); "DNA Cloning", Vol. I and II (D. N Glover ed. 1985); "Oligonucleotide Synthesis" (M. J. Gait ed, 1984); "Nucleic Acid Hybridization" (B. D. Hames & S. J. Higgins eds. 1984); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods In Enzymology" (Academic Press, Inc.); "Gene Transfer Vectors For Mammalian Cells" (J. H. Miller and M. P. Calos eds. 1987, Cold Spring Harbor Laboratory); Meth Enzymol (1987) 154 and 155 (Wu and Grossman, and Wu, eds., respectively); Mayer & Walker, eds. (1987), "Immunochemical Methods In Cell And Molecular Biology" (Academic Press, London); Scopes, "protein Purification: Principles And Practice", 2nd Ed (Springer-Verlag, N.Y., 1987); and "Handbook Of Experimental Immunology", volumes I–IV (Weir and Blackwell, eds, 1986).

Both prokaryotic and eukaryotic host cells are useful for expressing desired coding sequences when appropriate control sequences compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These plasmids are commercially available. The markers may be used to obtain successful transformants by selection. Commonly used prokaryotic control sequences include the β-lactamase (penicillinase) and lactose promoter systems (Chang et al, *Nature* (1977) 198:1056), the tryptophan (trp) promoter system (Goeddel et al, *Nuc Acids Res* (1980) 8:4057) and the lambda-derived $P_L$ promoter and N gene ribosome binding site (Shimatake et al, *Nature* (1981) 292:128) and the hybrid tac promoter (De Boer et al, *Proc Nat Acad Sci USA* (1983) 292:128) derived from sequences of the trp and lac UV5 promoters. The foregoing systems are particularly compatible with *E. coli*; if desired, other prokaryotic hosts such as strains of Bacillus or Pseudomonas may be used, with corresponding control sequences.

Eukaryotic hosts include without limitation yeast and mammalian cells in culture systems. Yeast expression hosts include Saccharomyces, Klebsiella, Picia, and the like. *Saccharomyces cerevisiae* and *Saccharomyces carlsbergensis* and *K. lactis* are the most commonly used yeast hosts, and are convenient fungal hosts. Yeast-compatible vectors carry markers which permit selection of successful transformants by conferring prototrophy to auxotrophic mutants or resistance to heavy metals on wild-type strains. Yeast compatible vectors may employ the $2\mu$ origin of replication (Broach et al, *Meth Enzymol* (1983) 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al, *J Adv Enzyme Reg* (1968) 7:149; Holland et al, *Biochem* (1978), 17:4900), including the promoter for 3-phosphoglycerate kinase (R. Hitzeman et al, *J Biol Chem* (1980) 255:2073). Terminators may also be included, such as those derived from the enolase gene (Holland, *J Biol Chem* (1981) 256:1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, a leader sequence derived from yeast α-factor (see U.S. Pat. No. 4,870,008, incorporated herein by reference).

A presently preferred expression system employs the ubiquitin leader as the fusion parmer. Copending application U.S. Ser. No. 7/390,599 filed 7 Aug. 1989 disclosed vectors for high expression of yeast ubiquitin fusion proteins. Yeast ubiquitin provides a 76 amino acid polypeptide which is automatically cleaved from the fused protein upon expression. The ubiquitin amino acid sequence is as follows:

Gln Ile Phe Val Lys Thr Leu Thr Gly Lys Thr Ile Thr

Leu Glu Val Glu Ser Ser Asp Thr Ile Asp Asn Val Lys

Ser Lys Ile Gln Asp Lys Glu Gly Ile Pro Pro Asp Gln

Gln Arg Leu Ile Phe Ala Gly Lys Gln Leu Glu Asp Gly

Arg Thr Leu Ser Asp Tyr Asn Ile Gln Lys Glu Ser Thr

Leu His Leu Val Leu Arg Leu Arg Gly Gly (SEQ ID NO: 35)

See also Ozkaynak et al, *Nature* (1984) 312:663–66. Polynucleotides encoding the ubiquitin polypeptide may be synthesized by standard methods, for example following the technique of Barr et al, *J Biol Chem* (1988) 268:1671–78 using an Applied Biosystem 380A DNA synthesizer. Using appropriate linkers, the ubiquitin gene may be inserted into a suitable vector and ligated to a sequence encoding the HCV protease or a fragment thereof.

In addition, the transcriptional regulatory region and the transcriptional initiation region which are operably linked may be such that they are not naturally associated in the wild-type organism. These systems are described in detail in EPO 120,551, published Oct. 3, 1984; EPO 116,201, published Aug. 22, 1984; and EPO 164,556, published Dec. 18, 1985, all of which are commonly owned with the present invention, and are hereby incorporated herein by reference in full.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) tiers et al, *Nature* (1978) 273:113), Rous sarcoma virus (RSV), adenovirus (ADV), and bovine papilloma virus (BPV). Mammalian cells may also require terminator sequences and poly-A addition sequences. Enhancer sequences which increase expression may also be included, and sequences which promote amplification of the gene may also be desirable (for example methotrexate resistance genes). These sequences are known in the art.

Vectors suitable for replication in mammalian cells are known in the art, and may include viral replicons, or sequences which insure integration of the appropriate sequences encoding HCV epitopes into the host genome. For example, another vector used to express foreign DNA is Vaccinia virus. In this case the heterologous DNA is inserted into the Vaccinia genome. Techniques for the insertion of foreign DNA into the vaccinia virus genome are known in the art, and may utilize, for example, homologous recombination. The heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, *J Virol* (1984) 49:857; Chakrabarti et al, *Mol Cell Biol* (1985) 5:3403; Moss, in GENE TRANSFER VECTORS FOR MAMMALLAN CELLS (Miller and Calos, eds., Cold Spring Harbor Laboratory, N.Y., 1987), p. 10). Expression of the HCV polypeptide then occurs in cells or animals which are infected with the live recombinant vaccinia virus.

In order to detect whether or not the HCV polypeptide is expressed from the vaccinia vector, BSC 1 cells may be infected with the recombinant vector and grown on microscope slides under conditions which allow expression. The cells may then be acetone-fixed, and immunofluorescence assays performed using serum which is known to contain anti-HCV antibodies to a polypeptide(s) encoded in the region of the HCV genome from which the HCV segment in the recombinant expression vector was derived.

Other systems for expression of eukaryotic or viral genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector Expression vectors derived from this system usually use the strong viral polyhedrin gene promoter to drive expression of heterologous genes. Currently the most commonly used transfer vector for introducing foreign genes into AcNPV is pAc373 (see PCT WO89/046699 and U.S. Ser. No. 7/456,637). Many other vectors known to those of skill in the art have also been designed for improved expression. These include, for example, pVL985 (which alters the polyhedrin start codon from ATG to ATT, and introduces a BamHI cloning site 32 bp downstream from the ATT; See Luckow and Summers, *Virol* (1989) 17:31). AcNPV transfer vectors for high level expression of nonfused foreign proteins are described in copending applications PCT WO89/046699 and U.S. Ser. No. 7/456,637. A unique BamHI site is located following position −8 with respect to the translation initiation codon ATG of the polyhedrin gene. There are no cleavage sites for SmaI, PstI, BglII, XbaI or SstI. Good expression of nonfused foreign proteins usually requires foreign genes that ideally have a short leader sequence containing suitable translation initiation signals preceding an ATG start signal. The plasmid also contains the polyhedrin polyadenylation signal and the ampicillin-resistance (amp) gene and origin of replication for selection and propagation in *E. coli.*

Methods for the introduction of heterologous DNA into the desired site in the baculovirus virus are known in the art. (See Summer and Smith, Texas Agricultural Experiment Station Bulletin No. 1555; Smith et al, *Mol Cell Biol* (1983) 3:2156–2165; and Luckow and Summers, *Virol* (1989) 17:31). For example, the heterologous DNA can be inserted into a gene such as the polyhedrin gene by homologous recombination, or into a restriction enzyme site engineered into the desired baculovirus gene. The inserted sequences may be those which encode all or varying segments of the polyprotein, or other orfs which encode viral polypeptides. For example, the insert could encode the following numbers of amino acid segments from the polyprotein: amino acids 1–1078; amino acids 332–662; amino acids 406–662; amino acids 156–328, and amino acids 199–328.

The signals for post-translational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin-2 signal ($IL2_s$) which signals for secretion from the cell, is recognized and properly removed in insect cells.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen, *Proc Nat Acad Sci USA* (1972) 69:2110; T. Maniatis et al, "Molecular Cloning; A Laboratory Manual" (Cold Spring Harbor Press, Cold Spring Harbor, N.Y., 1982). Yeast transformation by direct uptake may be carried out using the method of Hinnen et al, *Proc Nat Acad Sci USA* (1978) 75:1929. Mammalian transformations by direct uptake may be conducted using the calcium phosphate precipitation method of Graham and Van der Eb, *Virol* (1978) 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

Vector construction employs techniques which are known in the art. Site-specific DNA cleavage is performed by treating with suitable restriction enzymes under conditions which generally are specified by the manufacturer of these commercially available enzymes. In general, about 1 μg of plasmid or DNA sequence is cleaved by 1 unit of enzyme in about 20 μL buffer solution by incubation for 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures described in *Meth Enzymol* (1980) 65:499–560.

Sticky-ended cleavage fragments may be blunt ended using *E. coli* DNA polymerase I (Klenow fragment) with the appropriate deoxynucleotide triphosphates (dNTPs) present in the mixture. Treatment with S1 nuclease may also be used, resulting in the hydrolysis of any single stranded DNA portions.

Ligations are carried out under standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate, thus preventing religation of the vector. Alternatively, restriction enzyme digestion of unwanted fragments can be used to prevent ligation.

Ligation mixtures are transformed into suitable cloning hosts, such as *E. coli*, and successful transformants selected using the markers incorporated (e.g., antibiotic resistance), and screened for the correct construction.

Synthetic oligonucleotides may be prepared using an automated oligonucleotide synthesizer as described by Warner, *DNA* (1984) 3:401. If desired, the synthetic strands may be labeled with $^{32}$P by treatment with polynucleotide kinase in the presence of $^{32}$P-ATP under standard reaction conditions.

DNA sequences, including those isolated from cDNA libraries, may be modified by known techniques, for example by site directed mutagenesis (see e.g., Zoller, *Nuc Acids Res* (1982) 10:6487). Briefly, the DNA to be modified is packaged into phage as a single stranded sequence, and converted to a double stranded DNA with DNA polymerase, using as a primer a synthetic oligonucleotide complementary to the portion of the DNA to be modified, where the desired modification is included in the primer sequence. The resulting double stranded DNA is transformed into a phage-supporting host bacterium. Cultures of the transformed bacteria which contain copies of each strand of the phage are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

DNA libraries may be probed using the procedure of Grunstein and Hogness *Proc Nat Acad Sci USA* (1975) 73:3961. Briefly, in this procedure the DNA to be probed is immobilized on nitrocellulose filters, denatured, and prehybridized with a buffer containing 0–50% formamide, 0.75M NaCl, 75 mM Na citrate, 0.02% (wt/v) each of bovine serum albumin, polyvinylpyrrolidone, and Ficoll®, 50 mM NaH$_2$PO$_4$ (pH 6.5), 0.1% SDS, and 100 μg/mL carrier denatured DNA. The percentage of formamide in the buffer, as well as the time and temperature conditions of the prehybridization and subsequent hybridization steps depend on the stringency required. Oligomeric probes which require lower stringency conditions are generally used with low percentages of formamide, lower temperatures, and longer hybridization times. Probes containing more than 30 or 40 nucleotides, such as those derived from cDNA or genomic sequences generally employ higher temperatures, e.g., about 40°–42° C., and a high percentage formamide, e.g., 50%. Following prehybridization, 5'-$^{32}$P-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

For routine vector constructions, ligation mixtures are transformed into *E. coli* strain HB101 or other suitable hosts, and successful transformants selected by antibiotic resistance or other markers. Plasmids from the transformants are then prepared according to the method of Clewell et al, *Proc Nat Acad Sci USA* (1969) 62:1159, usually following chloramphenicol amplification (Clewell, *J Bacteriol* (1972) 110:667). The DNA is isolated and analyzed, usually by restriction enzyme analysis and/or sequencing. Sequencing may be performed by the dideoxy method of Sanger et al, *Proc Nat Acad Sci USA* (1977) 74:5463, as further described by Messing et al, *Nuc Acids Res* (1981) 9:309, or by the method of Maxam et al, *Meth Enzymol* (1980) 65:499. Problems with band compression, which are sometimes observed in GC-rich regions, were overcome by use of T-deazoguanosine according to Barr et al, *Biotechniques* (1986) 4:428.

The enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microtiter dish, plastic cup, dipstick, plastic bead, or the like), incubated with test serum dilutions, washed, incubated with anti-immunoglobulin labeled with an enzyme, and washed again. Enzymes suitable for labeling are known in the art, and include, for example, horseradish peroxidase (HRP). Enzyme activity bound to the solid phase is usually measured by adding a specific substrate, and determining product formation or substrate utilization calorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is measured colorimetricaly, and related to antigen concentration.

Proteases of the invention may be assayed for activity by cleaving a substrate.which provides detectable cleavage products. As the HCV protease is believed to cleave itself from the genomic polyprotein, one can employ this autocatalytic activity both to assay expression of the protein and determine activity. For example, if the protease is joined to its fusion partner so that the HCV protease N-terminal cleavage signal (Arg—Arg) is included, the expression product will cleave itself into fusion partner and active HCV protease. One may then assay the products, for example by western blot, to verify that the proteins produced correspond in size to the separate fusion partner and protease proteins. It is presently preferred to employ small peptide p-nitrophenyl esters or methylcoumarins, as cleavage may then be followed by spectrophotometric or fluorescent assays. Following the method described by E. D. Matayoshi et al, *Science* (1990) 247:231–35, one may attach a fluorescent label to one end of the substrate and a quenching molecule to the other end: cleavage is then determined by measuring the resulting increase in fluorescence. If a suitable enzyme or antigen has been employed as the fusion partner, the quantity of protein produced may easily be determined. Alternatively, one may exclude the HCV protease N-terminal cleavage signal (preventing self-cleavage) and add a separate cleavage substrate, such as a fragment of the HCV NS3 domain including the native processing signal or a synthetic analog.

In the absence of this protease activity, the HCV polyprotein should remain in its unprocessed form, and thus render the virus noninfectious. Thus, the protease is useful for assaying pharmaceutical agents for control of HCV, as compounds which inhibit the protease activity sufficiently will also inhibit viral infectivity. Such inhibitors may take the form of organic compounds, particularly compounds which mimic the cleavage site of HCV recognized by the protease. Three of the putative cleavage sites of the HCV polyprotein have the following amino acid sequences:

Val—Ser—Ala—Arg—Arg // Gly—Arg—Glu—Ile—Leu—Leu—Gly
Ala—Ile—Leu—Arg—Arg // His—Val—Gly—Pro—
Val—Ser—Cys—Gln—Arg // Gly—Tyr— (SEQ ID NO: 36)

These sites are characterized by the presence of two basic amino acids immediately before the cleavage site, and are similar to the cleavage sites recognized by other flavivirus proteases. Thus, suitable protease inhibitors may be prepared which mimic the basic/basic/small neutral motif of the HCV cleavage sites, but substituting a nonlabile linkage for the peptide bond cleaved in the natural substrate. Suitable inhibitors include peptide trifluoromethyl ketones, peptide boronic acids, peptide α-ketoesters, peptide difluoroketo compounds, peptide aldehydes, peptide diletones, and the like. For example, the peptide aldehyde N-acetylphenylalanylglycinaldehyde is a potent inhibitor of the protease papain. One may conveniently prepare and assay large mixtures of peptides using the methods disclosed in U.S. patent application Ser. No. 7/189,318, filed 2 May 1988 (published as PCT WO89/10931), incorporated herein by reference. This application teaches methods for generating mixtures of peptides up to hexapeptides having all possible amino acid sequences, and further teaches assay methods for identifying those peptides capable of binding to proteases.

Other protease inhibitors may be proteins, particularly antibodies and antibody derivatives. Recombinant expression systems may be used to generate quantities of protease sufficient for production of monoclonal antibodies (MAbs) specific for the protease. Suitable antibodies for protease inhibition will bind to the protease in a manner reducing or eliminating the enzymatic activity, typically by obscuring the active site. Suitable MAbs may be used to generate derivatives, such as Fab fragments, chimeric antibodies, altered antibodies, univalent antibodies, and single domain antibodies, using methods known in the art.

Protease inhibitors are screened using methods of the invention. In general, a substrate is employed which mimics the enzyme's natural substrate, but which provides a quantifiable signal when cleaved. The signal is preferably detectable by colorimetric or fluorometric means: however, other methods such as HPLC or silica gel chromatography, GC-MS, nuclear magnetic resonance, and the like may also be useful. After optimum substrate and enzyme concentrations are determined, a candidate protease inhibitor is added to the reaction mixture at a range of concentrations. The assay conditions ideally should resemble the conditions under which the protease is to be inhibited in vivo, i.e., under physiologic pH, temperature, ionic strength, etc. Suitable inhibitors will exhibit strong protease inhibition at concentrations which do not raise toxic side effects in the subject. Inhibitors which compete for binding to the protease active site may require concentrations equal to or greater than the substrate concentration, while inhibitors capable of binding irreversibly to the protease active site may be added in concentrations on the order of the enzyme concentration.

In a presently preferred embodiment, an inactive protease mutein is employed rather than an active enzyme. It has been found that replacing a critical residue within the active site of a protease (e.g., replacing the active site Ser of a serine protease) does not significantly alter the structure of the enzyme, and thus preserves the binding specificity. The altered enzyme still recognizes and binds to its proper substrate, but fails to effect cleavage. Thus, in one method of the invention an inactivated HCV protease is immobilized, and a mixture of candidate inhibitors added. Inhibitors that closely mimic the enzyme's preferred recognition sequence will compete more successfully for binding than other candidate inhibitors. The poorly-binding candidates may then be separated, and the identity of the strongly-binding inhibitors determined. For example, HCV protease may be prepared substituting Ala for $Ser_{221}$ (FIG. 1), providing an enzyme capable of binding the HCV protease substrate, but incapable of cleaving it. The resulting protease mutein is then bound to a solid support, for example Sephadex® beads, and packed into a column. A mixture of candidate protease inhibitors in solution is then passed through the column and fractions collected. The last fractions to elute will contain the strongest-binding compounds, and provide the preferred protease inhibitor candidates.

Protease inhibitors may be administered by a variety of methods, such as intravenously, orally, intramuscularly, intraperitoneally, bronchially, intranasally, and so forth. The preferred route of administration will depend upon the nature of the inhibitor. Inhibitors prepared as organic compounds may often be administered orally (which is generally preferred) if well absorbed. Protein-based inhibitors (such as most antibody derivatives) must generally be administered by parenteral routes.

C. Examples

The examples presented below are provided as a further guide to the practitioner of ordinary skill in the art, and are not to be construed as limiting the invention in any way.

EXAMPLE 1

(Preparation of HCV cDNA)

A genomic library of HCV cDNA was prepared as described in PCT WO89/046699 and U.S. Ser. No. 7/456, 637. This library, ATCC accession no. 40394, has been deposited as set forth below.

EXAMPLE 2

(Expression of the Polypeptide Encoded in Clone 5-1-1.)

(A) The HCV polypeptide encoded within clone 5-1-1 (see Example 1) was expressed as a fusion polypeptide with human superoxide dismutase (SOD). This was accomplished by subcloning the clone 5-1-1 cDNA insert into the expression vector pSODCF1 (K. S. Steimer et al, *J Virol* (1986) 58:9; EPO 138,111) as follows. The SOD/5-1-1 expression vector was transformed into *E. coli* D1210 cells.

These cells, named Cf1/5-1-1 in *E. coli*, were deposited as set forth below and have an ATCC accession no. of 67967.

First, DNA isolated from pSODCF1 was treated with BamHI and EcoRI, and the following linker was ligated into the linear DNA created by the restriction enzymes:

GAT CCT GGA ATT CTG ATA AGA CCT TAA GAC TAT TTT AA (SEQ ID NO: 37)

After cloning, the plasmid containing the insert was isolated.

Plasmid containing the insert was restricted with EcoRI. The HCV cDNA insert in clone 5-1-1 was excised with EcoRI, and ligated into this EcoRI linearized plasmid DNA. The DNA mixture was used to transform *E. coli* strain D1210 (Sadler et al, *Gene* (1980) 8:279). Recombinants with the 5-1-1 cDNA in the correct orientation for expressing the ORF shown in FIG. 1 were identified by restriction mapping and nucleotide sequencing.

Recombinant bacteria from one clone were induced to express the SOD-HCV$_{5-1-1}$ polypeptide by growing the bacteria in the presence of IPTG.

Three separate expression vectors, pcf1AB, pcf1CD, and pcf1EF were created by ligating three new linkers, AB, CD, and EF to a BamHI-EcoRI fragment derived by digesting to completion the vector pSODCF1 with EcoRI and BamHI, followed by treatment with alkaline phosphatase. The linkers were created from six oligomers, A, B, C, D, E, and F. Each oligomer was phosphorylated by treatment with kinase in the presence of ATP prior to annealing to its complementary oligomer. The sequences of the synthetic linkers were the following:

| Name | DNA Sequence (5' to 3') | | | | | |
|---|---|---|---|---|---|---|
| A | GATC | CTG | AAT | TCC | TGA | TAA (SEQ ID NO: 38) |
| B | | GAC | TTA | AGG | ACT ATT | TTA  A (SEQ ID NO: 39) |
| C | GATC | CGA | ATT | CTG | TGA | TAA (SEQ ID NO: 40) |
| D | | GCT | TAA | GAC | ACT ATT | TTA  A (SEQ ID NO: 41) |
| E | GATC | CTG | GAA | TTC | TGA | TAA (SEQ ID NO: 42) |
| F | | GAC | CTT | AAG | ACT ATT | TTA  A (SEQ ID NO: 43) |

Each of the three linkers destroys the original EcoRI site, and creates a new EcoRi site within the linker, but within a different reading frame. Thus, the HCV cDNA EcoRI fragments isolated from the clones, when inserted into the expression vector, were in three different reading frames.

The HCV cDNA fragments in the designated λgt11 clones were excised by digestion with EcoRI; each fragment was inserted into pcf1AB, pcf1CD, and pcf1EF. These expression constructs were then transformed into D1210 *E. coli* cells, the transformants cloned, and polypeptides expressed as described in part B below.

(B) Expression products of the indicated HCV cDNAs were tested for antigenicity by direct immunological screening of the colonies, using a modification of the method described in Helfman et al, *Proc Nat Acad Sci USA* (1983), 80:31. Briefly, the bacteria were plated onto nitrocellulose filters overlaid on ampicillin plates to give approximately 40 colonies per filter. Colonies were replica plated onto nitrocellulose filters, and the replicas were regrown overnight in the presence of 2 mM IPTG and ampicirin. The bacterial colonies were lysed by suspending the nitrocellulose filters for about 15 to 20 min in an atmosphere saturated with CHCl$_3$ vapor. Each filter then was placed in an individual 100 mm Petri dish containing 10 mL of 50 mM Tris HCl, pH 7.5, 150 mM NaCl, 5 mM MgCl$_2$, 3% (w/v) BSA, 40 µg/mL lysozyme, and 0.1 µg/mL DNase. The plates were agitated gently for at least 8 hours at room temperature. The filters were rinsed in TBST (50 mM Tris HCl, pH 8.0, 150 mM NaCl, 0.005% Tween® 20). After incubation, the cell residues were rinsed and incubated for one hour in TBS (TBST without Tween®) containing 10% sheep serum. The filters were then incubated with pretreated sera in TBS from individuals with NANBH, which included 3 chimpanzees; 8 patients with chronic NANBH whose sera were positive with respect to antibodies to HCV C100-3 polypeptide (also called C100); 8 patients with chronic NANBH whose sera were negative for anti-C100 antibodies; a convalescent patient whose serum was negative for anti-C100 antibodies; and 6 patients with community-acquired NANBH, including one whose sera was strongly positive with respect to anti-C100 antibodies, and one whose sera was marginally positive with respect to anti-C100 antibodies. The sera, diluted in TBS, was pretreated by preabsorption with hSOD for at least 30 minutes at 37° C. After incubation, the filters were washed twice for 30 min with TBST. The expressed proteins which bound antibodies in the sera were labeled by incubation for 2 hours with $^{125}$I-labeled sheep anti-human antibody. After washing, the filters were washed twice for 30 min with TBST, dried, and autoradiographed.

EXAMPLE 3
(Cloning of Full-Length SOD-Protease Fusion Proteins)
(A) pBR322-C200:

The nucleotide sequences of the HCV cDNAs used below were determined essentially as described above, except that the cDNA excised from these phages were substituted for the cDNA isolated from clone 5-1-1.

Clone C33c was isolated using a hybridization probe having the following sequence:

5' ATC AGG ACC GGG GTG AGA ACA ATT ACC ACT 3' (SEQ ID NO: 44)

The sequence of the HCV cDNA in clone C33c is shown in FIG. 8, which also shows the amino acids encoded therein.

Clone 35 was isolated by screening with a synthetic polynucleotide having the sequence:

5' AAG CCA CCG TGT GCG CTA GGG CTC AAG CCC 3' (SEQ ID NO: 45)

Approximately 1 in 50,000 clones hybridized with the probe. The polynucleotide and deduced amino acid sequences for C35 are shown in FIG. 7.

Clone C31 is shown in FIG. 6, which also shows the amino acids encoded therein. A C200 cassette was constructed by ligating together a 718 bp fragment obtained by digestion of clone C33c DNA with EcoRI and HinfI, a 179 bp fragment obtained by digestion of clone C31 DNA with HinfI and BglI, and a 377 bp fragment obtained by digesting clone C35 DNA with BglI and EcoRI. The construct of ligated fragments were inserted into the EcoRI site of pBR322, yielding the plasmid pBR322-C200.

(B) C7f+C20c:

Clone 7f was isolated using a probe having the sequence:

5'-AGC AGA CAA GGG GCC TCC TAG GGT GCA TAA T-3' (SEQ ID NO: 46)

The sequence of HCV cDNA in clone 7f and the amino acids encoded therein are shown in FIG. 5.

Clone C20c is isolated using a probe having the following sequence;

5'-TGC ATC AAT GGG GTG TGC TGG-3' (SEQ ID NO: 47)

The sequence of HCV cDNA in clone C20c, and the amino acids encoded therein are shown in FIG. 2.

Clones 7f and C20c were digested with EcoRI and SfaNI to form 400 bp and 260 bp fragments, respectively. The fragments were then cloned into the EcoRI site of pBR322 to form the vector C7f+C20c, and transformed into HB101 cells.

(C) C300:

Clone 8h was isolated using a probe based on the sequence of nucleotides in clone 33c. The nucleotide sequence of the probe was

5'-AGA GAC AAC CAT GAG GTC CCC GGT GTT C-3' (SEQ ID NO: 48).

The sequence of the HCV cDNA in clone 8h, and the amino acids encoded therein, are shown in FIG. 4.

Clone C26d is isolated using a probe having the following sequence:

5'-CTG TTG TGC CCC GCG GCA GCC-3' (SEQ ID NO: 49)

The sequence and amino acid translation of clone C26d is shown in FIG. 3.

Clones C26d and C33c (see part A above) were transformed into the methylation minus *E. coli* strain GM48. Clone C26d was digested with EcoRII and DdeI to provide a 100 bp fragment. Clone C33c was digested with EcoRII and EcoRI to provide a 700 bp fragment. Clone C8h was digested with EcoRI and DdeI to provide a 208 bp fragment. These three fragments were then ligated into the EcoRI site of pBR322, and transformed into *E. coli* HB101, to provide the vector C300.

(D) Preparation of Full Length Clones:

A 600 bp fragment was obtained from C7f+C20c by digestion with EcoRI and NaeI, and ligated to a 945 bp NaeI/EcoRI fragment from C300, and the construct inserted into the EcoRI site of pGEM4Z (commercially available from Promega) to form the vector C7fC20cC300.

Figure 9B:
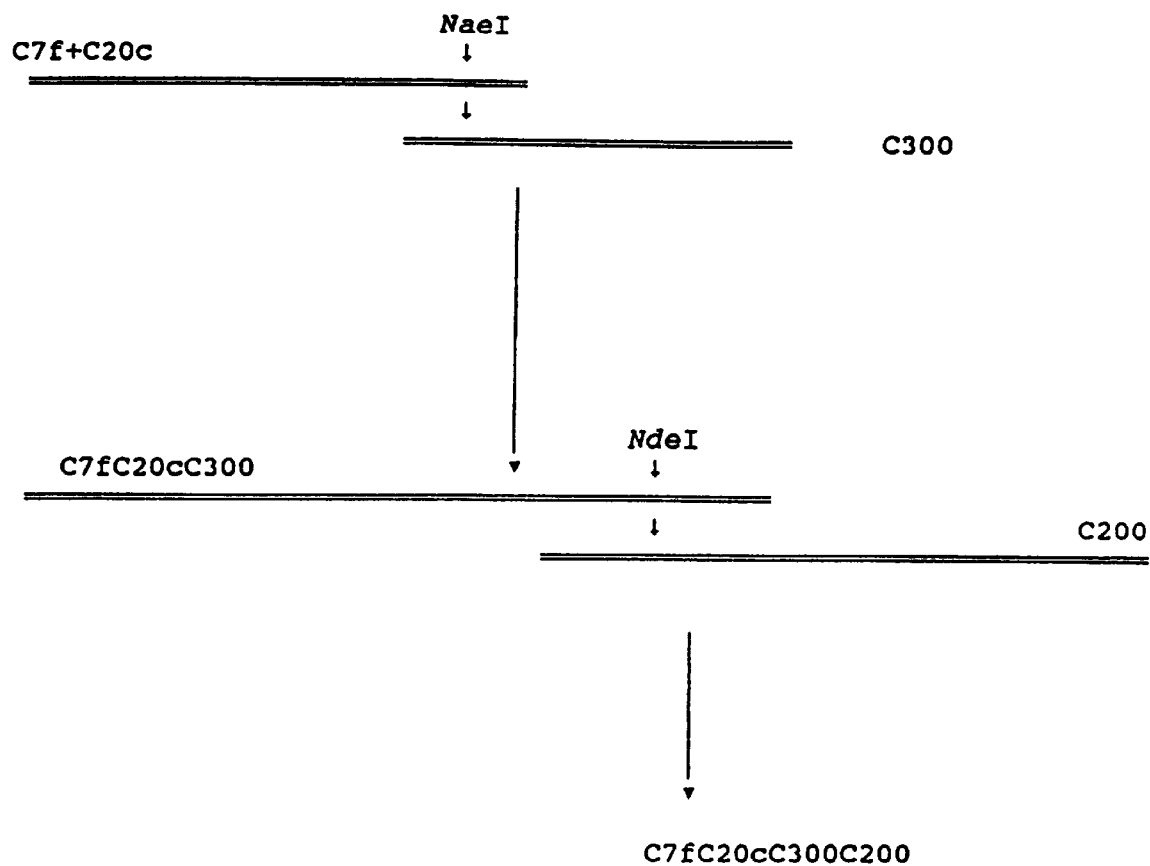

C7fC20cC300 was digested with NdeI and EcoRI to provide a 892 bp fragment, which was ligated with a 1160 bp fragment obtained by digesting C200 with NdeI and EcoRI. The resulting construct was inserted into the EcoRI site of pBR322 to provide the vector C7fC20cC300C200. Construction of this vector is illustrated schematically in FIG. 9.

EXAMPLE 4

Preparation of *E. coli* Expression Vectors)

(A) cf1SODp600:

This vector contains a full-length HCV protease coding sequence fused to a functional hSOD leader. The vector C7fC20cC300C200 was cleaved with EcoRI to provide a 2000 bp fragment, which was then ligated into the EcoRI site of plasmid cf1CD (Example 2A). The resulting vector encodes amino acids 1–151 of hSOD, and amino acids 946–1630 of HCV (numbered from the beginning of the polyprotein, corresponding to amino acids 1–686 in FIG. 1). The vector was labeled cf1SODp600 (sometimes referred to as P600), and was transformed into *E. coli* D1210 cells. These cells, ATCC accession no. 68275, were deposited as set forth below.

(B) P190:

A truncated SOD-protease fusion polynucleotide was prepared by excising a 600 bp EcoRI/NaeI fragment from C7f+C20c, blunting the fragment with Klenow fragment, ligating the blunted fragment into the Klenow-blunted EcoRI site of cf1EF (Example 2A). This polynucleotide encodes a fusion protein having amino acids 1–151 of hSOD, and amino acids 1–199 of HCV protease.

(C) P300:

A longer truncated SOD-protease fusion polynucleotide was prepared by excising an 892 bp EcoRI/NdeI fragment from C7fC20cC300, blunting the fragment with Klenow fragment, ligating the blunted fragment into the Klenow-blunted EcoRI site of cf1EF. This polynucleotide encodes a fusion protein having amino acids 1–151 of hSOD, and amino acids 1–299 of HCV protease.

(D) P500:

A longer truncated SOD-protease fusion polynucleotide was prepared by excising a 1550 bp EcoRI/EcoRI fragment from C7fC20cC300, and ligating the fragment into the EcoRI site of cf1CD to form P500. This polynucleotide encodes a fusion protein having amino acids 1–151 of hSOD, and amino acids 946–1457 of HCV protease (amino acids 1–513 in FIG. 1).

(E) FLAG/Protease Fusion

This vector contains a full-length HCV protease coding sequence fused to the FLAG sequence, Hopp et al. (1988) *Biotechnology* 6: 1204–1210. PCR was used to produce a HCV protease gene with special restriction ends for cloning ease. Plasmid p500 was digested with EcoRI and NdeI to yield a 900 bp fragment. This fragment and two primers were used in a: polymerase chain reaction to introduce a unique BglII site at amino acid 1009 and a stop codon with a SalI site at amino acid 1262 of the HCV-1, as shown in FIG. 17 of WO 90/11089, published 4 Oct. 1990. The sequence of the primers is as follows:

5' CCC GAG CAA GAT CTC CCG GCC C 3' (SEQ ID NO: 50) and

5' CCC GGC TGC ATA AGC AGT CGA CTT GGA 3' (SEQ ID NO: 51)

After 30 cycles of PCR, the reaction was digested with BglII and SalI, and the 710 bp fragment was isolated. This fragment was annealed and ligated to the following duplex:

Met Asp Tyr Lys Asp Asp Asp Asp Lys Gly Arg Glu

CATGGACTACAAAGACGATGACGATAAAGGCCGGGAG

CTGATGTTTCTGCTACTGCTATTTCCGGCCCTCTAG
(SEQ ID NO: 52) and (SEQ ID NO: 53)

The duplex encodes the FLAG sequence, and initiator methionine, and a 5' NcoI restriction site. The resulting NcoI/SalI fragment was ligated into a derivative of pCF1.

This construct is then transformed into *E. coli* D1210 cells and expression of the protease is induced by the addition of IPTG.

The FLAG sequence was fused to the HCV protease to facilitate purification. A calcium dependent monoclonal antibody, which binds to the FLAG encoded peptide, is used to purify the fusion protein without harsh eluting conditions.

EXAMPLE 5

(*E. coli* Expression of SOD-Protease Fusion Proteins)

(A) *E. coli* D1210 cells were transformed with cf1SODp600 and grown in Luria broth containing 100 μg/mL ampicillin to an OD of 0.3–0.5. IPTG was then added to a concentration of 2 mM, and the cells cultured to a fmal OD of 0.9 to 1.3. The cells were then lysed, and the lysate analyzed by Western blot using anti-HCV sera, as described in U.S. Ser. No. 7/456,637.

The results indicated the occurrence of cleavage, as no full length product (theoretical Mr 93 kDa) was evident on the gel. Bands corresponding to the hSOD fusion partner and the separate HCV protease appeared at relative molecular weights of about 34, 53, and 66 kDa. The 34 kDa band corresponds to the hSOD partner (about 20 kDa) with a portion of the NS3 domain, while the 53 and 66 kDa bands correspond to HCV protease with varying degrees of (possibly bacterial) processing.

(B) *E. coli* D1210 cells were transformed with P500 and grown in Luria broth containing 100 μg/mL ampicillin to an OD of 0.3–0.5. IPTG was then added to a concentration of 2 mM, and the cells cultured to a fimal OD of 0.8 to 1.0. The cells were then lysed, and the lysate analyzed as described above.

The results again indicated the occurrence of cleavage, as no full length product (theoretical Mr 73 kDa) was evident on the gel. Bands corresponding to the hSOD fusion partner and the truncated HCV protease appeared at molecular weights of about 34 and 45 kDa, respectively.

(C) *E. coli* D1210 cells were transformed with vectors P300 and P190 and grown as described above.

The results from P300 expression indicated the occurrence of cleavage, as no full length product (theoretical Mr 51 kDa) was evident on the gel. A band corresponding to the hSOD fusion partner appeared at a relative molecular weight of about 34. The corresponding HCV protease band was not visible, as this region of the NS3 domain is not recognized by the sera employed to detect the products. However, appearance of the hSOD band at 34 kDa rather than 51 kDa indicates that cleavage occurred.

The P190 expression product appeared only as the full (encoded) length product without cleavage, forming a band at about 40 kDa, which corresponds to the theoretical molecular weight for the uncleaved product. This may indicate that the minimum essential sequence for HCV protease extends to the region between amino acids 199 and 299.

EXAMPLE 6
(Purification of *E. coli* Expressed Protease)

The HCV protease and fragments expressed in Example 5 may be purified as follows:

The bacterial cells in which the polypeptide was expressed are subjected to osmotic shock and mechanical disruption, the insoluble fraction containing the protease is isolated and subjected to differential extraction with an alkaline-NaCl solution, and the polypeptide in the extract purified by chromatography on columns of S-Sepharose® and Q-Sepharose®.

The crude extract resulting from osmotic shock and mechanical disruption is prepared by suspending 1 g of the packed cells in 10 mL of a solution containing 0.02M Tris HCl, pH 7.5, 10 mM EDTA, 20% sucrose, and incubating for 10 minutes on ice. The cells are then pelleted by centrifugation at 4,000×g for 15 min at 4° G. After the supernatant is removed, the cell pellets are resuspended in 10 mL of Buffer A1 (0.01M Tris HCl, pH 7.5, 1 mM EDTA, 14 mM β-mercaptoethanol—"βME"), and incubated on ice for 10 minutes. The cells are again pelleted at 4,000×g for 15 minutes at 4° G. After removal of the clear supernatant (periplasmic fraction I), the cell pellets are resuspended in Buffer A1, incubated on ice for 10 minutes, and again centrifuged at 4,000×g for 15 minutes at 4° G. The clear supernatant (periplasmic fraction II) is removed, and the cell pellet resuspended in 5 mL of Buffer T2 (0.02M Tris HCI, pH 7.5, 14 mM βME, 1 mM EDTA, 1 mM PMSF). In order to disrupt the cells, the suspension (5 mL) and 7.5 mL of Dyno-mill lead-free acid washed glass beads (0.10–0.15 mm diameter) (available from Glen-Mills, Inc.) are placed in a Falcon tube and vortexed at top speed for two minutes, followed by cooling for at least 2 min on ice. The vortexing-cooling procedure is repeated another four times. After vortexing, the slurry is filtered through a sintered glass funnel using low suction, the glass beads washed twice with Buffer A2, and the filtrate and washes combined.

The insoluble fraction of the crude extract is collected by centrifugation at 20,000×g for 15 min at 4° C., washed twice with 10 mL Buffer A2, and resuspended in 5 mL of MILLI-Q water.

A fraction containing the HCV protease is isolated from the insoluble material by adding to the suspension NaOH (2M) and NaCl (2M) to yield a final concentation of 20 mM each, vortexing the mixture for 1 minute, centrifuging it 20,000×g for 20 min at 4° C., and retaining the supernatant.

The partially purified protease is then purified by SDS-PAGE. The protease may be identified by western blot, and the band excised from the gel. The protease is then eluted from the band, and analyzed to confirm its amino acid sequence. N-terminal sequences may be analyzed using an automated amino acid sequencer, while C-terminal sequences may be analyzed by automated amino acid sequencing of a series of tryptic fragments.

EXAMPLE 7
(Preparation of Yeast Expression Vector)

(A) P650 (SOD/Protease Fusion)

This vector contains HCV sequence, which includes the wild-type full-length HCV protease coding sequence, fused at the 5' end to a SOD coding sequence. Two fragments, a 441 bp EcoRI/BglII fragment from clone 11b and a 1471 bp BglII/EcoRI fragment from expression vector P500, were used to reconstruct a wild-type, full-length HCV protease coding sequence. These two fragments were ligated together with an EcoRI digested pS356 vector to produce an expression cassette. The expression cassette encodes the ADH2/GAPDH hybrid yeast promoter, human SOD, the HCV protease, and a GAPDH transcription terminator. The resulting vector was digested with BamHI and a 4052 bp fragment was isolated. This fragment was ligated to the BamHI digested pAB24 vector to produce p650. p650 expresses a polyprotein containing, from its amino terminal end, amino acids 1–154 of hSOD, an oligopeptide -Asn-Leu-Gly-Ile-Arg-, and amino acids 819 to 1458 of HCV-1, as shown in FIG. 17 of WO 90/11089, published 4 Oct. 1990.

Clone 11b was isolated from the genomic library of HCV cDNA, ATCC accession no. 40394, as described above in Example 3A, using a hybridization probe having the following sequence:

5' CAC CTA TGT TTA TAA CCA TCT CAC TCC TCT 3' (SEQ ID NO: 54).

This procedure is also described in EPO Pub. No. 318 216, Example IV.A.17.

The vector pS3EF, which is a pBR322 derivative, contains the ADH2/GAPDH hybrid yeast promoter upstream of the human superoxide dimutase gene, an adaptor, and a downstream yeast effective transcription terminator. A similar expression vector containing these control elements and the superoxide dismutase gene is described in Cousens et al. (1987) *Gene* 61: 265, and in copending application EPO 196,056, published Oct. 1, 1986. pS3EF, however, differs from that in Cousens et al. in that the heterologous proinsulin gene and the immunoglobulin hinge are deleted, and $Gln_{154}$ of SOD is followed by an adaptor sequence which contains an EcoRI site. The sequence of the adaptor is:

5' AAT TTG GGA ATT CCA TAA TTA ATT AAG 3'
(SEQ ID NO: 55)
3' AC CCT TAA GGT ATT AAT TAA TTC AGCT 5'
(SEQ ID NO: 56)

The EcoRI site facilitates the insertion of heterologous sequences. Once inserted into pS3EF, a SOD fusion is expressed which contains an oligopeptide that links SOD to the heterologous sequences. pS3EF is exactly the same as pS356 except that pS356 contains a different adaptor. The sequence of the adaptor is shown below:

5' AAT TTG GGA ATT CCA TAA TGA G 3'(SEQ ID NO: 57)
3' AC CCT TAA GGT ATT ACT CAG CT 5'
(SEQ ID NO: 58)

pS356, ATCC accession no. 67683, is deposited as set forth below.

Plasmid pAB24 is a yeast shuttle vector, which contains pBR322 sequences, the complete 2μ sequence for DNA replication in yeast (Broach (1981) in: *Molecular Biology of the Yeast Saccharomyces*, Vol. 1, p. 445, Cold spring Harbor Press.) and the yeast $LEU^{2d}$ gene derived from plasmid pC1/1, described in EPO Pub. No. 116 201. Plasmid pAB24 was constructed by digesting YEp24 with EcoRI and re-ligating the vector to remove the partial 2 micron sequences. The resulting plasmid, YEp24deltaRI was linearized with ClaI and ligated with the complete 2 micron plasmid which had been linearized with ClaI. The resulting plasmid, pCBou, was then digested with XbaI, and the 8605 bp vector fragment was gel isolated. This isolated XbaI fragment was ligated with a 4460 bp XbaI fragment containing the $LEU^{2d}$ gene isolated from pC1/1; the orientation of $LEU^{2d}$ gene is in the same direction as the URA3 gene.

*S. cerevisae*, 2150-2-3 (pAB24GAP-env2), accession no. 20827, is deposited with the American Type Culture Collection as set forth below. The plasmid pAB24GAP-env2 can be recovered from the yeast cells by known techniques.

The GAP-env2 expression cassette can be removed by digesting pAB24GAP-env2 with BamHI. pAB24 is recovered by religating the vector without the BarnHI insert.

EXAMPLE 8
(Yeast Expression of SOD-Protease Fusion Protein)
p650 was transformed in *S. cerevisae* strain JSC310, Mata, leu2, ura3-52, prb1-1122, pep4-3, prc1-407, cir°:

DM15 (g418 resistance). The transformation is as described by Hinnen et al. (1978) *Proc Natl Acad Sci USA* 75: 1929. The transformed cells were selected on ura- plates with 8% glucose. The plates were incubated at 30° C. for 4–5 days. The tranformants were further selected on leu- plates with 8% glucose putatively for high numbers of the p650 plasmid. Colonies from the leu- plates were inoculated into leu- medium with 3% glucose. These cultures were shaken at 30° C. for 2 days and then diluted 1/20 into YEPD medium with 2% glucose and shaken for 2 more days at 30° C.

*S. cerevisae* JSC310 contains DM15 DNA, described in EPO Pub. No. 340 986, published 8 Nov. 1989. This DM15 DNA enhances ADH2 regulated expression of heterologous proteins. pDM15, accession no. 40453, is deposited with the American Type Culture Collection as set forth below.

EXAMPLE 9
(Yeast Ubiquitin Expression of Mature HCV Protease)

Mature HCV protease is prepared by cleaving vector C7fC20cC300C200 with EcoRI to obtain a 2 Kb coding sequence, and inserting the sequence with the appropriate linkers into a ubiquitin expression vector, such as that described in WO 88/02406, published 7 Apr. 1988, or U.S. Ser. No. 7/390,599 filed 7 Aug. 1989, incorporated herein by reference. Mature HCV protease is recovered upon expression of the vector in suitable hosts, particularly yeast. Specifically, the yeast expression protocol described in Example 8 is used to express a ubiquitin/HCV protease vector.

EXAMPLE 10
Preparation of an In-Vitro Expression Vector)
(A) pGEM®-3Z/Yellow Fever Leader Vector Four synthetic DNA fragments were annealed and ligated** together to create a EcoRI/SacI Yellow Fever leader, which was ligated to a EcoRI/SacI digested pGEM®-3Z vector from Promega®. The sequence of the four fragments are listed below:

YFK-1:
5' AAT TCG TAA ATC CTG TGT GCT AAT TGA GGT GCA TTG GTC TGC

AAA TCG AGT TGC TAG GCA ATA AAC ACA TT (SEQ ID NO: 59)

YFK-2:
5' TAT TGC CTA GCA ACT CGA TTT GCA GAC CAA TGC ACC TCA ATT

AGC ACA CAG GAT TTA CG 3' (SEQ ID NO: 60)

YFK-3:
5' TGG ATT AAT TTT AAT CGT TCG TTG AGC GAT TAG CAG AGA ACT

GAC CAG AAC ATG TCT GAG CT 3' (SEQ ID NO: 61)

YFK-4:
5' CAG ACA TGT TCT GGT CAG TTC TCT GCT AAT CGC TCA ACG AAC

GAT TAA AAT TAA TCC AAA TGT GTT 3' (SEQ ID NO: 62)

For in-vitro translation of the HCV protease, the new pGEM®-3Z/Yellow Fever leader vector was digested with BamHI and blunted with Klenow.

(B) PvuII Construct from p6000

A clone p6000 was constructed from sequences available from the genomic library of HCV cDNA, ATCC accession no. 40394. The HCV encoding DNA sequence of p6000 is identical to nucleotide -275 to nucleotide 6372 of FIG. 17 of WO 90/11089, published 4 Oct. 1990. p6000 was digested with PvuII, and from the digest, a 2,864 bp fragment was isolated. This 2,864 bp fragment was ligated to the prepared pGEM®-3Z/Yellow Fever leader vector fragment, described above.

EXAMPLE 11

(In-Vitro Expression of HCV Protease)

(A) Transcription

The pGEM®-3Z/Yellow Fever leader/PvuII vector was linearized with XbaI and transcribed using the materials and protocols from Promega's Riboprobe® Gemini II Core system.

(B) Translation

The RNA produced by the above protocol was translated using Promega's rabbit reticulocyte lysate, minus methionine, canine pancreatic microsomal membranes, as well as, other necessary materials and instructions from Promega.

Deposited Biological Materials:

The following materials were deposited with the American Type Culture Collection (ATCC), 12301 Parldawn Dr., Rockville, Ma.:

| Name | Deposit Date | Accession No. |
|---|---|---|
| *E. coli* D1210, cf1SODp600 | 23 Mar 1990 | 68275 |
| Cf1/S-1-1 in *E. coli* D1210 | 11 May 1989 | 67967 |
| Bacteriophage λ-gt11 cDNA library | 01 Dec 1987 | 40394 |
| *E. coli* HB101, pS356 | 29 Apr 1988 | 67683 |
| plasmid DNA, pDM15 | 05 May 1988 | 40453 |
| *S. cerevisae,* 2150-2-3 (pAB24-GAP-env2) | 23 Dec 1986 | 20827 |

The above materials have been deposited with the ATCC under the accession numbers indicated. These deposits will be maintained under the terms of the Budapest Treaty on the International Recognition of the Deposit of Microorganisms for purposes of Patent Procedure. These deposits are provided as a convenience to those of skill in the art, and are not an admission that a deposit is required under 35 U.S.C. §112. The polynucleotide sequences contained in the deposited materials, as well as the amino acid sequence of the polypeptides encoded thereby, are incorporated herein by reference and are controlling in the event of any conflict with the sequences described herein. A license may be required to make, use or sell the deposited materials, and no such license is granted hereby.

What is claimed:

1. A method of making a purified hepatitis C virus (HCV) NS3 protease or active truncation analog comprising the steps of:

(a) transforming a suitable host cell with an expression vector comprising (i) a polynucleotide encoding an HCV NS3 protease or active truncation analog; and (ii) transcriptional and translational regulatory sequences functional in said host cell operably linked to said polynucleotide;

(b) incubating said host cell to obtain expression of said protease or active truncation analog; and (c) purifying said HCV NS3 protease or active truncation analog.

2. The method of claim 1 wherein said host cell is selected from an *E. coli*, yeast, insect or mammalian host cell.

3. The method of claim 1 wherein said polynucleotide encodes the HCV protease of SEQ ID NO: 1.

4. The method of claim 1 wherein said HCV NS3 protease or active truncation analog is from the HCV-1 isolate.

5. The method of claim 2 wherein said host cell is a yeast cell.

6. A method of making a purified fusion protein containing a hepatitis C virus (HCV) NS3 protease or active truncation analog comprising the steps of:

(a) transforming a suitable host cell with an expression vector comprising (i) a polynucleotide encoding an HCV NS3 protease or active truncation analog; (ii) transcriptional and translational regulatory sequences functional in said host cell operably linked to said polynucleotide, and (iii) a nucleotide sequence encoding a fusion partner, linked to said HCV NS3 protease or active truncation analog-encoding polynucleotide, to form a fusion protein upon expression;

(b) incubating said host cell to obtain expression of said fusion protein containing said protease or active truncation analog; and (c) purifying said fusion protein containing said HCV NS3 protease or active truncation analog.

7. The method of claim 6 wherein said fusion partner is selected from the group consisting of hSOD, yeast α-factor, IL-2S, ubiquitin, β-galactosidase, β-lactamase, horseradish peroxidase, glucose oxidase, and urease.

8. The method of claim 6 wherein said host cell is selected from an *E. coli*, yeast, insect or mammalian host cell.

9. The method of claim 7 wherein said polynucleotide encodes the HCV protease of SEQ ID NO: 1.

10. The method of claim 6 wherein said HCV NS3 protease or active truncation analog is from the HCV-1 isolate.

11. The method of claim 7 wherein said host cell is a yeast cell.

12. The method of claim 6 wherein said host cell is a yeast cell and said fusion partner is selected from the group consisting of ubiquitin, hSOD and yeast α-factor.

* * * * *

SEQUENCE LISTING ( 1 ) GENERAL INFORMATION:

( i i i ) NUMBER OF SEQUENCES: 86

( 2 ) INFORMATION FOR SEQ ID NO:1:

( i ) SEQUENCE CHARACTERISTICS:
( A ) LENGTH: 202 amino acids
( B ) TYPE: amino acid
( C ) STRANDEDNESS: single
( D ) TOPOLOGY: linear ( x i ) SEQUENCE DESCRIPTION: SEQ ID NO:1:

```
Arg Arg Gly Arg Glu Ile Leu Leu Gly Pro Ala Asp Gly Met Val Ser
1               5                   10                  15

Lys Gly Trp Arg Leu Leu Ala Pro Ile Thr Ala Tyr Ala Gln Gln Thr
            20                  25                  30

Arg Gly Leu Leu Gly Cys Ile Ile Thr Ser Leu Thr Gly Arg Asp Lys
        35                  40                  45

Asn Gln Val Glu Gly Glu Val Gln Ile Val Ser Thr Ala Ala Gln Thr
    50                  55                  60

Phe Leu Ala Thr Cys Ile Asn Gly Val Cys Trp Thr Val Tyr His Gly
65                  70                  75                  80

Ala Gly Thr Arg Thr Ile Ala Ser Pro Lys Gly Pro Val Ile Gln Met
                85                  90                  95

Tyr Thr Asn Val Asp Gln Asp Leu Val Gly Trp Pro Ala Ser Gln Gly
            100                 105                 110

Thr Arg Ser Leu Thr Pro Cys Thr Cys Gly Ser Ser Asp Leu Tyr Leu
        115                 120                 125

Val Thr Arg His Ala Asp Val Ile Pro Val Arg Arg Arg Gly Asp Ser
    130                 135                 140
```

```
Arg  Gly  Ser  Leu  Leu  Ser  Pro  Arg  Pro  Ile  Ser  Tyr  Leu  Lys  Gly  Ser
145                      150                      155                      160

Ser  Gly  Gly  Pro  Leu  Leu  Cys  Pro  Ala  Gly  His  Ala  Val  Gly  Ile  Phe
                    165                      170                      175

Arg  Ala  Ala  Val  Cys  Thr  Arg  Gly  Val  Ala  Lys  Ala  Val  Asp  Phe  Ile
                    180                      185                      190

Pro  Val  Glu  Asn  Leu  Glu  Thr  Thr  Met  Arg
               195                 200
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Cys  Trp  Thr  Val  Tyr  His  Gly  Ala  Gly
1                        5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Asp  Gln  Asp  Leu  Gly  Trp  Pro  Ala  Pro
1                        5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Leu  Lys  Gly  Ser  Ser  Gly  Gly  Pro  Leu
1                        5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Phe  His  Thr  Met  Trp  His  Val  Thr  Arg
1                        5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
     Lys  Glu  Asp  Leu  Val  Ala  Tyr  Gly  Gly
     1                  5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
     Pro  Ser  Gly  Thr  Ser  Gly  Ser  Pro  Ile
     1                  5
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
     Phe  His  Thr  Leu  Trp  His  Thr  Thr  Lys
     1                  5
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
     Lys  Glu  Asp  Arg  Leu  Cys  Tyr  Gly  Gly
     1                  5
```

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
     Pro  Thr  Gly  Thr  Ser  Gly  Ser  Pro  Ile
     1                  5
```

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

```
     Phe  His  Thr  Leu  Trp  His  Thr  Thr  Arg
     1                  5
```

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single ( D ) TOPOLOGY: linear ( x i ) SEQUENCE DESCRIPTION: SEQ ID NO:12:

Lys Glu Asp Arg Val Thr Tyr Gly Gly
1               5

( 2 ) INFORMATION FOR SEQ ID NO:13:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:13:

Pro Ile Gly Thr Ser Gly Ser Pro Ile
1               5

( 2 ) INFORMATION FOR SEQ ID NO:14:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:14:

Phe His Thr Leu Trp His Thr Thr Lys
1               5

( 2 ) INFORMATION FOR SEQ ID NO:15:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:15:

Lys Glu Asp Arg Leu Cys Tyr Gly Gly
1               5

( 2 ) INFORMATION FOR SEQ ID NO:16:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:16:

Pro Thr Gly Thr Ser Gly Ser Pro Ile
1               5

( 2 ) INFORMATION FOR SEQ ID NO:17:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:17:

Thr Ala Gly His Cys
1               5

( 2 ) INFORMATION FOR SEQ ID NO:18:

(i) SEQUENCE CHARACTERISTICS:
  (A) LENGTH: 7 amino acids
  (B) TYPE: amino acid
  (C) STRANDEDNESS: single
  (D) TOPOLOGY: linear (xi) SEQUENCE DESCRIPTION: SEQ ID NO:18:

Asn Asn Asp Tyr Gly Ile Ile
1               5

(2) INFORMATION FOR SEQ ID NO:19:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:19:

Gly Asp Ser Gly Gly Ser Leu
1               5

(2) INFORMATION FOR SEQ ID NO:20:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:20:

Thr Ala Gly His Cys
1               5

(2) INFORMATION FOR SEQ ID NO:21:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:21:

Gly Asn Asp Arg Ala Trp Val
1               5

(2) INFORMATION FOR SEQ ID NO:22:

(i) SEQUENCE CHARACTERISTICS:
    (A) LENGTH: 7 amino acids
    (B) TYPE: amino acid
    (C) STRANDEDNESS: single
    (D) TOPOLOGY: linear (xi) SEQUENCE DESCRIPTION: SEQ ID NO:22:

Gly Asp Ser Gly Gly Ser Trp
1               5

(2) INFORMATION FOR SEQ ID NO:23:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:23:

Ser Ala Ala His Cys
1               5

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

Asn Asn Asp Ile Met Leu Ile
1               5

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

Gly Asp Ser Gly Gly Pro Val
1               5

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

Thr Ala Ala His Cys
1               5

( 2 ) INFORMATION FOR SEQ ID NO:27:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:27:

Asn Asn Asp Ile Thr Leu Leu
1               5

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:28:

Gly Asp Ser Gly Gly Pro Leu
1               5

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:29:

Thr Ala Ala His Cys
1               5

( 2 ) INFORMATION FOR SEQ ID NO:30:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:30:

Gly Tyr Asp Ile Ala Leu Leu
1               5

( 2 ) INFORMATION FOR SEQ ID NO:31:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:31:

Gly Asp Ser Gly Gly Pro Leu
1               5

( 2 ) INFORMATION FOR SEQ ID NO:32:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:32:

Thr Val Tyr His Gly
1               5

( 2 ) INFORMATION FOR SEQ ID NO:33:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:33:

Ser Ser Asp Leu Tyr Leu Val
1               5

( 2 ) INFORMATION FOR SEQ ID NO:34:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:34:

Gly Ser Ser Gly Gly Pro Leu
1               5

( 2 ) INFORMATION FOR SEQ ID NO:35:

( i ) SEQUENCE CHARACTERISTICS:
      ( A ) LENGTH: 75 amino acids (B) TYPE: amino acid
(C) STRANDEDNESS: single
(D) TOPOLOGY: linear (xi) SEQUENCE DESCRIPTION: SEQ ID NO:35:

```
Gln Ile Phe Val Lys Thr Leu Thr Gly Lys Thr Ile Thr Leu Glu Val
1               5                   10                  15
Glu Ser Ser Asp Thr Ile Asp Asn Val Lys Ser Lys Ile Gln Asp Lys
            20                  25                  30
Glu Gly Ile Pro Pro Asp Gln Gln Arg Leu Ile Phe Ala Gly Lys Gln
        35                  40                  45
Leu Glu Asp Gly Arg Thr Leu Ser Asp Tyr Asn Ile Gln Lys Glu Ser
    50                  55                  60
Thr Leu His Leu Val Leu Arg Leu Arg Gly Gly
65                  70                  75
```

(2) INFORMATION FOR SEQ ID NO:36:

(i) SEQUENCE CHARACTERISTICS:
(A) LENGTH: 28 amino acids
(B) TYPE: amino acid
(C) STRANDEDNESS: single
(D) TOPOLOGY: linear (xi) SEQUENCE DESCRIPTION: SEQ ID NO:36:

```
Val Ser Ala Arg Arg Gly Arg Glu Ile Leu Leu Gly Ala Ile Leu Arg
1               5                   10                  15
Arg His Val Gly Pro Val Ser Cys Gln Arg Gly Tyr
            20                  25
```

(2) INFORMATION FOR SEQ ID NO:37:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:37:

GATCCTGGAA TTCTGATAAG ACCTTAAGAC TATTTTAA                         38

(2) INFORMATION FOR SEQ ID NO:38:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:38:

GATCCTGAAT TCCTGATAA                                              19

(2) INFORMATION FOR SEQ ID NO:39:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:39:

GACTTAAGGA CTATTTTAA                                              19

(2) INFORMATION FOR SEQ ID NO:40:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

GATCCGAATT CTGTGATAA     19

( 2 ) INFORMATION FOR SEQ ID NO:41:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:41:

GCTTAAGACA CTATTTTAA     19

( 2 ) INFORMATION FOR SEQ ID NO:42:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:42:

GATCCTGGAA TTCTGATAA     19

( 2 ) INFORMATION FOR SEQ ID NO:43:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:43:

GACCTTAAGA CTATTTTAA     19

( 2 ) INFORMATION FOR SEQ ID NO:44:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:44:

ATCAGGACCG GGGTGAGAAC AATTACCACT     30

( 2 ) INFORMATION FOR SEQ ID NO:45:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:45:

AAGCCACCGT GTGCGCTAGG GCTCAAGCCC     30

( 2 ) INFORMATION FOR SEQ ID NO:46:

( i ) SEQUENCE CHARACTERISTICS:
    ( A ) LENGTH: 31 base pairs (B) TYPE: nucleic acid
(C) STRANDEDNESS: single
(D) TOPOLOGY: linear (xi) SEQUENCE DESCRIPTION: SEQ ID NO:46:

AGCAGACAAG GGGCCTCCTA GGGTGCATAA T 31

(2) INFORMATION FOR SEQ ID NO:47:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:47:

TGCATCAATG GGGTGTGCTG G 21

(2) INFORMATION FOR SEQ ID NO:48:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:48:

AGAGACAACC ATGAGGTCCC CGGTGTTC 28

(2) INFORMATION FOR SEQ ID NO:49:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:49:

CTGTTGTGCC CCGCGGCAGC C 21

(2) INFORMATION FOR SEQ ID NO:50:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:50:

CCCGAGCAAG ATCTCCCGGC CC 22

(2) INFORMATION FOR SEQ ID NO:51:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:51:

CCCGGCTGCA TAAGCAGTCG ACTTGGA 27

(2) INFORMATION FOR SEQ ID NO:52:

(i) SEQUENCE CHARACTERISTICS:
(A) LENGTH: 37 base pairs
(B) TYPE: nucleic acid
(C) STRANDEDNESS: single ( D ) TOPOLOGY: linear ( i x ) FEATURE:
                    ( A ) NAME/KEY: CDS
                    ( B ) LOCATION: 2..37

( x i ) SEQUENCE DESCRIPTION: SEQ ID NO:52:

```
C ATG GAC TAC AAA GAC GAT GAC GAT AAA GGC CGG GAG           37
  Met Asp Tyr Lys Asp Asp Asp Asp Lys Gly Arg Glu
  1               5                   10
```

( 2 ) INFORMATION FOR SEQ ID NO:53:

( i ) SEQUENCE CHARACTERISTICS:
                    ( A ) LENGTH: 12 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO:53:

```
Met Asp Tyr Lys Asp Asp Asp Asp Lys Gly Arg Glu
1               5                   10
```

( 2 ) INFORMATION FOR SEQ ID NO:54:

( i ) SEQUENCE CHARACTERISTICS:
                    ( A ) LENGTH: 30 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:54:

CACCTATGTT TATAACCATC TCACTCCTCT                            30

( 2 ) INFORMATION FOR SEQ ID NO:55:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:55:

AATTTGGGAA TTCCATAATT AATTAAG                               27

( 2 ) INFORMATION FOR SEQ ID NO:56:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:56:

TCGACTTAAT TAATTATGGA ATTCCCA                               27

( 2 ) INFORMATION FOR SEQ ID NO:57:

( i ) SEQUENCE CHARACTERISTICS:
                    ( A ) LENGTH: 22 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:57:

AATTTGGGAA TTCCATAATG AG                                    22

( 2 ) INFORMATION FOR SEQ ID NO:58:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

TCGACTCATT ATGGAATTCC CA      22

( 2 ) INFORMATION FOR SEQ ID NO:59:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

AATTCGTAAA TCCTGTGTGC TAATTGAGGT GCATTGGTCT GCAAATCGAG TTGCTAGGCA      60

ATAAACACAT T      71

( 2 ) INFORMATION FOR SEQ ID NO:60:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

TATTGCCTAG CAACTCGATT TGCAGACCAA TGCACCTCAA TTAGCACACA GGATTTACG      59

( 2 ) INFORMATION FOR SEQ ID NO:61:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

TGGATTAATT TTAATCGTTC GTTGAGCGAT TAGCAGAGAA CTGACCAGAA CATGTCTGAG      60

CT      62

( 2 ) INFORMATION FOR SEQ ID NO:62:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

CAGACATGTT CTGGTCAGTT CTCTGCTAAT CGCTCAACGA ACGATTAAAA TTAATCCAAA      60

TGTGTT      66

( 2 ) INFORMATION FOR SEQ ID NO:63:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:63:

-continued

```
        Trp Thr Val Tyr His Gly Ala Gly Thr Arg Thr
        1               5                   10
```

( 2 ) INFORMATION FOR SEQ ID NO:64:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( x i ) SEQUENCE DESCRIPTION: SEQ ID NO:64:

```
        Leu Lys Gly Ser Ser Gly Gly Pro Leu
        1               5
```

( 2 ) INFORMATION FOR SEQ ID NO:65:

( i ) SEQUENCE CHARACTERISTICS:
( A ) LENGTH: 202 amino acids
( B ) TYPE: amino acid
( C ) STRANDEDNESS: single
( D ) TOPOLOGY: linear ( x i ) SEQUENCE DESCRIPTION: SEQ ID NO:65:

```
Arg Arg Gly Arg Glu Ile Leu Leu Gly Pro Ala Asp Gly Met Val Ser
1               5                   10                  15

Lys Gly Trp Arg Leu Leu Ala Pro Ile Thr Ala Tyr Ala Gln Gln Thr
                20                  25                  30

Arg Gly Leu Leu Gly Cys Ile Ile Thr Ser Leu Thr Gly Arg Asp Lys
                35                  40                  45

Asn Gln Val Glu Gly Glu Val Gln Ile Val Ser Thr Ala Ala Gln Thr
        50                  55                  60

Phe Leu Ala Thr Cys Ile Asn Gly Val Cys Trp Thr Val Tyr His Gly
65                  70                  75                  80

Ala Gly Thr Arg Thr Ile Ala Ser Pro Lys Gly Pro Val Ile Gln Met
                        85                  90                  95

Tyr Thr Asn Val Asp Gln Asp Leu Val Gly Trp Pro Ala Ser Gln Gly
                100                 105                 110

Thr Arg Ser Leu Thr Pro Cys Thr Cys Gly Ser Ser Asp Leu Tyr Leu
                115                 120                 125

Val Thr Arg His Ala Asp Val Ile Pro Val Arg Arg Arg Gly Asp Ser
                130                 135                 140

Arg Gly Ser Leu Leu Ser Pro Arg Pro Ile Ser Tyr Leu Lys Gly Ser
145                 150                 155                 160

Ser Gly Gly Pro Leu Leu Cys Pro Ala Gly His Ala Val Gly Ile Phe
                        165                 170                 175

Arg Ala Ala Val Cys Thr Arg Gly Val Ala Lys Ala Val Asp Phe Ile
                180                 185                 190

Pro Val Glu Asn Leu Glu Thr Thr Met Arg
                195                 200
```

( 2 ) INFORMATION FOR SEQ ID NO:66:

( i ) SEQUENCE CHARACTERISTICS:
( A ) LENGTH: 299 amino acids
( B ) TYPE: amino acid
( C ) STRANDEDNESS: single
( D ) TOPOLOGY: linear ( x i ) SEQUENCE DESCRIPTION: SEQ ID NO:66:

```
Gly Thr Tyr Val Tyr Asn His Leu Thr Pro Leu Arg Asp Trp Ala His
```

```
             1               5                           10                          15

Asn   Gly   Leu   Arg   Asp   Leu   Ala   Val   Ala   Val   Glu   Pro   Val   Val   Phe   Ser
                              20                          25                          30

Gln   Met   Glu   Thr   Lys   Leu   Ile   Thr   Trp   Gly   Ala   Asp   Thr   Ala   Ala   Cys
                        35                          40                          45

Gly   Asp   Ile   Ile   Asn   Gly   Leu   Pro   Val   Ser   Ala   Arg   Arg   Gly   Arg   Glu
                        50                          55                          60

Ile   Leu   Leu   Gly   Pro   Ala   Asp   Gly   Met   Val   Ser   Lys   Gly   Trp   Arg   Leu
            65                          70                          75                          80

Leu   Ala   Pro   Ile   Thr   Ala   Tyr   Ala   Gln   Gln   Thr   Arg   Gly   Leu   Leu   Gly
                                    85                          90                          95

Cys   Ile   Ile   Thr   Ser   Leu   Thr   Gly   Arg   Asp   Lys   Asn   Gln   Val   Glu   Gly
                              100                         105                         110

Glu   Val   Gln   Ile   Val   Ser   Thr   Ala   Ala   Gln   Thr   Phe   Leu   Ala   Thr   Cys
                              115                         120                         125

Ile   Ile   Asn   Gly   Val   Cys   Trp   Thr   Val   Tyr   His   Gly   Ala   Gly   Thr   Arg
                        130                         135                         140

Thr   Ile   Ala   Ser   Pro   Lys   Gly   Pro   Val   Ile   Gln   Met   Tyr   Thr   Asn   Val
            145                         150                         155                         160

Asp   Gln   Asp   Leu   Val   Gly   Trp   Pro   Ala   Ser   Gln   Gly   Thr   Arg   Ser   Leu
                                    165                         170                         175

Thr   Pro   Cys   Thr   Cys   Gly   Ser   Ser   Asp   Leu   Tyr   Leu   Val   Thr   Arg   His
                              180                         185                         190

Ala   Asp   Val   Ile   Pro   Val   Arg   Arg   Arg   Gly   Asp   Ser   Arg   Gly   Ser   Leu
                              195                         200                         205

Leu   Ser   Pro   Arg   Pro   Ile   Ser   Tyr   Leu   Lys   Gly   Ser   Ser   Gly   Gly   Pro
                              210                         215                         220

Leu   Leu   Cys   Pro   Ala   Gly   His   Ala   Val   Gly   Ile   Phe   Arg   Ala   Ala   Val
            225                         230                         235                         240

Cys   Thr   Arg   Gly   Val   Ala   Lys   Ala   Val   Asp   Phe   Ile   Pro   Val   Glu   Asn
                                    245                         250                         255

Leu   Glu   Thr   Thr   Met   Arg   Ser   Pro   Val   Phe   Thr   Asp   Asn   Ser   Ser   Pro
                              260                         265                         270

Pro   Val   Val   Pro   Gln   Ser   Phe   Gln   Val   Ala   His   Leu   His   Ala   Pro   Thr
                              275                         280                         285

Gly   Ser   Gly   Lys   Ser   Thr   Lys   Val   Pro   Ala   Ala
                              290                         295
```

( 2 ) INFORMATION FOR SEQ ID NO:67:

( i ) SEQUENCE CHARACTERISTICS:
        ( A ) LENGTH: 199 amino acids
        ( B ) TYPE: amino acid
        ( C ) STRANDEDNESS: single
        ( D ) TOPOLOGY: linear ( x i ) SEQUENCE DESCRIPTION: SEQ ID NO:67:

```
            Gly   Thr   Tyr   Val   Tyr   Asn   His   Leu   Thr   Pro   Leu   Arg   Asp   Trp   Ala   His
            1                           5                           10                          15

Asn   Gly   Leu   Arg   Asp   Leu   Ala   Val   Ala   Val   Glu   Pro   Val   Val   Phe   Ser
                              20                          25                          30

Gln   Met   Glu   Thr   Lys   Leu   Ile   Thr   Trp   Gly   Ala   Asp   Thr   Ala   Ala   Cys
                        35                          40                          45

Gly   Asp   Ile   Ile   Asn   Gly   Leu   Pro   Val   Ser   Ala   Arg   Arg   Gly   Arg   Glu
                        50                          55                          60

Ile   Leu   Leu   Gly   Pro   Ala   Asp   Gly   Met   Val   Ser   Lys   Gly   Trp   Arg   Leu
```

|     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- |

Leu Ala Pro Ile Thr Ala Tyr Ala Gln Gln Thr Arg Gly Leu Leu Gly
                    85                  90                    95

Cys Ile Ile Thr Ser Leu Thr Gly Arg Asp Lys Asn Gln Val Glu Gly
            100                 105                 110

Glu Val Gln Ile Val Ser Thr Ala Ala Gln Thr Phe Leu Ala Thr Cys
            115                 120                 125

Ile Ile Asn Gly Val Cys Trp Thr Val Tyr His Gly Ala Gly Thr Arg
        130                 135                 140

Thr Ile Ala Ser Pro Lys Gly Pro Val Ile Gln Met Tyr Thr Asn Val
145                 150                 155                 160

Asp Gln Asp Leu Val Gly Trp Pro Ala Ser Gln Gly Thr Arg Ser Leu
                165                 170                 175

Thr Pro Cys Thr Cys Gly Ser Ser Asp Leu Tyr Leu Val Thr Arg His
            180                 185                 190

Ala Asp Val Ile Pro Val Arg
            195

( 2 ) INFORMATION FOR SEQ ID NO:68:

( i ) SEQUENCE CHARACTERISTICS:
      ( A ) LENGTH: 299 amino acids
      ( B ) TYPE: amino acid
      ( C ) STRANDEDNESS: single
      ( D ) TOPOLOGY: linear ( x i ) SEQUENCE DESCRIPTION: SEQ ID NO:68:

Gly Thr Tyr Val Tyr Asn His Leu Thr Pro Leu Arg Asp Trp Ala His
1               5                   10                  15

Asn Gly Leu Arg Asp Leu Ala Val Ala Val Glu Pro Val Val Phe Ser
            20                  25                  30

Gln Met Glu Thr Lys Leu Ile Thr Trp Gly Ala Asp Thr Ala Ala Cys
        35                  40                  45

Gly Asp Ile Ile Asn Gly Leu Pro Val Ser Ala Arg Arg Gly Arg Glu
    50                  55                  60

Ile Leu Leu Gly Pro Ala Asp Gly Met Val Ser Lys Gly Trp Arg Leu
65                  70                  75                  80

Leu Ala Pro Ile Thr Ala Tyr Ala Gln Gln Thr Arg Gly Leu Leu Gly
                85                  90                  95

Cys Ile Ile Thr Ser Leu Thr Gly Arg Asp Lys Asn Gln Val Glu Gly
            100                 105                 110

Glu Val Gln Ile Val Ser Thr Ala Ala Gln Thr Phe Leu Ala Thr Cys
            115                 120                 125

Ile Ile Asn Gly Val Cys Trp Thr Val Tyr His Gly Ala Gly Thr Arg
        130                 135                 140

Thr Ile Ala Ser Pro Lys Gly Pro Val Ile Gln Met Tyr Thr Asn Val
145                 150                 155                 160

Asp Gln Asp Leu Val Gly Trp Pro Ala Ser Gln Gly Thr Arg Ser Leu
                165                 170                 175

Thr Pro Cys Thr Cys Gly Ser Ser Asp Leu Tyr Leu Val Thr Arg His
            180                 185                 190

Ala Asp Val Ile Pro Val Arg Arg Arg Gly Asp Ser Arg Gly Ser Leu
            195                 200                 205

Leu Ser Pro Arg Pro Ile Ser Tyr Leu Lys Gly Ser Ser Gly Gly Pro
            210                 215                 220

Leu Leu Cys Pro Ala Gly His Ala Val Gly Ile Phe Arg Ala Ala Val

```
                  225                           230                           235                           240
           Cys  Thr  Arg  Gly  Val  Ala  Lys  Ala  Val  Asp  Phe  Ile  Pro  Val  Glu  Asn
                               245                           250                           255

Leu  Glu  Thr  Thr  Met  Arg  Ser  Pro  Val  Phe  Thr  Asp  Asn  Ser  Ser  Pro
                               260                           265                           270

Pro  Val  Val  Pro  Gln  Ser  Phe  Gln  Val  Ala  His  Leu  His  Ala  Pro  Thr
                               275                           280                           285

Gly  Ser  Gly  Lys  Ser  Thr  Lys  Val  Pro  Ala  Ala
                               290                           295
```

( 2 ) INFORMATION FOR SEQ ID NO:69:

( i ) SEQUENCE CHARACTERISTICS:
        ( A ) LENGTH: 2064 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 7..2064

( x i ) SEQUENCE DESCRIPTION: SEQ ID NO:69:

```
ATTCGG GGC ACC TAT GTT TAT AAC CAT CTC ACT CCT CTT CGG GAC TGG              48
       Gly Thr Tyr Val Tyr Asn His Leu Thr Pro Leu Arg Asp Trp
        1           5                  10

GCG CAC AAC GGC TTG CGA GAT CTG GCC GTG GCT GTA GAG CCA GTC GTC             96
Ala His Asn Gly Leu Arg Asp Leu Ala Val Ala Val Glu Pro Val Val
 15              20                  25                      30

TTC TCC CAA ATG GAG ACC AAG CTC ATC ACG TGG GGG GCA GAT ACC GCC            144
Phe Ser Gln Met Glu Thr Lys Leu Ile Thr Trp Gly Ala Asp Thr Ala
                 35                  40                  45

GCG TGC GGT GAC ATC ATC AAC GGC TTG CCT GTT TCC GCC CGC AGG GGC            192
Ala Cys Gly Asp Ile Ile Asn Gly Leu Pro Val Ser Ala Arg Arg Gly
                 50                  55                  60

CGG GAG ATA CTG CTC GGG CCA GCC GAT GGA ATG GTC TCC AAG GGT TGG            240
Arg Glu Ile Leu Leu Gly Pro Ala Asp Gly Met Val Ser Lys Gly Trp
             65                  70                  75

AGG TTG CTG GCG CCC ATC ACG GCG TAC GCC CAG CAG ACA AGG GGC CTC            288
Arg Leu Leu Ala Pro Ile Thr Ala Tyr Ala Gln Gln Thr Arg Gly Leu
     80                  85                  90

CTA GGG TGC ATA ATC ACC AGC CTA ACT GGC CGG GAC AAA AAC CAA GTG            336
Leu Gly Cys Ile Ile Thr Ser Leu Thr Gly Arg Asp Lys Asn Gln Val
 95                 100                 105                 110

GAG GGT GAG GTC CAG ATT GTG TCA ACT GCT GCC CAA ACC TTC CTG GCA            384
Glu Gly Glu Val Gln Ile Val Ser Thr Ala Ala Gln Thr Phe Leu Ala
                115                 120                 125

ACG TGC ATC ATC AAT GGG GTG TGC TGG ACT GTC TAC CAC GGG GCC GGA            432
Thr Cys Ile Ile Asn Gly Val Cys Trp Thr Val Tyr His Gly Ala Gly
                130                 135                 140

ACG AGG ACC ATC GCG TCA CCC AAG GGT CCT GTC ATC CAG ATG TAT ACC            480
Thr Arg Thr Ile Ala Ser Pro Lys Gly Pro Val Ile Gln Met Tyr Thr
            145                 150                 155

AAT GTA GAC CAA GAC CTT GTG GGC TGG CCC GCT TCG CAA GGT ACC CGC            528
Asn Val Asp Gln Asp Leu Val Gly Trp Pro Ala Ser Gln Gly Thr Arg
 160                 165                 170

TCA TTG ACA CCC TGC ACT TGC GGC TCC TCG GAC CTT TAC CTG GTC ACG            576
Ser Leu Thr Pro Cys Thr Cys Gly Ser Ser Asp Leu Tyr Leu Val Thr
175                 180                 185                 190

AGG CAC GCC GAT GTC ATT CCC GTG CGC CGG CGG GGT GAT AGC AGG GGC            624
Arg His Ala Asp Val Ile Pro Val Arg Arg Arg Gly Asp Ser Arg Gly
                195                 200                 205
```

| | | | | | | | | | | | | | | | |
|---|---|---|---|---|---|---|---|---|---|---|---|---|---|---|---|
| AGC | CTG | CTG | TCG | CCC | CGG | CCC | ATT | TCC | TAC | TTG | AAA | GGC | TCC | TCG | GGG | 672 |
| Ser | Leu | Leu | Ser | Pro | Arg | Pro | Ile | Ser | Tyr | Leu | Lys | Gly | Ser | Ser | Gly |
| | | | 210 | | | | | 215 | | | | | 220 | | |
| GGT | CCG | CTG | TTG | TGC | CCC | GCG | GGG | CAC | GCC | GTG | GGC | ATA | TTT | AGG | GCC | 720 |
| Gly | Pro | Leu | Leu | Cys | Pro | Ala | Gly | His | Ala | Val | Gly | Ile | Phe | Arg | Ala |
| | | 225 | | | | | 230 | | | | | 235 | | | |
| GCG | GTG | TGC | ACC | CGT | GGA | GTG | GCT | AAG | GCG | GTG | GAC | TTT | ATC | CCT | GTG | 768 |
| Ala | Val | Cys | Thr | Arg | Gly | Val | Ala | Lys | Ala | Val | Asp | Phe | Ile | Pro | Val |
| | 240 | | | | | 245 | | | | | 250 | | | | |
| GAG | AAC | CTA | GAG | ACA | ACC | ATG | AGG | TCC | CCG | GTG | TTC | ACG | GAT | AAC | TCC | 816 |
| Glu | Asn | Leu | Glu | Thr | Thr | Met | Arg | Ser | Pro | Val | Phe | Thr | Asp | Asn | Ser |
| 255 | | | | | 260 | | | | | 265 | | | | | 270 |
| TCT | CCA | CCA | GTA | GTG | CCC | CAG | AGC | TTC | CAG | GTG | GCT | CAC | CTC | CAT | GCT | 864 |
| Ser | Pro | Pro | Val | Val | Pro | Gln | Ser | Phe | Gln | Val | Ala | His | Leu | His | Ala |
| | | | 275 | | | | | 280 | | | | | 285 | | |
| CCC | ACA | GGC | AGC | GGC | AAA | AGC | ACC | AAG | GTC | CCG | GCT | GCA | TAT | GCA | GCT | 912 |
| Pro | Thr | Gly | Ser | Gly | Lys | Ser | Thr | Lys | Val | Pro | Ala | Ala | Tyr | Ala | Ala |
| | | | 290 | | | | | 295 | | | | | 300 | | |
| CAG | GGC | TAT | AAG | GTG | CTA | GTA | CTC | AAC | CCC | TCT | GTT | GCT | GCA | ACA | CTG | 960 |
| Gln | Gly | Tyr | Lys | Val | Leu | Val | Leu | Asn | Pro | Ser | Val | Ala | Ala | Thr | Leu |
| | | 305 | | | | | 310 | | | | | 315 | | | |
| GGC | TTT | GGT | GCT | TAC | ATG | TCC | AAG | GCT | CAT | GGG | ATC | GAT | CCT | AAC | ATC | 1008 |
| Gly | Phe | Gly | Ala | Tyr | Met | Ser | Lys | Ala | His | Gly | Ile | Asp | Pro | Asn | Ile |
| | 320 | | | | | 325 | | | | | 330 | | | | |
| AGG | ACC | GGG | GTG | AGA | ACA | ATT | ACC | ACT | GGC | AGC | CCC | ATC | ACG | TAC | TCC | 1056 |
| Arg | Thr | Gly | Val | Arg | Thr | Ile | Thr | Thr | Gly | Ser | Pro | Ile | Thr | Tyr | Ser |
| 335 | | | | | 340 | | | | | 345 | | | | | 350 |
| ACC | TAC | GGC | AAG | TTC | CTT | GCC | GAC | GGG | GGT | TGC | TCG | GGG | GGC | GCT | TAT | 1104 |
| Thr | Tyr | Gly | Lys | Phe | Leu | Ala | Asp | Gly | Gly | Cys | Ser | Gly | Gly | Ala | Tyr |
| | | | 355 | | | | | 360 | | | | | 365 | | |
| GAC | ATA | ATA | ATT | TGT | GAC | GAG | TGC | CAC | TCC | ACG | GAT | GCC | ACA | TCC | ATC | 1152 |
| Asp | Ile | Ile | Ile | Cys | Asp | Glu | Cys | His | Ser | Thr | Asp | Ala | Thr | Ser | Ile |
| | | | 370 | | | | | 375 | | | | | 380 | | |
| TTG | GGC | ATT | GGC | ACT | GTC | CTT | GAC | CAA | GCA | GAG | ACT | GCG | GGG | GCG | AGA | 1200 |
| Leu | Gly | Ile | Gly | Thr | Val | Leu | Asp | Gln | Ala | Glu | Thr | Ala | Gly | Ala | Arg |
| | | 385 | | | | | 390 | | | | | 395 | | | |
| CTG | GTT | GTG | CTC | GCC | ACC | GCC | ACC | CCT | CCG | GGC | TCC | GTC | ACT | GTG | CCC | 1248 |
| Leu | Val | Val | Leu | Ala | Thr | Ala | Thr | Pro | Pro | Gly | Ser | Val | Thr | Val | Pro |
| | 400 | | | | | 405 | | | | | 410 | | | | |
| CAT | CCC | AAC | ATC | GAG | GAG | GTT | GCT | CTG | TCC | ACC | ACC | GGA | GAG | ATC | CCT | 1296 |
| His | Pro | Asn | Ile | Glu | Glu | Val | Ala | Leu | Ser | Thr | Thr | Gly | Glu | Ile | Pro |
| 415 | | | | | 420 | | | | | 425 | | | | | 430 |
| TTT | TAC | GGC | AAG | GCT | ATC | CCC | CTC | GAA | GTA | ATC | AAG | GGG | GGG | AGA | CAT | 1344 |
| Phe | Tyr | Gly | Lys | Ala | Ile | Pro | Leu | Glu | Val | Ile | Lys | Gly | Gly | Arg | His |
| | | | 435 | | | | | 440 | | | | | 445 | | |
| CTC | ATC | TTC | TGT | CAT | TCA | AAG | AAG | AAG | TGC | GAC | GAA | CTC | GCC | GCA | AAG | 1392 |
| Leu | Ile | Phe | Cys | His | Ser | Lys | Lys | Lys | Cys | Asp | Glu | Leu | Ala | Ala | Lys |
| | | | 450 | | | | | 455 | | | | | 460 | | |
| CTG | GTC | GCA | TTG | GGC | ATC | AAT | GCC | GTG | GCC | TAC | TAC | CGC | GGT | CTT | GAC | 1440 |
| Leu | Val | Ala | Leu | Gly | Ile | Asn | Ala | Val | Ala | Tyr | Tyr | Arg | Gly | Leu | Asp |
| | | 465 | | | | | 470 | | | | | 475 | | | |
| GTG | TCC | GTC | ATC | CCG | ACC | AGC | GGC | GAT | GTT | GTC | GTC | GTG | GCA | ACC | GAT | 1488 |
| Val | Ser | Val | Ile | Pro | Thr | Ser | Gly | Asp | Val | Val | Val | Val | Ala | Thr | Asp |
| | 480 | | | | | 485 | | | | | 490 | | | | |
| GCC | CTC | ATG | ACC | GGC | TAT | ACC | GGC | GAC | TTC | GAC | TCG | GTG | ATA | GAC | TGC | 1536 |
| Ala | Leu | Met | Thr | Gly | Tyr | Thr | Gly | Asp | Phe | Asp | Ser | Val | Ile | Asp | Cys |
| 495 | | | | | 500 | | | | | 505 | | | | | 510 |
| AAT | ACG | TGT | GTC | ACC | CAG | ACA | GTC | GAT | TTC | AGC | CTT | GAC | CCT | ACC | TTC | 1584 |
| Asn | Thr | Cys | Val | Thr | Gln | Thr | Val | Asp | Phe | Ser | Leu | Asp | Pro | Thr | Phe |
| | | | 515 | | | | | 520 | | | | | 525 | | |

| | | | | | | | | | | | | | | | | |
|---|---|---|---|---|---|---|---|---|---|---|---|---|---|---|---|---|
| ACC | ATT | GAG | ACA | ATC | ACG | CTC | CCC | CAA | GAT | GCT | GTC | TCC | CGC | ACT | CAA | 1632 |
| Thr | Ile | Glu | Thr | Ile | Thr | Leu | Pro | Gln | Asp | Ala | Val | Ser | Arg | Thr | Gln | |
| | | 530 | | | | | 535 | | | | | | 540 | | | |
| CGT | CGG | GGC | AGG | ACT | GGC | AGG | GGG | AAG | CCA | GGC | ATC | TAC | AGA | TTT | GTG | 1680 |
| Arg | Arg | Gly | Arg | Thr | Gly | Arg | Gly | Lys | Pro | Gly | Ile | Tyr | Arg | Phe | Val | |
| | | 545 | | | | | 550 | | | | | | 555 | | | |
| GCA | CCG | GGG | GAG | CGC | CCT | CCC | GGC | ATG | TTC | GAC | TCG | TCC | GTC | CTC | TGT | 1728 |
| Ala | Pro | Gly | Glu | Arg | Pro | Pro | Gly | Met | Phe | Asp | Ser | Ser | Val | Leu | Cys | |
| | | 560 | | | | | 565 | | | | | | 570 | | | |
| GAG | TGC | TAT | GAC | GCA | GGC | TGT | GCT | TGG | TAT | GAG | CTC | ACG | CCC | GCC | GAG | 1776 |
| Glu | Cys | Tyr | Asp | Ala | Gly | Cys | Ala | Trp | Tyr | Glu | Leu | Thr | Pro | Ala | Glu | |
| 575 | | | | 580 | | | | | 585 | | | | | | 590 | |
| ACT | ACA | GTT | AGG | CTA | CGA | GCG | TAC | ATG | AAC | ACC | CCG | GGG | CTT | CCC | GTG | 1824 |
| Thr | Thr | Val | Arg | Leu | Arg | Ala | Tyr | Met | Asn | Thr | Pro | Gly | Leu | Pro | Val | |
| | | | | 595 | | | | | 600 | | | | | 605 | | |
| TGC | CAG | GAC | CAT | CTT | GAA | TTT | TGG | GAG | GGC | GTC | TTT | ACA | GGC | CTC | ACT | 1872 |
| Cys | Gln | Asp | His | Leu | Glu | Phe | Trp | Glu | Gly | Val | Phe | Thr | Gly | Leu | Thr | |
| | | | 610 | | | | | 615 | | | | | 620 | | | |
| CAT | ATA | GAT | GCC | CAC | TTT | CTA | TCC | CAG | ACA | AAG | CAG | AGT | GGG | GAG | AAC | 1920 |
| His | Ile | Asp | Ala | His | Phe | Leu | Ser | Gln | Thr | Lys | Gln | Ser | Gly | Glu | Asn | |
| | | 625 | | | | | 630 | | | | | 635 | | | | |
| CTT | CCT | TAC | CTG | GTA | GCG | TAC | CAA | GCC | ACC | GTG | TGC | GCT | AGG | GCT | CAA | 1968 |
| Leu | Pro | Tyr | Leu | Val | Ala | Tyr | Gln | Ala | Thr | Val | Cys | Ala | Arg | Ala | Gln | |
| | | 640 | | | | | 645 | | | | | 650 | | | | |
| GCC | CCT | CCC | CCA | TCG | TGG | GAC | CAG | ATG | TGG | AAG | TGT | TTG | ATT | CGC | CTC | 2016 |
| Ala | Pro | Pro | Pro | Ser | Trp | Asp | Gln | Met | Trp | Lys | Cys | Leu | Ile | Arg | Leu | |
| 655 | | | | | 660 | | | | | 665 | | | | | 670 | |
| AAG | CCC | ACC | CTC | CAT | GGG | CCA | ACA | CCC | CTG | CTA | TAC | AGA | CTG | GGC | GCT | 2064 |
| Lys | Pro | Thr | Leu | His | Gly | Pro | Thr | Pro | Leu | Leu | Tyr | Arg | Leu | Gly | Ala | |
| | | | | 675 | | | | 680 | | | | | 685 | | | |

( 2 ) INFORMATION FOR SEQ ID NO:70:

( i ) SEQUENCE CHARACTERISTICS:
        ( A ) LENGTH: 686 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

| | | | | | | | | | | | | | | |
|---|---|---|---|---|---|---|---|---|---|---|---|---|---|---|
| Gly | Thr | Tyr | Val | Tyr | Asn | His | Leu | Thr | Pro | Leu | Arg | Asp | Trp | Ala | His |
| 1 | | | | 5 | | | | | 10 | | | | | 15 | |
| Asn | Gly | Leu | Arg | Asp | Leu | Ala | Val | Ala | Val | Glu | Pro | Val | Val | Phe | Ser |
| | | | 20 | | | | | 25 | | | | | 30 | | |
| Gln | Met | Glu | Thr | Lys | Leu | Ile | Thr | Trp | Gly | Ala | Asp | Thr | Ala | Ala | Cys |
| | | | 35 | | | | | 40 | | | | | 45 | | |
| Gly | Asp | Ile | Ile | Asn | Gly | Leu | Pro | Val | Ser | Ala | Arg | Arg | Gly | Arg | Glu |
| | | 50 | | | | | 55 | | | | | 60 | | | |
| Ile | Leu | Leu | Gly | Pro | Ala | Asp | Gly | Met | Val | Ser | Lys | Gly | Trp | Arg | Leu |
| 65 | | | | | 70 | | | | | 75 | | | | | 80 |
| Leu | Ala | Pro | Ile | Thr | Ala | Tyr | Ala | Gln | Gln | Thr | Arg | Gly | Leu | Leu | Gly |
| | | | | 85 | | | | | 90 | | | | | 95 | |
| Cys | Ile | Ile | Thr | Ser | Leu | Thr | Gly | Arg | Asp | Lys | Asn | Gln | Val | Glu | Gly |
| | | | 100 | | | | | 105 | | | | | 110 | | |
| Glu | Val | Gln | Ile | Val | Ser | Thr | Ala | Ala | Gln | Thr | Phe | Leu | Ala | Thr | Cys |
| | | 115 | | | | | 120 | | | | | 125 | | | |
| Ile | Ile | Asn | Gly | Val | Cys | Trp | Thr | Val | Tyr | His | Gly | Ala | Gly | Thr | Arg |
| | | 130 | | | | | 135 | | | | | 140 | | | |

| Thr | Ile | Ala | Ser | Pro | Lys | Gly | Pro | Val | Ile | Gln | Met | Tyr | Thr | Asn | Val |
| --- | --- | --- | --- | --- | --- | --- | --- | --- | --- | --- | --- | --- | --- | --- | --- |
| 145 | | | | 150 | | | | | 155 | | | | | | 160 |

| Asp | Gln | Asp | Leu | Val | Gly | Trp | Pro | Ala | Ser | Gln | Gly | Thr | Arg | Ser | Leu |
| --- | --- | --- | --- | --- | --- | --- | --- | --- | --- | --- | --- | --- | --- | --- | --- |
| | | | | 165 | | | | | 170 | | | | | 175 | |

| Thr | Pro | Cys | Thr | Cys | Gly | Ser | Ser | Asp | Leu | Tyr | Leu | Val | Thr | Arg | His |
| --- | --- | --- | --- | --- | --- | --- | --- | --- | --- | --- | --- | --- | --- | --- | --- |
| | | | 180 | | | | | 185 | | | | | 190 | | |

| Ala | Asp | Val | Ile | Pro | Val | Arg | Arg | Arg | Gly | Asp | Ser | Arg | Gly | Ser | Leu |
| --- | --- | --- | --- | --- | --- | --- | --- | --- | --- | --- | --- | --- | --- | --- | --- |
| | | 195 | | | | | 200 | | | | | 205 | | | |

| Leu | Ser | Pro | Arg | Pro | Ile | Ser | Tyr | Leu | Lys | Gly | Ser | Ser | Gly | Gly | Pro |
| --- | --- | --- | --- | --- | --- | --- | --- | --- | --- | --- | --- | --- | --- | --- | --- |
| | 210 | | | | | 215 | | | | 220 | | | | | |

| Leu | Leu | Cys | Pro | Ala | Gly | His | Ala | Val | Gly | Ile | Phe | Arg | Ala | Ala | Val |
| --- | --- | --- | --- | --- | --- | --- | --- | --- | --- | --- | --- | --- | --- | --- | --- |
| 225 | | | | | 230 | | | | | 235 | | | | | 240 |

| Cys | Thr | Arg | Gly | Val | Ala | Lys | Ala | Val | Asp | Phe | Ile | Pro | Val | Glu | Asn |
| --- | --- | --- | --- | --- | --- | --- | --- | --- | --- | --- | --- | --- | --- | --- | --- |
| | | | | 245 | | | | | 250 | | | | | 255 | |

| Leu | Glu | Thr | Thr | Met | Arg | Ser | Pro | Val | Phe | Thr | Asp | Asn | Ser | Ser | Pro |
| --- | --- | --- | --- | --- | --- | --- | --- | --- | --- | --- | --- | --- | --- | --- | --- |
| | | | 260 | | | | | 265 | | | | | 270 | | |

| Pro | Val | Val | Pro | Gln | Ser | Phe | Gln | Val | Ala | His | Leu | His | Ala | Pro | Thr |
| --- | --- | --- | --- | --- | --- | --- | --- | --- | --- | --- | --- | --- | --- | --- | --- |
| | | 275 | | | | | 280 | | | | | 285 | | | |

| Gly | Ser | Gly | Lys | Ser | Thr | Lys | Val | Pro | Ala | Ala | Tyr | Ala | Ala | Gln | Gly |
| --- | --- | --- | --- | --- | --- | --- | --- | --- | --- | --- | --- | --- | --- | --- | --- |
| | 290 | | | | | 295 | | | | | 300 | | | | |

| Tyr | Lys | Val | Leu | Val | Leu | Asn | Pro | Ser | Val | Ala | Ala | Thr | Leu | Gly | Phe |
| --- | --- | --- | --- | --- | --- | --- | --- | --- | --- | --- | --- | --- | --- | --- | --- |
| 305 | | | | | 310 | | | | | 315 | | | | | 320 |

| Gly | Ala | Tyr | Met | Ser | Lys | Ala | His | Gly | Ile | Asp | Pro | Asn | Ile | Arg | Thr |
| --- | --- | --- | --- | --- | --- | --- | --- | --- | --- | --- | --- | --- | --- | --- | --- |
| | | | | 325 | | | | | 330 | | | | | 335 | |

| Gly | Val | Arg | Thr | Ile | Thr | Thr | Gly | Ser | Pro | Ile | Thr | Tyr | Ser | Thr | Tyr |
| --- | --- | --- | --- | --- | --- | --- | --- | --- | --- | --- | --- | --- | --- | --- | --- |
| | | | 340 | | | | | 345 | | | | | 350 | | |

| Gly | Lys | Phe | Leu | Ala | Asp | Gly | Gly | Cys | Ser | Gly | Gly | Ala | Tyr | Asp | Ile |
| --- | --- | --- | --- | --- | --- | --- | --- | --- | --- | --- | --- | --- | --- | --- | --- |
| | | 355 | | | | | 360 | | | | | 365 | | | |

| Ile | Ile | Cys | Asp | Glu | Cys | His | Ser | Thr | Asp | Ala | Thr | Ser | Ile | Leu | Gly |
| --- | --- | --- | --- | --- | --- | --- | --- | --- | --- | --- | --- | --- | --- | --- | --- |
| | 370 | | | | | 375 | | | | 380 | | | | | |

| Ile | Gly | Thr | Val | Leu | Asp | Gln | Ala | Glu | Thr | Ala | Gly | Ala | Arg | Leu | Val |
| --- | --- | --- | --- | --- | --- | --- | --- | --- | --- | --- | --- | --- | --- | --- | --- |
| 385 | | | | | 390 | | | | | 395 | | | | | 400 |

| Val | Leu | Ala | Thr | Ala | Thr | Pro | Pro | Gly | Ser | Val | Thr | Val | Pro | His | Pro |
| --- | --- | --- | --- | --- | --- | --- | --- | --- | --- | --- | --- | --- | --- | --- | --- |
| | | | | 405 | | | | | 410 | | | | | 415 | |

| Asn | Ile | Glu | Glu | Val | Ala | Leu | Ser | Thr | Thr | Gly | Glu | Ile | Pro | Phe | Tyr |
| --- | --- | --- | --- | --- | --- | --- | --- | --- | --- | --- | --- | --- | --- | --- | --- |
| | | | 420 | | | | | 425 | | | | | 430 | | |

| Gly | Lys | Ala | Ile | Pro | Leu | Glu | Val | Ile | Lys | Gly | Gly | Arg | His | Leu | Ile |
| --- | --- | --- | --- | --- | --- | --- | --- | --- | --- | --- | --- | --- | --- | --- | --- |
| | | | 435 | | | | | 440 | | | | | 445 | | |

| Phe | Cys | His | Ser | Lys | Lys | Lys | Cys | Asp | Glu | Leu | Ala | Ala | Lys | Leu | Val |
| --- | --- | --- | --- | --- | --- | --- | --- | --- | --- | --- | --- | --- | --- | --- | --- |
| | 450 | | | | 455 | | | | | 460 | | | | | |

| Ala | Leu | Gly | Ile | Asn | Ala | Val | Ala | Tyr | Tyr | Arg | Gly | Leu | Asp | Val | Ser |
| --- | --- | --- | --- | --- | --- | --- | --- | --- | --- | --- | --- | --- | --- | --- | --- |
| 465 | | | | | 470 | | | | | 475 | | | | | 480 |

| Val | Ile | Pro | Thr | Ser | Gly | Asp | Val | Val | Val | Val | Ala | Thr | Asp | Ala | Leu |
| --- | --- | --- | --- | --- | --- | --- | --- | --- | --- | --- | --- | --- | --- | --- | --- |
| | | | | 485 | | | | | 490 | | | | | 495 | |

| Met | Thr | Gly | Tyr | Thr | Gly | Asp | Phe | Asp | Ser | Val | Ile | Asp | Cys | Asn | Thr |
| --- | --- | --- | --- | --- | --- | --- | --- | --- | --- | --- | --- | --- | --- | --- | --- |
| | | | 500 | | | | | 505 | | | | | 510 | | |

| Cys | Val | Thr | Gln | Thr | Val | Asp | Phe | Ser | Leu | Asp | Pro | Thr | Phe | Thr | Ile |
| --- | --- | --- | --- | --- | --- | --- | --- | --- | --- | --- | --- | --- | --- | --- | --- |
| | | 515 | | | | | 520 | | | | | 525 | | | |

| Glu | Thr | Ile | Thr | Leu | Pro | Gln | Asp | Ala | Val | Ser | Arg | Thr | Gln | Arg | Arg |
| --- | --- | --- | --- | --- | --- | --- | --- | --- | --- | --- | --- | --- | --- | --- | --- |
| | 530 | | | | | 535 | | | | | 540 | | | | |

| Gly | Arg | Thr | Gly | Arg | Gly | Lys | Pro | Gly | Ile | Tyr | Arg | Phe | Val | Ala | Pro |
| --- | --- | --- | --- | --- | --- | --- | --- | --- | --- | --- | --- | --- | --- | --- | --- |
| 545 | | | | | 550 | | | | | 555 | | | | | 560 |

| Gly | Glu | Arg | Pro | Pro | Gly | Met | Phe | Asp | Ser | Ser | Val | Leu | Cys | Glu | Cys |
| --- | --- | --- | --- | --- | --- | --- | --- | --- | --- | --- | --- | --- | --- | --- | --- |
| | | | | 565 | | | | | 570 | | | | | 575 | |

| Tyr | Asp | Ala | Gly | Cys | Ala | Trp | Tyr | Glu | Leu | Thr | Pro | Ala | Glu | Thr | Thr |
|---|---|---|---|---|---|---|---|---|---|---|---|---|---|---|---|
| | | | 580 | | | | 585 | | | | | | 590 | | |

| Val | Arg | Leu | Arg | Ala | Tyr | Met | Asn | Thr | Pro | Gly | Leu | Pro | Val | Cys | Gln |
|---|---|---|---|---|---|---|---|---|---|---|---|---|---|---|---|
| | | 595 | | | | | 600 | | | | | 605 | | | |

| Asp | His | Leu | Glu | Phe | Trp | Glu | Gly | Val | Phe | Thr | Gly | Leu | Thr | His | Ile |
|---|---|---|---|---|---|---|---|---|---|---|---|---|---|---|---|
| | 610 | | | | | 615 | | | | | 620 | | | | |

| Asp | Ala | His | Phe | Leu | Ser | Gln | Thr | Lys | Gln | Ser | Gly | Glu | Asn | Leu | Pro |
|---|---|---|---|---|---|---|---|---|---|---|---|---|---|---|---|
| 625 | | | | | 630 | | | | | 635 | | | | | 640 |

| Tyr | Leu | Val | Ala | Tyr | Gln | Ala | Thr | Val | Cys | Ala | Arg | Ala | Gln | Ala | Pro |
|---|---|---|---|---|---|---|---|---|---|---|---|---|---|---|---|
| | | | | 645 | | | | | 650 | | | | | 655 | |

| Pro | Pro | Ser | Trp | Asp | Gln | Met | Trp | Lys | Cys | Leu | Ile | Arg | Leu | Lys | Pro |
|---|---|---|---|---|---|---|---|---|---|---|---|---|---|---|---|
| | | | 660 | | | | | 665 | | | | | 670 | | |

| Thr | Leu | His | Gly | Pro | Thr | Pro | Leu | Leu | Tyr | Arg | Leu | Gly | Ala |
|---|---|---|---|---|---|---|---|---|---|---|---|---|---|
| | | 675 | | | | | 680 | | | | | 685 | |

( 2 ) INFORMATION FOR SEQ ID NO:71:

( i ) SEQUENCE CHARACTERISTICS:
        ( A ) LENGTH: 368 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..366

( x i ) SEQUENCE DESCRIPTION: SEQ ID NO:71:

| AAT | TCG | GAA | AAC | CAA | GTG | GAG | GGT | GAG | GTC | CAG | ATT | GTG | TCA | ACT | GCT | 48 |
|---|---|---|---|---|---|---|---|---|---|---|---|---|---|---|---|---|
| Asn | Ser | Glu | Asn | Gln | Val | Glu | Gly | Glu | Val | Gln | Ile | Val | Ser | Thr | Ala | |
| 1 | | | | 5 | | | | | 10 | | | | | 15 | | |

| GCC | CAA | ACC | TTC | CTG | GCA | ACG | TGC | ATC | AAT | GGG | GTG | TGC | TGG | ACT | GTC | 96 |
|---|---|---|---|---|---|---|---|---|---|---|---|---|---|---|---|---|
| Ala | Gln | Thr | Phe | Leu | Ala | Thr | Cys | Ile | Asn | Gly | Val | Cys | Trp | Thr | Val | |
| | | | 20 | | | | | 25 | | | | | 30 | | | |

| TAC | CAC | GGG | GCC | GGA | ACG | AGG | ACC | ATC | GCG | TCA | CCC | AAG | GGT | CCT | GTC | 144 |
|---|---|---|---|---|---|---|---|---|---|---|---|---|---|---|---|---|
| Tyr | His | Gly | Ala | Gly | Thr | Arg | Thr | Ile | Ala | Ser | Pro | Lys | Gly | Pro | Val | |
| | | 35 | | | | | 40 | | | | | 45 | | | | |

| ATC | CAG | ATG | TAT | ACC | AAT | GTA | GAC | CAA | GAC | CTT | GTG | GGC | TGG | CCC | GCT | 192 |
|---|---|---|---|---|---|---|---|---|---|---|---|---|---|---|---|---|
| Ile | Gln | Met | Tyr | Thr | Asn | Val | Asp | Gln | Asp | Leu | Val | Gly | Trp | Pro | Ala | |
| | 50 | | | | | 55 | | | | | 60 | | | | | |

| TCG | CAA | GGT | ACC | CGC | TCA | TTG | ACA | CCC | TGC | ACT | TGC | GGC | TCC | TCG | GAC | 240 |
|---|---|---|---|---|---|---|---|---|---|---|---|---|---|---|---|---|
| Ser | Gln | Gly | Thr | Arg | Ser | Leu | Thr | Pro | Cys | Thr | Cys | Gly | Ser | Ser | Asp | |
| 65 | | | | | 70 | | | | | 75 | | | | | 80 | |

| CTT | TAC | CTG | GTC | ACG | AGG | CAC | GCC | GAT | GTC | ATT | CCC | GTG | CGC | CGG | CGG | 288 |
|---|---|---|---|---|---|---|---|---|---|---|---|---|---|---|---|---|
| Leu | Tyr | Leu | Val | Thr | Arg | His | Ala | Asp | Val | Ile | Pro | Val | Arg | Arg | Arg | |
| | | | | 85 | | | | | 90 | | | | | 95 | | |

| GGT | GAT | AGC | AGG | GGC | AGC | CTC | GTG | TCG | CCC | CGG | CCC | ATT | TCC | TAC | TTG | 336 |
|---|---|---|---|---|---|---|---|---|---|---|---|---|---|---|---|---|
| Gly | Asp | Ser | Arg | Gly | Ser | Leu | Val | Ser | Pro | Arg | Pro | Ile | Ser | Tyr | Leu | |
| | | | 100 | | | | | 105 | | | | | 110 | | | |

| AAA | GGC | TCC | TCG | GGG | GGT | CCG | CTG | CCG | AAT | TC | | | | | | 368 |
|---|---|---|---|---|---|---|---|---|---|---|---|---|---|---|---|---|
| Lys | Gly | Ser | Ser | Gly | Gly | Pro | Leu | Pro | Asn | | | | | | | |
| | | 115 | | | | | 120 | | | | | | | | | |

( 2 ) INFORMATION FOR SEQ ID NO:72:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

```
Asn  Ser  Glu  Asn  Gln  Val  Glu  Gly  Glu  Val  Gln  Ile  Val  Ser  Thr  Ala
 1              5                   10                       15

Ala  Gln  Thr  Phe  Leu  Ala  Thr  Cys  Ile  Asn  Gly  Val  Cys  Trp  Thr  Val
               20                   25                       30

Tyr  His  Gly  Ala  Gly  Thr  Arg  Thr  Ile  Ala  Ser  Pro  Lys  Gly  Pro  Val
               35                   40                       45

Ile  Gln  Met  Tyr  Thr  Asn  Val  Asp  Gln  Asp  Leu  Val  Gly  Trp  Pro  Ala
          50                   55                   60

Ser  Gln  Gly  Thr  Arg  Ser  Leu  Thr  Pro  Cys  Thr  Cys  Gly  Ser  Ser  Asp
 65                   70                   75                             80

Leu  Tyr  Leu  Val  Thr  Arg  His  Ala  Asp  Val  Ile  Pro  Val  Arg  Arg  Arg
               85                   90                       95

Gly  Asp  Ser  Arg  Gly  Ser  Leu  Val  Ser  Pro  Arg  Pro  Ile  Ser  Tyr  Leu
               100                  105                      110

Lys  Gly  Ser  Ser  Gly  Gly  Pro  Leu  Pro  Asn
               115                  120
```

( 2 ) INFORMATION FOR SEQ ID NO:73:

( i ) SEQUENCE CHARACTERISTICS:
        ( A ) LENGTH: 208 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..207

( x i ) SEQUENCE DESCRIPTION: SEQ ID NO:73:

```
GAA  TTC  GGG  GGC  CTG  CTG  TTG  TGC  CCC  GCG  GCA  GCC  GTG  GGC  ATA  TTT    48
Glu  Phe  Gly  Gly  Leu  Leu  Leu  Cys  Pro  Ala  Ala  Ala  Val  Gly  Ile  Phe
 1              5                   10                       15

AGG  GCC  GCG  GTG  TGC  ACC  CGT  GGA  GTG  GCT  AAG  GCG  GTG  GAC  TTT  ATC    96
Arg  Ala  Ala  Val  Cys  Thr  Arg  Gly  Val  Ala  Lys  Ala  Val  Asp  Phe  Ile
               20                   25                       30

CCT  GTG  GAG  AAC  CTA  GAG  ACA  ACC  ATG  AGG  TCC  CCG  GTG  TTC  ACG  GAT   144
Pro  Val  Glu  Asn  Leu  Glu  Thr  Thr  Met  Arg  Ser  Pro  Val  Phe  Thr  Asp
               35                   40                       45

AAC  TCC  TCT  CCA  CCA  GTA  GTG  CCC  CAG  AGC  TTC  CAG  GTG  GCT  CAC  CTC   192
Asn  Ser  Ser  Pro  Pro  Val  Val  Pro  Gln  Ser  Phe  Gln  Val  Ala  His  Leu
 50                   55                   60

CAT  GCT  CCC  CGA  ATT  C                                                        208
His  Ala  Pro  Arg  Ile
 65
```

( 2 ) INFORMATION FOR SEQ ID NO:74:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( x i ) SEQUENCE DESCRIPTION: SEQ ID NO:74:

```
Glu  Phe  Gly  Gly  Leu  Leu  Leu  Cys  Pro  Ala  Ala  Ala  Val  Gly  Ile  Phe
 1              5                   10                       15

Arg  Ala  Ala  Val  Cys  Thr  Arg  Gly  Val  Ala  Lys  Ala  Val  Asp  Phe  Ile
               20                   25                       30

Pro  Val  Glu  Asn  Leu  Glu  Thr  Thr  Met  Arg  Ser  Pro  Val  Phe  Thr  Asp
               35                   40                       45
```

(2) INFORMATION FOR SEQ ID NO:75:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..279

(xi) SEQUENCE DESCRIPTION: SEQ ID NO:75:

```
CCC TGC ACT TGC GGC TCC TCG GAC CTT TAC CTG GTC ACG AGG CAC GCC    48
Pro Cys Thr Cys Gly Ser Ser Asp Leu Tyr Leu Val Thr Arg His Ala
 1               5                  10                  15

GAT GTC ATT CCC GTG CGC CGG CGG GGT GAT AGC AGG GGC AGC CTG CTG    96
Asp Val Ile Pro Val Arg Arg Arg Gly Asp Ser Arg Gly Ser Leu Leu
             20                  25                  30

TCG CCC CGG CCC ATT TCC TAC TTG AAA GGC TCC TCG GGG GGT CCG CTG   144
Ser Pro Arg Pro Ile Ser Tyr Leu Lys Gly Ser Ser Gly Gly Pro Leu
         35                  40                  45

TTG TGC CCC GCG GGG CAC GCC GTG GGC ATA TTT AGG GCC GCG GTG TGC   192
Leu Cys Pro Ala Gly His Ala Val Gly Ile Phe Arg Ala Ala Val Cys
     50                  55                  60

ACC CGT GGA GTG GCT AAG GCG GTG GAC TTT ATC CCT GTG GAG AAC CTA   240
Thr Arg Gly Val Ala Lys Ala Val Asp Phe Ile Pro Val Glu Asn Leu
 65                  70                  75                  80

GAG ACA ACC ATG AGG TCC CCG GTG TTC ACG GAT AAC TCC TC            281
Glu Thr Thr Met Arg Ser Pro Val Phe Thr Asp Asn Ser
                 85                  90
```

(2) INFORMATION FOR SEQ ID NO:76:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:76:

```
Pro Cys Thr Cys Gly Ser Ser Asp Leu Tyr Leu Val Thr Arg His Ala
 1               5                  10                  15

Asp Val Ile Pro Val Arg Arg Arg Gly Asp Ser Arg Gly Ser Leu Leu
             20                  25                  30

Ser Pro Arg Pro Ile Ser Tyr Leu Lys Gly Ser Ser Gly Gly Pro Leu
         35                  40                  45

Leu Cys Pro Ala Gly His Ala Val Gly Ile Phe Arg Ala Ala Val Cys
     50                  55                  60

Thr Arg Gly Val Ala Lys Ala Val Asp Phe Ile Pro Val Glu Asn Leu
 65                  70                  75                  80

Glu Thr Thr Met Arg Ser Pro Val Phe Thr Asp Asn Ser
                 85                  90
```

(2) INFORMATION FOR SEQ ID NO:77:

(i) SEQUENCE CHARACTERISTICS:

(A) LENGTH: 416 base pairs
(B) TYPE: nucleic acid
(C) STRANDEDNESS: single
(D) TOPOLOGY: linear (ix) FEATURE:
(A) NAME/KEY: CDS
(B) LOCATION: 1..414

(xi) SEQUENCE DESCRIPTION: SEQ ID NO:77:

| ATT | CGG | GGC | ACC | TAT | GTT | TAT | AAC | CAT | CTC | ACT | CCT | CTT | CGG | GAC | TGG | 48 |
| Ile | Arg | Gly | Thr | Tyr | Val | Tyr | Asn | His | Leu | Thr | Pro | Leu | Arg | Asp | Trp | |
| 1 | | | | 5 | | | | | 10 | | | | | 15 | | |

| GCG | CAC | AAC | GGC | TTG | CGA | GAT | CTG | GCC | GTG | GCT | GTA | GAG | CCA | GTC | GTC | 96 |
| Ala | His | Asn | Gly | Leu | Arg | Asp | Leu | Ala | Val | Ala | Val | Glu | Pro | Val | Val | |
| | | | 20 | | | | | 25 | | | | | 30 | | | |

| TTC | TCC | CAA | ATG | GAG | ACC | AAG | CTC | ATC | ACG | TGG | GGG | GCA | GAT | ACC | GCC | 144 |
| Phe | Ser | Gln | Met | Glu | Thr | Lys | Leu | Ile | Thr | Trp | Gly | Ala | Asp | Thr | Ala | |
| | | 35 | | | | | 40 | | | | | 45 | | | | |

| GCG | TGC | GGT | GAC | ATC | ATC | AAC | GGC | TTG | CCT | GTT | TCC | GCC | CGC | AGG | GGC | 192 |
| Ala | Cys | Gly | Asp | Ile | Ile | Asn | Gly | Leu | Pro | Val | Ser | Ala | Arg | Arg | Gly | |
| | 50 | | | | | 55 | | | | | 60 | | | | | |

| CGG | GAG | ATA | CTG | CTC | GGG | CCA | GCC | GAT | GGA | ATG | GTC | TCC | AAG | GGT | TGG | 240 |
| Arg | Glu | Ile | Leu | Leu | Gly | Pro | Ala | Asp | Gly | Met | Val | Ser | Lys | Gly | Trp | |
| 65 | | | | | 70 | | | | | 75 | | | | | 80 | |

| AGG | TTG | CTG | GCG | CCC | ATC | ACG | GCG | TAC | GCC | CAG | CAG | ACA | AGG | GGC | CTC | 288 |
| Arg | Leu | Leu | Ala | Pro | Ile | Thr | Ala | Tyr | Ala | Gln | Gln | Thr | Arg | Gly | Leu | |
| | | | | 85 | | | | | 90 | | | | | 95 | | |

| CTA | GGG | TGC | ATA | ATC | ACC | AGC | CTA | ACT | GGC | CGG | GAC | AAA | AAC | CAA | GTG | 336 |
| Leu | Gly | Cys | Ile | Ile | Thr | Ser | Leu | Thr | Gly | Arg | Asp | Lys | Asn | Gln | Val | |
| | | | 100 | | | | | 105 | | | | | 110 | | | |

| GAG | GGT | GAG | GTC | CAG | ATT | GTG | TCA | ACT | GCT | GCC | CAA | ACC | TTC | CTG | GCA | 384 |
| Glu | Gly | Glu | Val | Gln | Ile | Val | Ser | Thr | Ala | Ala | Gln | Thr | Phe | Leu | Ala | |
| | | 115 | | | | | 120 | | | | | 125 | | | | |

| ACG | TGC | ATC | AAT | GGG | GTG | TGC | TGG | CCG | AAT | TC | | | | | | 416 |
| Thr | Cys | Ile | Asn | Gly | Val | Cys | Trp | Pro | Asn | | | | | | | |
| | 130 | | | | | 135 | | | | | | | | | | |

(2) INFORMATION FOR SEQ ID NO:78:

(i) SEQUENCE CHARACTERISTICS:
(A) LENGTH: 138 amino acids
(B) TYPE: amino acid
(D) TOPOLOGY: linear (ii) MOLECULE TYPE: protein (xi) SEQUENCE DESCRIPTION: SEQ ID NO:78:

| Ile | Arg | Gly | Thr | Tyr | Val | Tyr | Asn | His | Leu | Thr | Pro | Leu | Arg | Asp | Trp |
| 1 | | | | 5 | | | | | 10 | | | | | 15 | |

| Ala | His | Asn | Gly | Leu | Arg | Asp | Leu | Ala | Val | Ala | Val | Glu | Pro | Val | Val |
| | | | 20 | | | | | 25 | | | | | 30 | | |

| Phe | Ser | Gln | Met | Glu | Thr | Lys | Leu | Ile | Thr | Trp | Gly | Ala | Asp | Thr | Ala |
| | | 35 | | | | | 40 | | | | | 45 | | | |

| Ala | Cys | Gly | Asp | Ile | Ile | Asn | Gly | Leu | Pro | Val | Ser | Ala | Arg | Arg | Gly |
| | 50 | | | | | 55 | | | | | 60 | | | | |

| Arg | Glu | Ile | Leu | Leu | Gly | Pro | Ala | Asp | Gly | Met | Val | Ser | Lys | Gly | Trp |
| 65 | | | | | 70 | | | | | 75 | | | | | 80 |

| Arg | Leu | Leu | Ala | Pro | Ile | Thr | Ala | Tyr | Ala | Gln | Gln | Thr | Arg | Gly | Leu |
| | | | | 85 | | | | | 90 | | | | | 95 | |

| Leu | Gly | Cys | Ile | Ile | Thr | Ser | Leu | Thr | Gly | Arg | Asp | Lys | Asn | Gln | Val |
| | | | 100 | | | | | 105 | | | | | 110 | | |

| Glu | Gly | Glu | Val | Gln | Ile | Val | Ser | Thr | Ala | Ala | Gln | Thr | Phe | Leu | Ala |
|---|---|---|---|---|---|---|---|---|---|---|---|---|---|---|---|
| 115 | | | | 120 | | | | | | | 125 | | | | |

| Thr | Cys | Ile | Asn | Gly | Val | Cys | Trp | Pro | Asn |
|---|---|---|---|---|---|---|---|---|---|
| 130 | | | | | 135 | | | | |

( 2 ) INFORMATION FOR SEQ ID NO:79:

( i ) SEQUENCE CHARACTERISTICS:
        ( A ) LENGTH: 308 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..306

( x i ) SEQUENCE DESCRIPTION: SEQ ID NO:79:

| GAA | TTC | GGG | TCC | GTC | ATC | CCG | ACC | AGC | GGC | GAT | GTT | GTC | GTC | GTC | GCA | 48 |
|---|---|---|---|---|---|---|---|---|---|---|---|---|---|---|---|---|
| Glu | Phe | Gly | Ser | Val | Ile | Pro | Thr | Ser | Gly | Asp | Val | Val | Val | Val | Ala | |
| 1 | | | | 5 | | | | | 10 | | | | | 15 | | |

| ACC | GAT | GCC | CTC | ATG | ACC | GGC | TAT | ACC | GGC | GAC | TTC | GAC | TCG | GTG | ATA | 96 |
|---|---|---|---|---|---|---|---|---|---|---|---|---|---|---|---|---|
| Thr | Asp | Ala | Leu | Met | Thr | Gly | Tyr | Thr | Gly | Asp | Phe | Asp | Ser | Val | Ile | |
| | | | | 20 | | | | | 25 | | | | | 30 | | |

| GAC | TGC | AAT | ACG | TGT | GTC | ACC | CAG | ACA | GTC | GAT | TTC | AGC | CTT | GAC | CCT | 144 |
|---|---|---|---|---|---|---|---|---|---|---|---|---|---|---|---|---|
| Asp | Cys | Asn | Thr | Cys | Val | Thr | Gln | Thr | Val | Asp | Phe | Ser | Leu | Asp | Pro | |
| | | | 35 | | | | | 40 | | | | | 45 | | | |

| ACC | TTC | ACC | ATT | GAG | ACA | ATC | ACG | CTC | CCC | CAA | GAT | GCT | GTC | TCC | CGC | 192 |
|---|---|---|---|---|---|---|---|---|---|---|---|---|---|---|---|---|
| Thr | Phe | Thr | Ile | Glu | Thr | Ile | Thr | Leu | Pro | Gln | Asp | Ala | Val | Ser | Arg | |
| | | 50 | | | | | 55 | | | | | 60 | | | | |

| ACT | CAA | CGT | CGG | GGC | AGG | ACT | GGC | AGG | GGG | AAG | CCA | GGC | ATC | TAC | AGA | 240 |
|---|---|---|---|---|---|---|---|---|---|---|---|---|---|---|---|---|
| Thr | Gln | Arg | Arg | Gly | Arg | Thr | Gly | Arg | Gly | Lys | Pro | Gly | Ile | Tyr | Arg | |
| 65 | | | | | 70 | | | | | 75 | | | | | 80 | |

| TTT | GTG | GCA | CCG | GGG | GAG | CGC | CCC | TCC | GGC | ATG | TTC | GAC | TCG | TCC | GTC | 288 |
|---|---|---|---|---|---|---|---|---|---|---|---|---|---|---|---|---|
| Phe | Val | Ala | Pro | Gly | Glu | Arg | Pro | Ser | Gly | Met | Phe | Asp | Ser | Ser | Val | |
| | | | | 85 | | | | | 90 | | | | | 95 | | |

| CTC | TGT | GAG | TGC | CCG | AAT | TC | 308 |
|---|---|---|---|---|---|---|---|
| Leu | Cys | Glu | Cys | Pro | Asn | | |
| | | | 100 | | | | |

( 2 ) INFORMATION FOR SEQ ID NO:80:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:80:

| Glu | Phe | Gly | Ser | Val | Ile | Pro | Thr | Ser | Gly | Asp | Val | Val | Val | Val | Ala |
|---|---|---|---|---|---|---|---|---|---|---|---|---|---|---|---|
| 1 | | | | 5 | | | | | 10 | | | | | 15 | |

| Thr | Asp | Ala | Leu | Met | Thr | Gly | Tyr | Thr | Gly | Asp | Phe | Asp | Ser | Val | Ile |
|---|---|---|---|---|---|---|---|---|---|---|---|---|---|---|---|
| | | | | 20 | | | | | 25 | | | | | 30 | |

| Asp | Cys | Asn | Thr | Cys | Val | Thr | Gln | Thr | Val | Asp | Phe | Ser | Leu | Asp | Pro |
|---|---|---|---|---|---|---|---|---|---|---|---|---|---|---|---|
| | | | 35 | | | | | 40 | | | | | 45 | | |

| Thr | Phe | Thr | Ile | Glu | Thr | Ile | Thr | Leu | Pro | Gln | Asp | Ala | Val | Ser | Arg |
|---|---|---|---|---|---|---|---|---|---|---|---|---|---|---|---|
| | | 50 | | | | | 55 | | | | | 60 | | | |

| Thr | Gln | Arg | Arg | Gly | Arg | Thr | Gly | Arg | Gly | Lys | Pro | Gly | Ile | Tyr | Arg |
|---|---|---|---|---|---|---|---|---|---|---|---|---|---|---|---|
| 65 | | | | | 70 | | | | | 75 | | | | | 80 |

| Phe | Val | Ala | Pro | Gly | Glu | Arg | Pro | Ser | Gly | Met | Phe | Asp | Ser | Ser | Val |
|---|---|---|---|---|---|---|---|---|---|---|---|---|---|---|---|
| | | | | 85 | | | | | 90 | | | | | 95 | |

| Leu | Cys | Glu | Cys | Pro | Asn |
|---|---|---|---|---|---|
| | | | 100 | | |

5,885,799

(2) INFORMATION FOR SEQ ID NO:81:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..495

(xi) SEQUENCE DESCRIPTION: SEQ ID NO:81:

```
ATT  CGG  TCC  ATT  GAG  ACA  ATC  ACG  CTC  CCC  CAG  GAT  GCT  GTC  TCC  CGC      48
Ile  Arg  Ser  Ile  Glu  Thr  Ile  Thr  Leu  Pro  Gln  Asp  Ala  Val  Ser  Arg
 1                   5                  10                       15

ACT  CAA  CGT  CGG  GGC  AGG  ACT  GGC  AGG  GGG  AAG  CCA  GGC  ATC  TAC  AGA      96
Thr  Gln  Arg  Arg  Gly  Arg  Thr  Gly  Arg  Gly  Lys  Pro  Gly  Ile  Tyr  Arg
              20                           25                       30

TTT  GTG  GCA  CCG  GGG  GAG  CGC  CCC  TCC  GGC  ATG  TTC  GAC  TCG  TCC  GTC     144
Phe  Val  Ala  Pro  Gly  Glu  Arg  Pro  Ser  Gly  Met  Phe  Asp  Ser  Ser  Val
          35                       40                       45

CTC  TGT  GAG  TGC  TAT  GAC  GCA  GGC  TGT  GCT  TGG  TAT  GAG  CTC  ACG  CCC     192
Leu  Cys  Glu  Cys  Tyr  Asp  Ala  Gly  Cys  Ala  Trp  Tyr  Glu  Leu  Thr  Pro
     50                       55                       60

GCC  GAG  ACT  ACA  GTT  AGG  CTA  CGA  GCG  TAC  ATG  AAC  ACC  CCG  GGG  CTT     240
Ala  Glu  Thr  Thr  Val  Arg  Leu  Arg  Ala  Tyr  Met  Asn  Thr  Pro  Gly  Leu
 65                       70                       75                       80

CCC  GTG  TGC  CAG  GAC  CAT  CTT  GAA  TTT  TGG  GAG  GGC  GTC  TTT  ACA  GGC     288
Pro  Val  Cys  Gln  Asp  His  Leu  Glu  Phe  Trp  Glu  Gly  Val  Phe  Thr  Gly
                    85                       90                       95

CTC  ACT  CAT  ATA  GAT  GCC  CAC  TTT  CTA  TCC  CAG  ACA  AAG  CAG  AGT  GGG     336
Leu  Thr  His  Ile  Asp  Ala  His  Phe  Leu  Ser  Gln  Thr  Lys  Gln  Ser  Gly
               100                      105                      110

GAG  AAC  CTT  CCT  TAC  CTG  GTA  GCG  TAC  CAA  GCC  ACC  GTG  TGC  GCT  AGG     384
Glu  Asn  Leu  Pro  Tyr  Leu  Val  Ala  Tyr  Gln  Ala  Thr  Val  Cys  Ala  Arg
          115                      120                      125

GCT  CAA  GCC  CCT  CCC  CCA  TCG  TGG  GAC  CAG  ATG  TGG  AAG  TGT  TTG  ATT     432
Ala  Gln  Ala  Pro  Pro  Pro  Ser  Trp  Asp  Gln  Met  Trp  Lys  Cys  Leu  Ile
130                      135                      140

CGC  CTC  AAG  CCC  ACC  CTC  CAT  GGG  CCA  ACA  CCC  CTG  CTA  TAC  AGA  CTG     480
Arg  Leu  Lys  Pro  Thr  Leu  His  Gly  Pro  Thr  Pro  Leu  Leu  Tyr  Arg  Leu
145                      150                      155                      160

GGC  GCT  GCC  GAA  TTC                                                            495
Gly  Ala  Ala  Glu  Phe
               165
```

(2) INFORMATION FOR SEQ ID NO:82:

(i) SEQUENCE CHARACTERISTICS:
        (A) LENGTH: 165 amino acids
        (B) TYPE: amino acid
        (D) TOPOLOGY: linear (ii) MOLECULE TYPE: protein (xi) SEQUENCE DESCRIPTION: SEQ ID NO:82:

```
Ile  Arg  Ser  Ile  Glu  Thr  Ile  Thr  Leu  Pro  Gln  Asp  Ala  Val  Ser  Arg
 1                   5                  10                       15

Thr  Gln  Arg  Arg  Gly  Arg  Thr  Gly  Arg  Gly  Lys  Pro  Gly  Ile  Tyr  Arg
              20                           25                       30

Phe  Val  Ala  Pro  Gly  Glu  Arg  Pro  Ser  Gly  Met  Phe  Asp  Ser  Ser  Val
```

|   |   |   | 35 |   |   |   |   | 40 |   |   |   |   | 45 |   |   |
|---|---|---|---|---|---|---|---|---|---|---|---|---|---|---|---|
| Leu | Cys 50 | Glu | Cys | Tyr | Asp | Ala 55 | Gly | Cys | Ala | Trp | Tyr 60 | Glu | Leu | Thr | Pro |
| Ala 65 | Glu | Thr | Thr | Val 70 | Arg | Leu | Arg | Ala | Tyr 75 | Met | Asn | Thr | Pro | Gly | Leu 80 |
| Pro | Val | Cys | Gln | Asp 85 | His | Leu | Glu | Phe | Trp 90 | Glu | Gly | Val | Phe | Thr 95 | Gly |
| Leu | Thr | His | Ile 100 | Asp | Ala | His | Phe | Leu 105 | Ser | Gln | Thr | Lys | Gln 110 | Ser | Gly |
| Glu | Asn | Leu 115 | Pro | Tyr | Leu | Val | Ala 120 | Tyr | Gln | Ala | Thr | Val 125 | Cys | Ala | Arg |
| Ala | Gln 130 | Ala | Pro | Pro | Pro | Ser 135 | Trp | Asp | Gln | Met | Trp 140 | Lys | Cys | Leu | Ile |
| Arg 145 | Leu | Lys | Pro | Thr | Leu 150 | His | Gly | Pro | Thr | Pro 155 | Leu | Leu | Tyr | Arg | Leu 160 |
| Gly | Ala | Ala | Glu | Phe 165 |   |   |   |   |   |   |   |   |   |   |   |

( 2 ) INFORMATION FOR SEQ ID NO:83:

( i ) SEQUENCE CHARACTERISTICS:
    ( A ) LENGTH: 816 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 1..816

( x i ) SEQUENCE DESCRIPTION: SEQ ID NO:83:

| GAA | TTC | GGG | GCG | GTG | GAC | TTT | ATC | CCT | GTG | GAG | AAC | CTA | GAG | ACA | ACC | 48 |
|---|---|---|---|---|---|---|---|---|---|---|---|---|---|---|---|---|
| Glu 1 | Phe | Gly | Ala | Val 5 | Asp | Phe | Ile | Pro | Val 10 | Glu | Asn | Leu | Glu | Thr 15 | Thr |  |
| ATG | AGG | TCC | CCG | GTG | TTC | ACG | GAT | AAC | TCC | TCT | CCA | CCA | GTA | GTG | CCC | 96 |
| Met | Arg | Ser | Pro 20 | Val | Phe | Thr | Asp | Asn 25 | Ser | Ser | Pro | Pro | Val 30 | Val | Pro |  |
| CAG | AGC | TTC | CAG | GTG | GCT | CAC | CTC | CAT | GCT | CCC | ACA | GGC | AGC | GGC | AAA | 144 |
| Gln | Ser | Phe | Gln 35 | Val | Ala | His | Leu | His 40 | Ala | Pro | Thr | Gly | Ser 45 | Gly | Lys |  |
| AGC | ACC | AAG | GTC | CCG | GCT | GCA | TAT | GCA | GCT | CAG | GGC | TAT | AAG | GTG | CTA | 192 |
| Ser | Thr | Lys 50 | Val | Pro | Ala | Ala 55 | Tyr | Ala | Ala | Gln | Gly 60 | Tyr | Lys | Val | Leu |  |
| GTA | CTC | AAC | CCC | TCT | GTT | GCT | GCA | ACA | CTG | GGC | TTT | GGT | GCT | TAC | ATG | 240 |
| Val 65 | Leu | Asn | Pro | Ser | Val 70 | Ala | Ala | Thr | Leu | Gly 75 | Phe | Gly | Ala | Tyr | Met 80 |  |
| TCC | AAG | GCT | CAT | GGG | ATC | GAT | CCT | AAC | ATC | AGG | ACC | GGG | GTG | AGA | ACA | 288 |
| Ser | Lys | Ala | His | Gly 85 | Ile | Asp | Pro | Asn | Ile 90 | Arg | Thr | Gly | Val | Arg 95 | Thr |  |
| ATT | ACC | ACT | GGC | AGC | CCC | ATC | ACG | TAC | TCC | ACC | TAC | GGC | AAG | TTC | CTT | 336 |
| Ile | Thr | Thr | Gly 100 | Ser | Pro | Ile | Thr | Tyr 105 | Ser | Thr | Tyr | Gly | Lys 110 | Phe | Leu |  |
| GCC | GAC | GGC | GGG | TGC | TCG | GGG | GCT | TAT | GAC | ATA | ATA | ATT | TGT | GAC | 384 |   |
| Ala | Asp | Gly 115 | Gly | Cys | Ser | Gly | Gly 120 | Ala | Tyr | Asp | Ile | Ile 125 | Ile | Cys | Asp |  |
| GAG | TGC | CAC | TCC | ACG | GAT | GCC | ACA | TCC | ATC | TTG | GGC | ATT | GGC | ACT | GTC | 432 |
| Glu | Cys 130 | His | Ser | Thr | Asp | Ala 135 | Thr | Ser | Ile | Leu | Gly 140 | Ile | Gly | Thr | Val |  |
| CTT | GAC | CAA | GCA | GAG | ACT | GCG | GGG | GCG | AGA | CTG | GTT | GTG | CTC | GCC | ACC | 480 |
| Leu | Asp | Gln | Ala | Glu 150 | Thr | Ala | Gly | Ala | Arg 155 | Leu | Val | Val | Leu | Ala 160 | Thr |  |

```
GCC  ACC  CCT  CCG  GGC  TCC  GTC  ACT  GTG  CCC  CAT  CCC  AAC  ATC  GAG  GAG      528
Ala  Thr  Pro  Pro  Gly  Ser  Val  Thr  Val  Pro  His  Pro  Asn  Ile  Glu  Glu
               165                      170                      175

GTT  GCT  CTG  TCC  ACC  ACC  GGA  GAG  ATC  CCT  TTT  TAC  GGC  AAG  GCT  ATC      576
Val  Ala  Leu  Ser  Thr  Thr  Gly  Glu  Ile  Pro  Phe  Tyr  Gly  Lys  Ala  Ile
               180                      185                      190

CCC  CTC  GAA  GTA  ATC  AAG  GGG  GGG  AGA  CAT  CTC  ATC  TTC  TGT  CAT  TCA      624
Pro  Leu  Glu  Val  Ile  Lys  Gly  Gly  Arg  His  Leu  Ile  Phe  Cys  His  Ser
               195                      200                      205

AAG  AAG  AAG  TGC  GAC  GAA  CTC  GCC  GCA  AAG  CTG  GTC  GCA  TTG  GGC  ATC      672
Lys  Lys  Lys  Cys  Asp  Glu  Leu  Ala  Ala  Lys  Leu  Val  Ala  Leu  Gly  Ile
               210                      215                      220

AAT  GCC  GTG  GCC  TAC  TAC  CGC  GGT  CTT  GAC  GTG  TCC  GTC  ATC  CCG  ACC      720
Asn  Ala  Val  Ala  Tyr  Tyr  Arg  Gly  Leu  Asp  Val  Ser  Val  Ile  Pro  Thr
225                      230                      235                      240

AGC  GGC  GAT  GTT  GTC  GTC  GTG  GCA  ACC  GAT  GCC  CTC  ATG  ACC  GGC  TAT      768
Ser  Gly  Asp  Val  Val  Val  Val  Ala  Thr  Asp  Ala  Leu  Met  Thr  Gly  Tyr
               245                      250                      255

ACC  GGC  GAC  TTC  GAC  TCG  GTG  ATA  GAC  TGC  AAT  ACG  TGT  GCC  GAA  TTC      816
Thr  Gly  Asp  Phe  Asp  Ser  Val  Ile  Asp  Cys  Asn  Thr  Cys  Ala  Glu  Phe
               260                      265                      270
```

( 2 ) INFORMATION FOR SEQ ID NO:84:

( i ) SEQUENCE CHARACTERISTICS:
        ( A ) LENGTH: 272 amino acids
        ( B ) TYPE: amino acid
        ( D ) TOPOLOGY: linear ( i i ) MOLECULE TYPE: protein ( x i ) SEQUENCE DESCRIPTION: SEQ ID NO:84:

```
Glu  Phe  Gly  Ala  Val  Asp  Phe  Ile  Pro  Val  Glu  Asn  Leu  Glu  Thr  Thr
 1                    5                      10                      15

Met  Arg  Ser  Pro  Val  Phe  Thr  Asp  Asn  Ser  Ser  Pro  Pro  Val  Val  Pro
               20                      25                      30

Gln  Ser  Phe  Gln  Val  Ala  His  Leu  His  Ala  Pro  Thr  Gly  Ser  Gly  Lys
               35                      40                      45

Ser  Thr  Lys  Val  Pro  Ala  Ala  Tyr  Ala  Ala  Gln  Gly  Tyr  Lys  Val  Leu
      50                      55                      60

Val  Leu  Asn  Pro  Ser  Val  Ala  Ala  Thr  Leu  Gly  Phe  Gly  Ala  Tyr  Met
 65                      70                      75                      80

Ser  Lys  Ala  His  Gly  Ile  Asp  Pro  Asn  Ile  Arg  Thr  Gly  Val  Arg  Thr
                85                      90                      95

Ile  Thr  Thr  Gly  Ser  Pro  Ile  Thr  Tyr  Ser  Thr  Tyr  Gly  Lys  Phe  Leu
               100                     105                     110

Ala  Asp  Gly  Gly  Cys  Ser  Gly  Gly  Ala  Tyr  Asp  Ile  Ile  Ile  Cys  Asp
               115                     120                     125

Glu  Cys  His  Ser  Thr  Asp  Ala  Thr  Ser  Ile  Leu  Gly  Ile  Gly  Thr  Val
     130                     135                     140

Leu  Asp  Gln  Ala  Glu  Thr  Ala  Gly  Ala  Arg  Leu  Val  Val  Leu  Ala  Thr
145                     150                     155                     160

Ala  Thr  Pro  Pro  Gly  Ser  Val  Thr  Val  Pro  His  Pro  Asn  Ile  Glu  Glu
               165                     170                     175

Val  Ala  Leu  Ser  Thr  Thr  Gly  Glu  Ile  Pro  Phe  Tyr  Gly  Lys  Ala  Ile
               180                     185                     190

Pro  Leu  Glu  Val  Ile  Lys  Gly  Gly  Arg  His  Leu  Ile  Phe  Cys  His  Ser
               195                     200                     205
```

| | | | | | | | | | | | | | | | |
|---|---|---|---|---|---|---|---|---|---|---|---|---|---|---|---|
| Lys | Lys | Lys | Cys | Asp | Glu | Leu | Ala | Ala | Lys | Leu | Val | Ala | Leu | Gly | Ile |
| | 210 | | | | 215 | | | | | 220 | | | | | |
| Asn | Ala | Val | Ala | Tyr | Tyr | Arg | Gly | Leu | Asp | Val | Ser | Val | Ile | Pro | Thr |
| 225 | | | | | 230 | | | | 235 | | | | | | 240 |
| Ser | Gly | Asp | Val | Val | Val | Ala | Thr | Asp | Ala | Leu | Met | Thr | Gly | Tyr | |
| | | | | 245 | | | | 250 | | | | | 255 | | |
| Thr | Gly | Asp | Phe | Asp | Ser | Val | Ile | Asp | Cys | Asn | Thr | Cys | Ala | Glu | Phe |
| | | | | 260 | | | | 265 | | | | 270 | | | |

( 2 ) INFORMATION FOR SEQ ID NO:85:

( i ) SEQUENCE CHARACTERISTICS:
        ( A ) LENGTH: 2523 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..2523

( x i ) SEQUENCE DESCRIPTION: SEQ ID NO:85:

| | | | | | | | | | | | | | | | | |
|---|---|---|---|---|---|---|---|---|---|---|---|---|---|---|---|---|
| ATG | GCT | ACA | AAC | CCT | GTT | TGC | GTT | TTG | AAG | GGT | GAC | GGC | CCA | GTT | CAA | 48 |
| Met | Ala | Thr | Asn | Pro | Val | Cys | Val | Leu | Lys | Gly | Asp | Gly | Pro | Val | Gln | |
| 1 | | | | 5 | | | | | 10 | | | | | 15 | | |
| GGT | ATT | ATT | AAC | TTC | GAG | CAG | AAG | GAA | AGT | AAT | GGA | CCA | GTG | AAG | GTG | 96 |
| Gly | Ile | Ile | Asn | Phe | Glu | Gln | Lys | Glu | Ser | Asn | Gly | Pro | Val | Lys | Val | |
| | | | 20 | | | | | 25 | | | | | 30 | | | |
| TGG | GGA | AGC | ATT | AAA | GGA | CTG | ACT | GAA | GGC | CTG | CAT | GGA | TTC | CAT | GTT | 144 |
| Trp | Gly | Ser | Ile | Lys | Gly | Leu | Thr | Glu | Gly | Leu | His | Gly | Phe | His | Val | |
| | | 35 | | | | | 40 | | | | | 45 | | | | |
| CAT | GAG | TTT | GGA | GAT | AAT | ACA | GCA | GGC | TGT | ACC | AGT | CCA | GGT | CCT | CAC | 192 |
| His | Glu | Phe | Gly | Asp | Asn | Thr | Ala | Gly | Cys | Thr | Ser | Pro | Gly | Pro | His | |
| | 50 | | | | | 55 | | | | | 60 | | | | | |
| TTT | AAT | CCT | CTA | TCC | AGA | AAA | CAC | GGT | GGG | CCA | AAG | GAT | GAA | GAG | AGG | 240 |
| Phe | Asn | Pro | Leu | Ser | Arg | Lys | His | Gly | Gly | Pro | Lys | Asp | Glu | Glu | Arg | |
| 65 | | | | | 70 | | | | | 75 | | | | | 80 | |
| CAT | GTT | GGA | GAC | TTG | GGC | AAT | GTG | ACT | GCT | GAC | AAA | GAT | GGT | GTG | GCC | 288 |
| His | Val | Gly | Asp | Leu | Gly | Asn | Val | Thr | Ala | Asp | Lys | Asp | Gly | Val | Ala | |
| | | | | 85 | | | | | 90 | | | | | 95 | | |
| GAT | GTG | TCT | ATT | GAA | GAT | TCT | GTG | ATC | TCA | CTC | TCA | GGA | GAC | CAT | TGC | 336 |
| Asp | Val | Ser | Ile | Glu | Asp | Ser | Val | Ile | Ser | Leu | Ser | Gly | Asp | His | Cys | |
| | | | 100 | | | | | 105 | | | | | 110 | | | |
| ATC | ATT | GGC | CGC | ACA | CTG | GTG | GTC | CAT | GAA | AAA | GCA | GAT | GAC | TTG | GGC | 384 |
| Ile | Ile | Gly | Arg | Thr | Leu | Val | Val | His | Glu | Lys | Ala | Asp | Asp | Leu | Gly | |
| | | 115 | | | | | 120 | | | | | 125 | | | | |
| AAA | GGT | GGA | AAT | GAA | GAA | AGT | ACA | AAG | ACA | GGA | AAC | GCT | GGA | AGT | CGT | 432 |
| Lys | Gly | Gly | Asn | Glu | Glu | Ser | Thr | Lys | Thr | Gly | Asn | Ala | Gly | Ser | Arg | |
| | 130 | | | | | 135 | | | | | 140 | | | | | |
| TTG | GCT | TGT | GGT | GTA | ATT | GGG | ATC | CGA | ATT | CGG | GGC | ACC | TAT | GTT | TAT | 480 |
| Leu | Ala | Cys | Gly | Val | Ile | Gly | Ile | Arg | Ile | Arg | Gly | Thr | Tyr | Val | Tyr | |
| 145 | | | | | 150 | | | | | 155 | | | | | 160 | |
| AAC | CAT | CTC | ACT | CCT | CTT | CGG | GAC | TGG | GCG | CAC | AAC | GGC | TTG | CGA | GAT | 528 |
| Asn | His | Leu | Thr | Pro | Leu | Arg | Asp | Trp | Ala | His | Asn | Gly | Leu | Arg | Asp | |
| | | | | 165 | | | | | 170 | | | | | 175 | | |
| CTG | GCC | GTG | GCT | GTA | GAG | CCA | GTC | GTC | TTC | TCC | CAA | ATG | GAG | ACC | AAG | 576 |
| Leu | Ala | Val | Ala | Val | Glu | Pro | Val | Val | Phe | Ser | Gln | Met | Glu | Thr | Lys | |
| | | | 180 | | | | | 185 | | | | | 190 | | | |
| CTC | ATC | ACG | TGG | GGG | GCA | GAT | ACC | GCC | GCG | TGC | GGT | GAC | ATC | ATC | AAC | 624 |
| Leu | Ile | Thr | Trp | Gly | Ala | Asp | Thr | Ala | Ala | Cys | Gly | Asp | Ile | Ile | Asn | |
| | | 195 | | | | | 200 | | | | | 205 | | | | |
| GGC | TTG | CCT | GTT | TCC | GCC | CGC | AGG | GGC | CGG | GAG | ATA | CTG | CTC | GGG | CCA | 672 |

-continued

```
            Gly  Leu  Pro  Val  Ser  Ala  Arg  Arg  Gly  Arg  Glu  Ile  Leu  Leu  Gly  Pro
                 210                      215                      220

GCC  GAT  GGA  ATG  GTG  TCC  AAG  GGT  TGG  AGG  TTG  CTG  GCG  CCC  ATC  ACG              720
Ala  Asp  Gly  Met  Val  Ser  Lys  Gly  Trp  Arg  Leu  Leu  Ala  Pro  Ile  Thr
225                      230                      235                      240

GCG  TAC  GCC  CAG  CAG  ACA  AGG  GGC  CTC  CTA  GGG  TGC  ATA  ATC  ACC  AGC              768
Ala  Tyr  Ala  Gln  Gln  Thr  Arg  Gly  Leu  Leu  Gly  Cys  Ile  Ile  Thr  Ser
                         245                      250                      255

CTA  ACT  GGC  CGG  GAC  AAA  AAC  CAA  GTG  GAG  GGT  GAG  GTC  CAG  ATT  GTG              816
Leu  Thr  Gly  Arg  Asp  Lys  Asn  Gln  Val  Glu  Gly  Glu  Val  Gln  Ile  Val
               260                      265                      270

TCA  ACT  GCT  GCC  CAA  ACC  TTC  CTG  GCA  ACG  TGC  ATC  ATC  AAT  GGG  GTG              864
Ser  Thr  Ala  Ala  Gln  Thr  Phe  Leu  Ala  Thr  Cys  Ile  Ile  Asn  Gly  Val
          275                      280                      285

TGC  TGG  ACT  GTC  TAC  CAC  GGG  GCC  GGA  ACG  AGG  ACC  ATC  GCG  TCA  CCC              912
Cys  Trp  Thr  Val  Tyr  His  Gly  Ala  Gly  Thr  Arg  Thr  Ile  Ala  Ser  Pro
     290                      295                      300

AAG  GGT  CCT  GTC  ATC  CAG  ATG  TAT  ACC  AAT  GTA  GAC  CAA  GAC  CTT  GTG              960
Lys  Gly  Pro  Val  Ile  Gln  Met  Tyr  Thr  Asn  Val  Asp  Gln  Asp  Leu  Val
305                      310                      315                      320

GGC  TGG  CCC  GCT  TCG  CAA  GGT  ACC  CGC  TCA  TTG  ACA  CCC  TGC  ACT  TGC             1008
Gly  Trp  Pro  Ala  Ser  Gln  Gly  Thr  Arg  Ser  Leu  Thr  Pro  Cys  Thr  Cys
                         325                      330                      335

GGC  TCC  TCG  GAC  CTT  TAC  CTG  GTC  ACG  AGG  CAC  GCC  GAT  GTC  ATT  CCC             1056
Gly  Ser  Ser  Asp  Leu  Tyr  Leu  Val  Thr  Arg  His  Ala  Asp  Val  Ile  Pro
               340                      345                      350

GTG  CGC  CGG  CGG  GGT  GAT  AGC  AGG  GGC  AGC  CTG  CTG  TCG  CCC  CGG  CCC             1104
Val  Arg  Arg  Arg  Gly  Asp  Ser  Arg  Gly  Ser  Leu  Leu  Ser  Pro  Arg  Pro
          355                      360                      365

ATT  TCC  TAC  TTG  AAA  GGC  TCC  TCG  GGG  GGT  CCG  CTG  TTG  TGC  CCC  GCG             1152
Ile  Ser  Tyr  Leu  Lys  Gly  Ser  Ser  Gly  Gly  Pro  Leu  Leu  Cys  Pro  Ala
     370                      375                      380

GGG  CAC  GCC  GTG  GGC  ATA  TTT  AGG  GCC  GCG  GTG  TGC  ACC  CGT  GGA  GTG             1200
Gly  His  Ala  Val  Gly  Ile  Phe  Arg  Ala  Ala  Val  Cys  Thr  Arg  Gly  Val
385                      390                      395                      400

GCT  AAG  GCG  GTG  GAC  TTT  ATC  CCT  GTG  GAG  AAC  CTA  GAG  ACA  ACC  ATG             1248
Ala  Lys  Ala  Val  Asp  Phe  Ile  Pro  Val  Glu  Asn  Leu  Glu  Thr  Thr  Met
                         405                      410                      415

AGG  TCC  CCG  GTG  TTC  ACG  GAT  AAC  TCC  TCT  CCA  CCA  GTA  GTG  CCC  CAG             1296
Arg  Ser  Pro  Val  Phe  Thr  Asp  Asn  Ser  Ser  Pro  Pro  Val  Val  Pro  Gln
               420                      425                      430

AGC  TTC  CAG  GTG  GCT  CAC  CTC  CAT  GCT  CCC  ACA  GGC  AGC  GGC  AAA  AGC             1344
Ser  Phe  Gln  Val  Ala  His  Leu  His  Ala  Pro  Thr  Gly  Ser  Gly  Lys  Ser
          435                      440                      445

ACC  AAG  GTC  CCG  GCT  GCA  TAT  GCA  GCT  CAG  GGC  TAT  AAG  GTG  CTA  GTA             1392
Thr  Lys  Val  Pro  Ala  Ala  Tyr  Ala  Ala  Gln  Gly  Tyr  Lys  Val  Leu  Val
     450                      455                      460

CTC  AAC  CCC  TCT  GTT  GCT  GCA  ACA  CTG  GGC  TTT  GGT  GCT  TAC  ATG  TCC             1440
Leu  Asn  Pro  Ser  Val  Ala  Ala  Thr  Leu  Gly  Phe  Gly  Ala  Tyr  Met  Ser
465                      470                      475                      480

AAG  GCT  CAT  GGG  ATC  GAT  CCT  AAC  ATC  AGG  ACC  GGG  GTG  AGA  ACA  ATT             1488
Lys  Ala  His  Gly  Ile  Asp  Pro  Asn  Ile  Arg  Thr  Gly  Val  Arg  Thr  Ile
                         485                      490                      495

ACC  ACT  GGC  AGC  CCC  ATC  ACG  TAC  TCC  ACC  TAC  GGC  AAG  TTC  CTT  GCC             1536
Thr  Thr  Gly  Ser  Pro  Ile  Thr  Tyr  Ser  Thr  Tyr  Gly  Lys  Phe  Leu  Ala
               500                      505                      510

GAC  GGC  GGG  TGC  TCG  GGG  GGC  GCT  TAT  GAC  ATA  ATA  ATT  TGT  GAC  GAG             1584
Asp  Gly  Gly  Cys  Ser  Gly  Gly  Ala  Tyr  Asp  Ile  Ile  Ile  Cys  Asp  Glu
          515                      520                      525

TGC  CAC  TCC  ACG  GAT  GCC  ACA  TCC  ATC  TTG  GGC  ATT  GGC  ACT  GTC  CTT             1632
```

```
Cys His Ser Thr Asp Ala Thr Ser Ile Leu Gly Ile Gly Thr Val Leu
    530                 535                 540

GAC CAA GCA GAG ACT GCG GGG GCG AGA CTG GTT GTG CTC GCC ACC GCC      1680
Asp Gln Ala Glu Thr Ala Gly Ala Arg Leu Val Val Leu Ala Thr Ala
545                 550                 555                 560

ACC CCT CCG GGC TCC GTC ACT GTG CCC CAT CCC AAC ATC GAG GAG GTT      1728
Thr Pro Pro Gly Ser Val Thr Val Pro His Pro Asn Ile Glu Glu Val
                565                 570                 575

GCT CTG TCC ACC ACC GGA GAG ATC CCT TTT TAC GGC AAG GCT ATC CCC      1776
Ala Leu Ser Thr Thr Gly Glu Ile Pro Phe Tyr Gly Lys Ala Ile Pro
            580                 585                 590

CTC GAA GTA ATC AAG GGG GGG AGA CAT CTC ATC TTC TGT CAT TCA AAG      1824
Leu Glu Val Ile Lys Gly Gly Arg His Leu Ile Phe Cys His Ser Lys
        595                 600                 605

AAG AAG TGC GAC GAA CTC GCC GCA AAG CTG GTC GCA TTG GGC ATC AAT      1872
Lys Lys Cys Asp Glu Leu Ala Ala Lys Leu Val Ala Leu Gly Ile Asn
    610                 615                 620

GCC GTG GCC TAC TAC CGC GGT CTT GAC GTG TCC GTC ATC CCG ACC AGC      1920
Ala Val Ala Tyr Tyr Arg Gly Leu Asp Val Ser Val Ile Pro Thr Ser
625                 630                 635                 640

GGC GAT GTT GTC GTC GTG GCA ACC GAT GCC CTC ATG ACC GGC TAT ACC      1968
Gly Asp Val Val Val Val Ala Thr Asp Ala Leu Met Thr Gly Tyr Thr
                645                 650                 655

GGC GAC TTC GAC TCG GTG ATA GAC TGC AAT ACG TGT GTC ACC CAG ACA      2016
Gly Asp Phe Asp Ser Val Ile Asp Cys Asn Thr Cys Val Thr Gln Thr
            660                 665                 670

GTC GAT TTC AGC CTT GAC CCT ACC TTC ACC ATT GAG ACA ATC ACG CTC      2064
Val Asp Phe Ser Leu Asp Pro Thr Phe Thr Ile Glu Thr Ile Thr Leu
        675                 680                 685

CCC CAA GAT GCT GTC TCC CGC ACT CAA CGT CGG GGC AGG ACT GGC AGG      2112
Pro Gln Asp Ala Val Ser Arg Thr Gln Arg Arg Gly Arg Thr Gly Arg
    690                 695                 700

GGG AAG CCA GGC ATC TAC AGA TTT GTG GCA CCG GGG GAG CGC CCT CCC      2160
Gly Lys Pro Gly Ile Tyr Arg Phe Val Ala Pro Gly Glu Arg Pro Pro
705                 710                 715                 720

GGC ATG TTC GAC TCG TCC GTC CTC TGT GAG TGC TAT GAC GCA GGC TGT      2208
Gly Met Phe Asp Ser Ser Val Leu Cys Glu Cys Tyr Asp Ala Gly Cys
                725                 730                 735

GCT TGG TAT GAG CTC ACG CCC GCC GAG ACT ACA GTT AGG CTA CGA GCG      2256
Ala Trp Tyr Glu Leu Thr Pro Ala Glu Thr Thr Val Arg Leu Arg Ala
            740                 745                 750

TAC ATG AAC ACC CCG GGG CTT CCC GTG TGC CAG GAC CAT CTT GAA TTT      2304
Tyr Met Asn Thr Pro Gly Leu Pro Val Cys Gln Asp His Leu Glu Phe
        755                 760                 765

TGG GAG GGC GTC TTT ACA GGC CTC ACT CAT ATA GAT GCC CAC TTT CTA      2352
Trp Glu Gly Val Phe Thr Gly Leu Thr His Ile Asp Ala His Phe Leu
    770                 775                 780

TCC CAG ACA AAG CAG AGT GGG GAG AAC CTT CCT TAC CTG GTA GCG TAC      2400
Ser Gln Thr Lys Gln Ser Gly Glu Asn Leu Pro Tyr Leu Val Ala Tyr
785                 790                 795                 800

CAA GCC ACC GTG TGC GCT AGG GCT CAA GCC CCT CCC CCA TCG TGG GAC      2448
Gln Ala Thr Val Cys Ala Arg Ala Gln Ala Pro Pro Pro Ser Trp Asp
                805                 810                 815

CAG ATG TGG AAG TGT TTG ATT CGC CTC AAG CCC ACC CTC CAT GGG CCA      2496
Gln Met Trp Lys Cys Leu Ile Arg Leu Lys Pro Thr Leu His Gly Pro
            820                 825                 830

ACA CCC CTG CTA TAC AGA CTG GGC GCT                                  2523
Thr Pro Leu Leu Tyr Arg Leu Gly Ala
        835                 840
```

(2) INFORMATION FOR SEQ ID NO:86:

(i) SEQUENCE CHARACTERISTICS:
        (A) LENGTH: 841 amino acids
        (B) TYPE: amino acid
        (D) TOPOLOGY: linear (ii) MOLECULE TYPE: protein (xi) SEQUENCE DESCRIPTION: SEQ ID NO:86:

```
Met Ala Thr Asn Pro Val Cys Val Leu Lys Gly Asp Gly Pro Val Gln
 1               5                  10                  15
Gly Ile Ile Asn Phe Glu Gln Lys Glu Ser Asn Gly Pro Val Lys Val
            20                  25                  30
Trp Gly Ser Ile Lys Gly Leu Thr Glu Gly Leu His Gly Phe His Val
        35                  40                  45
His Glu Phe Gly Asp Asn Thr Ala Gly Cys Thr Ser Pro Gly Pro His
    50                  55                  60
Phe Asn Pro Leu Ser Arg Lys His Gly Gly Pro Lys Asp Glu Glu Arg
65                  70                  75                  80
His Val Gly Asp Leu Gly Asn Val Thr Ala Asp Lys Asp Gly Val Ala
                85                  90                  95
Asp Val Ser Ile Glu Asp Ser Val Ile Ser Leu Ser Gly Asp His Cys
            100                 105                 110
Ile Ile Gly Arg Thr Leu Val Val His Glu Lys Ala Asp Asp Leu Gly
        115                 120                 125
Lys Gly Gly Asn Glu Glu Ser Thr Lys Thr Gly Asn Ala Gly Ser Arg
    130                 135                 140
Leu Ala Cys Gly Val Ile Gly Ile Arg Ile Arg Gly Thr Tyr Val Tyr
145                 150                 155                 160
Asn His Leu Thr Pro Leu Arg Asp Trp Ala His Asn Gly Leu Arg Asp
                165                 170                 175
Leu Ala Val Ala Val Glu Pro Val Val Phe Ser Gln Met Glu Thr Lys
            180                 185                 190
Leu Ile Thr Trp Gly Ala Asp Thr Ala Ala Cys Gly Asp Ile Ile Asn
        195                 200                 205
Gly Leu Pro Val Ser Ala Arg Arg Gly Arg Glu Ile Leu Leu Gly Pro
    210                 215                 220
Ala Asp Gly Met Val Ser Lys Gly Trp Arg Leu Leu Ala Pro Ile Thr
225                 230                 235                 240
Ala Tyr Ala Gln Gln Thr Arg Gly Leu Leu Gly Cys Ile Ile Thr Ser
                245                 250                 255
Leu Thr Gly Arg Asp Lys Asn Gln Val Glu Gly Glu Val Gln Ile Val
            260                 265                 270
Ser Thr Ala Ala Gln Thr Phe Leu Ala Thr Cys Ile Ile Asn Gly Val
        275                 280                 285
Cys Trp Thr Val Tyr His Gly Ala Gly Thr Arg Thr Ile Ala Ser Pro
    290                 295                 300
Lys Gly Pro Val Ile Gln Met Tyr Thr Asn Val Asp Gln Asp Leu Val
305                 310                 315                 320
Gly Trp Pro Ala Ser Gln Gly Thr Arg Ser Leu Thr Pro Cys Thr Cys
                325                 330                 335
Gly Ser Ser Asp Leu Tyr Leu Val Thr Arg His Ala Asp Val Ile Pro
            340                 345                 350
Val Arg Arg Arg Gly Asp Ser Arg Gly Ser Leu Leu Ser Pro Arg Pro
        355                 360                 365
```

-continued

```
Ile  Ser  Tyr  Leu  Lys  Gly  Ser  Ser  Gly  Gly  Pro  Leu  Leu  Cys  Pro  Ala
     370                 375                 380

Gly  His  Ala  Val  Gly  Ile  Phe  Arg  Ala  Ala  Val  Cys  Thr  Arg  Gly  Val
385                      390                 395                           400

Ala  Lys  Ala  Val  Asp  Phe  Ile  Pro  Val  Glu  Asn  Leu  Glu  Thr  Thr  Met
                    405                      410                      415

Arg  Ser  Pro  Val  Phe  Thr  Asp  Asn  Ser  Ser  Pro  Val  Val  Pro  Gln
                    420                 425                      430

Ser  Phe  Gln  Val  Ala  His  Leu  His  Ala  Pro  Thr  Gly  Ser  Gly  Lys  Ser
          435                      440                      445

Thr  Lys  Val  Pro  Ala  Ala  Tyr  Ala  Ala  Gln  Gly  Tyr  Lys  Val  Leu  Val
     450                      455                 460

Leu  Asn  Pro  Ser  Val  Ala  Ala  Thr  Leu  Gly  Phe  Gly  Ala  Tyr  Met  Ser
465                      470                 475                           480

Lys  Ala  His  Gly  Ile  Asp  Pro  Asn  Ile  Arg  Thr  Gly  Val  Arg  Thr  Ile
                    485                 490                           495

Thr  Thr  Gly  Ser  Pro  Ile  Thr  Tyr  Ser  Thr  Tyr  Gly  Lys  Phe  Leu  Ala
                    500                 505                      510

Asp  Gly  Gly  Cys  Ser  Gly  Gly  Ala  Tyr  Asp  Ile  Ile  Ile  Cys  Asp  Glu
          515                      520                      525

Cys  His  Ser  Thr  Asp  Ala  Thr  Ser  Ile  Leu  Gly  Ile  Gly  Thr  Val  Leu
     530                      535                 540

Asp  Gln  Ala  Glu  Thr  Ala  Gly  Ala  Arg  Leu  Val  Val  Leu  Ala  Thr  Ala
545                      550                      555                      560

Thr  Pro  Pro  Gly  Ser  Val  Thr  Val  Pro  His  Pro  Asn  Ile  Glu  Glu  Val
                    565                      570                      575

Ala  Leu  Ser  Thr  Thr  Gly  Glu  Ile  Pro  Phe  Tyr  Gly  Lys  Ala  Ile  Pro
               580                      585                      590

Leu  Glu  Val  Ile  Lys  Gly  Gly  Arg  His  Leu  Ile  Phe  Cys  His  Ser  Lys
          595                      600                      605

Lys  Lys  Cys  Asp  Glu  Leu  Ala  Ala  Lys  Leu  Val  Ala  Leu  Gly  Ile  Asn
     610                      615                      620

Ala  Val  Ala  Tyr  Tyr  Arg  Gly  Leu  Asp  Val  Ser  Val  Ile  Pro  Thr  Ser
625                           630                 635                      640

Gly  Asp  Val  Val  Val  Val  Ala  Thr  Asp  Ala  Leu  Met  Thr  Gly  Tyr  Thr
                    645                      650                      655

Gly  Asp  Phe  Asp  Ser  Val  Ile  Asp  Cys  Asn  Thr  Cys  Val  Thr  Gln  Thr
               660                 665                      670

Val  Asp  Phe  Ser  Leu  Asp  Pro  Thr  Phe  Thr  Ile  Glu  Thr  Ile  Thr  Leu
          675                 680                      685

Pro  Gln  Asp  Ala  Val  Ser  Arg  Thr  Gln  Arg  Arg  Gly  Arg  Thr  Gly  Arg
     690                      695                      700

Gly  Lys  Pro  Gly  Ile  Tyr  Arg  Phe  Val  Ala  Pro  Gly  Glu  Arg  Pro  Pro
705                      710                      715                      720

Gly  Met  Phe  Asp  Ser  Ser  Val  Leu  Cys  Glu  Cys  Tyr  Asp  Ala  Gly  Cys
                    725                 730                      735

Ala  Trp  Tyr  Glu  Leu  Thr  Pro  Ala  Glu  Thr  Thr  Val  Arg  Leu  Arg  Ala
               740                 745                      750

Tyr  Met  Asn  Thr  Pro  Gly  Leu  Pro  Val  Cys  Gln  Asp  His  Leu  Glu  Phe
          755                 760                      765

Trp  Glu  Gly  Val  Phe  Thr  Gly  Leu  Thr  His  Ile  Asp  Ala  His  Phe  Leu
     770                      775                 780

Ser  Gln  Thr  Lys  Gln  Ser  Gly  Glu  Asn  Leu  Pro  Tyr  Leu  Val  Ala  Tyr
785                      790                      795                      800
```

-continued

| Gln | Ala | Thr | Val | Cys 805 | Ala | Arg | Ala | Gln 810 | Ala | Pro | Pro | Pro | Ser | Trp 815 | Asp |
| --- | --- | --- | --- | --- | --- | --- | --- | --- | --- | --- | --- | --- | --- | --- | --- |
| Gln | Met | Trp | Lys 820 | Cys | Leu | Ile | Arg | Leu 825 | Lys | Pro | Thr | Leu | His 830 | Gly | Pro |
| Thr | Pro | Leu 835 | Leu | Tyr | Arg | Leu | Gly 840 | Ala | | | | | | | |